US007951368B2

(12) United States Patent
Li et al.

(10) Patent No.: US 7,951,368 B2
(45) Date of Patent: May 31, 2011

(54) COMPOSITIONS OF SPECIFIC BINDING AGENTS TO HEPATOCYTE GROWTH FACTOR

(75) Inventors: Tiansheng Li, Newbury Park, CA (US); Rahul Rajan, Thousand Oaks, CA (US); Zhuohong Huang, Thousand Oaks, CA (US); Karthik Nagapudi, Simi Valley, CA (US); Mariko Aoki, Chesterfield, MO (US); Alexis Lueras, Moorpark, CA (US); Grace C. Chu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 108 days.

(21) Appl. No.: 12/146,431

(22) Filed: Jun. 25, 2008

(65) Prior Publication Data

US 2009/0042315 A1 Feb. 12, 2009

Related U.S. Application Data

(60) Provisional application No. 60/937,283, filed on Jun. 25, 2007.

(51) Int. Cl.
*A61K 39/395* (2006.01)
(52) U.S. Cl. ............... 424/130.1; 424/133.1; 424/141.1; 424/145.1
(58) Field of Classification Search .................. None
See application file for complete search history.

(56) References Cited

U.S. PATENT DOCUMENTS

| | | | |
|---|---|---|---|
| 4,847,079 A | 7/1989 | Kwan | |
| 4,897,353 A | 1/1990 | Carpenter et al. | |
| 5,096,885 A | 3/1992 | Pearlman et al. | |
| 5,140,010 A | 8/1992 | Goldstein et al. | |
| 5,272,135 A | 12/1993 | Takruri | |
| 5,358,708 A | 10/1994 | Patel | |
| 5,547,696 A | 8/1996 | Sørensen | |
| 5,612,315 A | 3/1997 | Pikal et al. | |
| 5,631,225 A | 5/1997 | Sørensen | |
| 5,654,278 A | 8/1997 | Sørensen | |
| 5,756,468 A | 5/1998 | Johnson et al. | |
| 5,763,409 A | 6/1998 | Bayol et al. | |
| 5,871,736 A | 2/1999 | Bruegger et al. | |
| 5,874,408 A | 2/1999 | Nayar | |
| 5,929,028 A | 7/1999 | Skrabanja et al. | |
| 6,136,294 A | 10/2000 | Adjei et al. | |
| 6,165,467 A | 12/2000 | Hagiwara et al. | |
| 6,171,586 B1 | 1/2001 | Lam et al. | |
| 6,270,757 B1 | 8/2001 | Warne | |
| 6,447,774 B1 | 9/2002 | Metzner et al. | |
| 6,458,338 B1 | 10/2002 | Adjei et al. | |
| 6,525,102 B1 | 2/2003 | Chen et al. | |
| 6,821,515 B1 | 11/2004 | Cleland et al. | |
| 6,908,610 B1 | 6/2005 | Sato | |
| 7,195,670 B2 * | 3/2007 | Hansen et al. ............... 117/68 |
| 7,494,650 B2 * | 2/2009 | Kim et al. ............... 424/141.1 |
| 2002/0037841 A1 | 3/2002 | Papadimitriou | |
| 2003/0092622 A1 | 5/2003 | Sato et al. | |
| 2003/0104996 A1 | 6/2003 | Li et al. | |
| 2003/0133928 A1 | 7/2003 | Metzner et al. | |
| 2003/0190316 A1 | 10/2003 | Kakuta et al. | |
| 2004/0018200 A1 | 1/2004 | Oliver et al. | |
| 2004/0037803 A1 | 2/2004 | Sato | |
| 2004/0224886 A1 | 11/2004 | Chen et al. | |
| 2005/0118643 A1 * | 6/2005 | Burgess et al. ............... 435/7.1 |
| 2005/0152887 A1 | 7/2005 | Ernest | |
| 2006/0193850 A1 | 8/2006 | Warne et al. | |
| 2007/0053871 A1 * | 3/2007 | Li et al. ............... 424/85.1 |

FOREIGN PATENT DOCUMENTS

| | | |
|---|---|---|
| EP | 0082481 B1 | 3/1985 |
| EP | 0082481 B2 | 9/1990 |
| EP | 1417972 A1 | 5/2004 |
| JP | 05331071 A | 12/1993 |
| JP | 07173074 A | 7/1995 |
| RU | 2178309 C2 | 1/2002 |
| WO | WO 98/22136 A2 | 5/1998 |
| WO | WO 98/22136 A3 | 8/1998 |
| WO | WO 01/05355 A2 | 1/2001 |
| WO | WO 01/05355 A3 | 1/2001 |
| WO | WO 04/000347 A1 | 12/2003 |
| WO | WO 2004/082708 A2 | 9/2004 |
| WO | WO 2004/082708 A3 | 9/2004 |
| WO | WO 2004/091656 A2 | 10/2004 |
| WO | WO 2004/091656 A3 | 10/2004 |
| WO | WO 2004/100979 A2 | 11/2004 |
| WO | WO 2004/100979 A3 | 11/2004 |
| WO | WO 2005/004901 A1 | 1/2005 |
| WO | WO 2005/009393 A2 | 2/2005 |
| WO | WO 2005/016365 A2 | 2/2005 |
| WO | WO 2005/009393 A3 | 4/2005 |
| WO | WO 2005/016365 A3 | 4/2005 |
| WO | WO 2005/044854 A2 | 5/2005 |
| WO | WO 2005/049078 A2 | 6/2005 |
| WO | WO 2005/058283 A2 | 6/2005 |
| WO | WO 2005/058283 A3 | 6/2005 |

(Continued)

OTHER PUBLICATIONS

Akers et al., "Glycine Crystallization During Freezing: The Effects of Salt Form, pH, and Ionic Strength," *Pharmaceutical Research* 12(10): 1457-1461 (1995).
Arakawa et al., "Stabilization of Protein Structure by Sugars," *Biochemistry* 21: 6536-6544 (1982).
Arakawa et al., "Preferential Interactions of Proteins with Solvent Components in Aqueous Amino Acid Solutions," *Archives Biochemistry Biophysics* 224(1): 169-177 (1983).
Arakawa et al., "Biotechnology applications of amino acids in protein purification and formulations," *Amino Acids* 33: 587-605(2007).
Asquith et al., "A Study of the Ultraviolet Yellowing of Amino Acids, Peptides, and Soluble Proteins," *Textile Research J.* 40(3): 285-289 (1970).

(Continued)

*Primary Examiner* — Marianne P Allen

(57) ABSTRACT

Compositions comprising nonpolar amino acids and specific binding agents to hepatocyte growth factor (HGF) are provided. Methods of making and using such compositions are also provided.

9 Claims, 25 Drawing Sheets

(2 of 25 Drawing Sheet(s) Filed in Color)

FOREIGN PATENT DOCUMENTS

| | | |
|---|---|---|
| WO | WO 2005/058346 A1 | 6/2005 |
| WO | WO 2005/049078 A3 | 7/2005 |
| WO | WO 2005/063291 A1 | 7/2005 |
| WO | WO 2005/063298 A1 | 7/2005 |
| WO | WO 2005/044854 A3 | 8/2005 |
| WO | WO 2005/117949 A1 | 12/2005 |
| WO | WO 2006/112838 A1 | 10/2006 |
| WO | WO 2007/036745 A2 | 4/2007 |
| WO | WO 2007/036745 A3 | 8/2007 |

OTHER PUBLICATIONS

Baynes et al., "Role of Arginine in the Stabilization of Proteins Against Aggregation," *Biochemistry* 44: 4919-4925 (2005).

Bhatnagar et al., "Study of the Individual Contributions of Ice Formation and Freeze-Concentration on Isothermal Stability of Lactate Dehydrogenase during Freezing," *J. Pharmaceutical Sciences* 97(2): 798-814 (2007, online).

Bush et al., "The Formulation of Recombinant Factor IX: Stability, Robustness, and Convenience," *Seminars Hematology* 35(2, Supp. 2): 18-21 (1998).

Carpenter et al., "The Mechanism of Cryoprotection of Proteins by Solutes," *Cryobiology* 25: 244-255 (1988).

Carpenter et al., "Interactions of Stabilizing Additives with Proteins During Freeze-Thawing and Freeze-Drying," *International Biological Product Freeze-Drying and Formulation*, Bethesda, USA, 1990, published in *Develop. boil. Standard.*, 74: 225-239 (1991).

Chang et al., "Surface-Induced Denaturation of Proteins during Freezing and Its Inhibition by Surfactants," *J. Pharmaceutical Sciences* 85(12): 1325-1330 (1996).

Chang et al, "Mechanism of Protein Stabilization by Sugar During Freeze-Drying and Storage: Native Structure Preservation, Specific Interaction, and/or Immobilization in a Glassy Matrix?," *J. Pharmaceutical Sciences* 94(7): 1427-1444 (2005).

Cheung et al., "Comparative Pharmacokinetics, Safety, and Tolerability After Subcutaneous Administration of Recombinant Human Erythropoietin Formulated with Different Stabilizers," *Biopharmaceutics & Drug Disposition* 21: 211-219 (2000).

Fatouros et al., "Recombination factor VIII SQ—influence of oxygen, metal, ions, pH and ionic strength on its stability in aqueous solution," *International J. Pharmaceutics* 155: 121-131 (1997).

Franks, "Protein Destabilization at Low Temperatures," *Advances Protein Chemistry* 46: 105-139 (1995).

Gekko et al., "Mechanism of protein stabilization by glycerol: preferential hydration in glycerol-water mixtures," *Biochemistry* 20(16): 4667-4676 (1981).

Hager et al., "Investigation of Phase Behavior and Water Binding in Poly(alkylene Oxide) Solutions," *J. Applied Polymer Science* 25: 1559-1571 (1980).

Her et al., "Measurement of Glass Transition Temperatures of Freeze-Concentrated Solutes by Differential Scanning Calorimetry," *Pharmaceutical Research* 11(1): 54-59 (1994).

Her et al., "Electrolyte-Induced Changes in Glass Transition Temperatures of Freeze-Concentrated Solutes," *Pharmaceutical Research* 12(5): 768-772 (1995).

Huang et al., "Interaction Between Poly(ethylene glycol) and Water as Studied by Differential Scanning Calorimetry," *J. Polymer Science: Part B: Polymer Physics* 39:496-506 (2001).

Izutsu et al., "Decreased Protein-Stabilizing Effects of Cryoprotectants Due to Crystallization," *Pharmaceutical Research* 10(8): 1232-1237 (1993).

Izutsu et al., "Excipient crystallinity and its protein-structure-stabilizing effect during freeze-drying," *J. Pharmacy Pharmacology* 54: 1033-1039 (2002).

Lam et al., "Antioxidants for Prevention of Methionine Oxidation in Recombinant Monoclonal Antibody HER2," *J. Pharmaceutical Science* 86(11): 1250-1255 (1997).

"Lecture 15: 'Stealth' particles," from Molecular Principles of Biomaterials, Spring 2003, available online at: http://dspace.mit.edu/bitstream/handle/1721.1/36892/BE-462JSpring-2003/NR/rdonlyres/Biological-Engineering-Division/BE-462JMolecular-Principles-of-BiomaterialsSpring2003/67DAE099-B783-4AF0-8A83-CAD20EA431DE/0/BE462lect15.pdf (8 pages).

Lee et al., "The Stabilization of Proteins by Sucrose," *J. Biological Chemistry* 256(14): 7193-7201 (1981).

Lee et al. "Thermal Stability of Proteins in the Presence of Poly(ethylene glycols)," *Biochemistry* 26: 7813-7819 (1987).

Li et al., "Kinetics of Glycine Crystallization during Freezing of Sucrose/Glycine Excipient Systems," *J. Pharmaceutical Sciences* 94(3): 625-631 (2005).

Moreira et al., "Effect of Formulation on Stability of Freeze-dried Recombinant Human Alpha Interferon," *Cryo-Letters*, 16: 275-282 (1995).

Piedmonte et al., "Sorbitol Crystallization Can Lead to Protein Aggregation in Frozen Protein Formulations," *Pharmaceutical Research* 24(1): 136-146 (2006).

Price II et al., "Understanding the physical properties that control protein crystallization by analysis of large-scale experimental data," *Nature Biotechnology* 27(1): 51-57 (2009).

Privalov et al., "Cold Denaturation of Myoglobin," *J. Molecular Biology* 190: 487-498 (1986).

Privalov, "Cold Denaturation of Proteins," *Critical Reviews in Biochemistry Molecular Biology* 25(4): 281-305 (1990).

Schering-Plough Corporation Statements of Consolidated Operations (Unaudited) for 2003 and 2004 (7 pages).

Shamblin et al., "The Effects of Co-lyophilized Polymeric Additives on the Glass Transition Temperature and Crystallization of Amorphous Sucrose," *J. Thermal Analysis* 47: 1567-1579 (1996).

Strambini et al., "Proteins in Frozen Solutions: Evidence of Ice-Induced Partial Unfolding," *Biophysical J.* 70: 971-976 (1996).

Szenczi et al., "The effect of solvent environment on the conformation and stability of human polyclonal IgG in solution," *Biologicals* 34: 5-14 (2006).

Tian et al., "Calorimetric investigation of protein/amino acid interactions in the solid state," *International J. Pharmaceuticals* 310: 175-186 (2006).

Tian et al., "Spectroscopic evaluation of the stabilization of humanized monoclonal antibodies in amino acid formulations," *International J. Pharmaceutics* 335: 20-31 (2007).

Tsumoto et al. "The mechanism of arginine interaction with proteins," poster presentation, Alliance Protein Laboratories, Thousand Oaks, CA (1 page).

Van Den Berg et al., "Effect of Freezing on the pH and Composition of Sodium and Potassium Phosphate Solutions; the Reciprocal System $KH_2PO_4$-$Na_2$-$HPO_4$-$H_2O$)," *Archives Biochemistry Biopohysics* 81: 319-329 (1959).

Xie et al., "The thermodynamic mechanism of protein stabilization by trehalose," *Biophysical Chemistry* 64: 25-43 (1997).

\* cited by examiner (a)

(b)

(c)

A.

B.

(a)

(b)

US 7,951,368 B2

COMPOSITIONS OF SPECIFIC BINDING AGENTS TO HEPATOCYTE GROWTH FACTOR

This application claims the benefit of U.S. Provisional Application No. 60/937,283, filed Jun. 25, 2007, which is incorporated herein by reference for any purpose.

FIELD

Compositions comprising nonpolar amino acids and specific binding agents to hepatocyte growth factor (HGF) are provided. Methods of making and using such compositions are also provided.

BACKGROUND

Hepatocyte Growth Factor (HGF) is a potent mitogen for hepatocytes in certain instances. HGF is also a secretory protein of fibroblasts and smooth muscle that induces motility of epithelial cells in certain instances. Certain specific binding agents to HGF, including, but not limited to, antibodies, have been described. See, e.g., U.S. Publication No. 2005/0118643, published Jun. 2, 2005, which is hereby incorporated by reference for any purpose.

SUMMARY

In certain embodiments, a composition is provided that comprises a specific binding agent to HGF, at least one stabilizing agent, and a buffering agent, wherein the at least one stabilizing agent is at least one nonpolar amino acid, and wherein the pH of the composition is above 5.4. In certain embodiments, the specific binding agent is selected from an antibody, a polyclonal antibody, a monoclonal antibody, an antibody wherein the heavy chain and the light chain are connected by a flexible linker, an Fv molecule, a maxibody, an immunologically functional immunoglobulin fragment, a Fab fragment, a Fab' fragment, a F(ab')$_2$ molecule, a fully human antibody, a humanized antibody, a chimeric antibody, and an antibody that substantially inhibits binding of HGF to a c-Met receptor. In certain embodiments, the specific binding agent is a fully human antibody, wherein the fully human antibody is 2.12.1. In certain embodiments, the specific binding agent to HGF is at a concentration of 0.5 mg/ml to 200 mg/ml. In certain embodiments, the specific binding agent to HGF is at a concentration of 30 mg/ml.

In certain embodiments, a composition is provided that comprises a specific binding agent to HGF, at least one stabilizing agent, a buffering agent, wherein the at least one stabilizing agent is at least one nonpolar amino acid, and wherein the pH of the composition is above 5.4, and that further comprises at least one additional pharmaceutical agent.

In certain embodiments, a composition is provided that comprises a specific binding agent to HGF; at least one stabilizing agent; and a buffering agent; wherein the at least one stabilizing agent is at least one nonpolar amino acid; wherein the at least one nonpolar amino acid is selected from glycine, alanine, valine, leucine, isoleucine, proline, methionine, phenylalanine, and tryptophan; and wherein the pH of the composition is above 5.4. In certain embodiments, the at least one nonpolar amino acid is alanine, and wherein alanine is present at a concentration of at least 0.02 M, or 0.02 M, or 0.2 M. In certain embodiments, the at least one nonpolar amino acid is leucine, and wherein leucine is present at a concentration of at least 0.02 M, or 0.02 M, or 0.075 M. In certain embodiments, the at least one nonpolar amino acid is methionine, and discoloration of the composition is reduced. In certain embodiments, methionine is present at a concentration of at least 0.001 M, or 0.01 M.

In certain embodiments, the at least one nonpolar amino acid is a first nonpolar amino acid and a second nonpolar amino acid. In certain embodiments, the first nonpolar amino acid is alanine and the second nonpolar amino acid is leucine. In certain embodiments, alanine is present at a concentration of at least 0.02 M, or 0.02 M, or 0.2 M; and leucine is present at a concentration of at least 0.02 M, or 0.2 M, or 0.075 M. In certain embodiments, the at least one nonpolar amino acid is a first nonpolar amino acid, a second nonpolar amino acid, and a third nonpolar amino acid. In certain embodiments, the first nonpolar amino acid is alanine, the second nonpolar amino acid is leucine, and the third nonpolar amino acid is methionine, and discoloration of the composition is reduced. In certain embodiments, alanine is present at a concentration of at least 0.02 M, or 0.02 M, or 0.2 M; leucine is present at a concentration of at least 0.02 M, or 0.02 M, or 0.075 M; and methionine is present at a concentration of at least 0.001 M, or 0.01 M.

In certain embodiments, a composition is provided that comprises a specific binding agent to HGF, at least one stabilizing agent, and a buffering agent, wherein the at least one stabilizing agent is at least one nonpolar amino acid, wherein the buffering agent is selected from histidine, propionate, and acetate, and wherein the pH of the composition is above 5.4. In certain embodiments, the pH of the composition is 5.7. In certain embodiments, the pH of the composition is 5.6. In certain embodiments, the buffering agent is present at a concentration of at least 0.01 M, or 0.01 M.

In certain embodiments, a composition is provided that comprises a specific binding agent to HGF, at least one stabilizing agent, a buffering agent, and a sugar, wherein the at least one stabilizing agent is at least one nonpolar amino acid, and wherein the pH of the composition is above 5.4. In certain embodiments, the sugar is sorbitol. In certain embodiments, sorbitol is present at a concentration of at least 5%, or 5%.

In certain embodiments, a composition is provided that comprises a specific binding agent to HGF, at least one stabilizing agent, a buffering agent, and a surfactant, wherein the at least one stabilizing agent is at least one nonpolar amino acid, and wherein the pH of the composition is above 5.4. In certain embodiments, a composition is provided that comprises a specific binding agent to HGF, at least one stabilizing agent, a buffering agent, a surfactant, and a sugar, wherein the at least one stabilizing agent is at least one nonpolar amino acid, and wherein the pH of the composition is above 5.4. In certain embodiments, the surfactant is polysorbate 20. In certain embodiments, polysorbate 20 is present at a concentration of at least 0.002%. In certain embodiments, polysorbate 20 is present at a concentration of at least 0.004%. In certain embodiments, polysorbate 20 is present at a concentration of 0.004%.

In certain embodiments, a composition is provided that comprises a specific binding agent to HGF; at least one stabilizing agent; and a buffering agent; wherein the at least one stabilizing agent is at least one nonpolar amino acid and at least one cryoprotectant, and wherein the pH of the composition is above 5.4. In certain embodiments, the at least one nonpolar amino acid is a first nonpolar amino acid and a second nonpolar amino acid. In certain embodiments, the first nonpolar amino acid is alanine and the second nonpolar amino acid is leucine. In certain embodiments, alanine is present at a concentration of at least 0.02 M, or 0.02 M, or 0.2 M; and leucine is present at a concentration of at least 0.02 M, or 0.02 M, or 0.075 M. In certain embodiments, the at least one cryoprotectant is selected from hydrophilic polymers, alcohols, sugars, and basic amino acids. In certain embodiments, the at least one cryoprotectant is at least one hydrophilic polymer, wherein the at least one hydrophilic polymer is selected from polyvinylpyrrolidone K15 and polyethylene glycol, and wherein the molecular weight of the polyethylene glycol is from 200 to 30,000. In certain embodiments, the at least one cryoprotectant is at least one hydrophilic polymer, wherein the at least one hydrophilic polymer is selected from polyethylene glycol 200, polyethylene glycol 400, polyethylene glycol 600, polyethylene glycol 4000, and polyethylene glycol 30,000. In certain embodiments, the at least one cryoprotectant is at least one alcohol, wherein the at least one alcohol is selected from ethanol, 2-propanol, propylene glycol, hexanediol, L-(+)-2,3-butanediol, and (±)2-methyl-2,4, pentanediol. In certain embodiments, the at least one cryoprotectant is at least one sugar, wherein the at least one sugar is selected from glucose, mannose, sucrose, lactose, mannitol, xylitol, erythritol, threitol, sorbitol, inositol, glycerol, L-gluconate, trehalose, and raffinose. In certain embodiments, the at least one cryoprotectant is at least one basic amino acid, wherein the at least one basic amino acid is selected from arginine and histidine. In certain embodiments, the at least one cryoprotectant is present at a concentration of 0.1 M.

In certain embodiments, an article of manufacture is provided that comprises a container holding a composition comprising a specific binding agent to HGF, at least one stabilizing agent, and a buffering agent.

In certain embodiments, a method for formulating a specific binding agent to HGF in a composition is provided that comprises combining the specific binding agent to HGF, at least one stabilizing agent, and a buffering agent.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 14 (*b*) shows the results of native SEC-HPLC analysis (expressed as percent main peak (monomer)) of various 2.12.1 compositions subjected to zero, three, or five freeze/thaw cycles, with the freeze temperature at −70° C., according to the work discussed in Example 4.

FIG. 18 (b) shows the results of native SEC-HPLC analysis (expressed as percent main peak (monomer)) of various 2.12.1 compositions incubated at −30° C. for 0 weeks, 4 weeks, or 3 months according to the work discussed in Example 8.

FIG. 20 (b) shows a plot of the "% Increase in HMW" vs. the hydropathic index of the amino acid in various 2.12.1 compositions incubated at 37° C. for 4 weeks according to the work discussed in Example 10.

FIG. 23 (b) shows the results of native SEC-HPLC analysis (expressed as percent high molecular weight species) of two 2.12.1 compositions subjected to zero, five, or ten freeze/thaw cycles, with the freeze temperature at −30° C., according to the work discussed in Example 13.

DETAILED DESCRIPTION OF CERTAIN EMBODIMENTS

Figure 1:
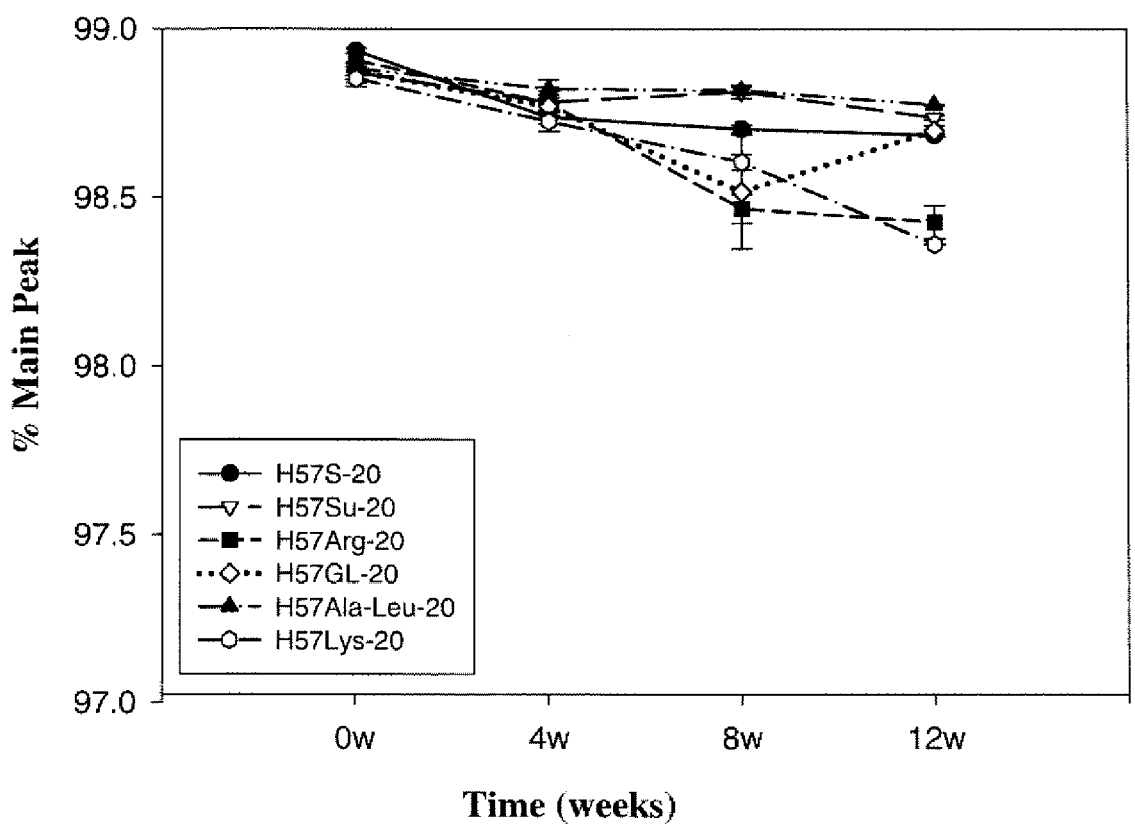
FIG. 1 shows the results of native SEC-HPLC analysis (expressed as percent main peak (monomer)) of various 2.12.1 compositions incubated at 37° C. for 0 weeks, 4 weeks, 8 weeks, or 12 weeks according to the work discussed in Example 1

The section headings used herein are for organizational purposes only and are not to be construed as limiting the subject matter described. All documents or portions of documents cited in this application, including but not limited to patents, patent applications, articles, books, and treatises, are expressly incorporated by reference herein in their entirety for any purpose. In the event that one or more of the documents, or portions of documents, incorporated by reference defines a term that contradicts that term's definition in this application, this application controls.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, delivery, and treatment of patients.

In this application, the use of the singular includes the plural unless specifically stated otherwise. In this application, the word "a" or "an" means "at least one" unless specifically stated otherwise. In this application, the use of "or" means "and/or" unless specifically stated otherwise. In the context of a multiple dependent claim, the use of "or" refers back to more than one preceding independent or dependent claim in the alternative only. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

Certain Definitions

As utilized in accordance with the present disclosure, the following terms, unless otherwise indicated, shall be understood to have the following meanings The term "hepatocyte growth facto" or "HGF" refers to a polypeptide as set forth in Nakamura et al., Nature 342: 440-443 (1989) or fragments thereof, as well as related polypeptides, which include, but are not limited to, allelic variants, splice variants, derivative variants, substitution variants, deletion variants, and/or insertion variants, fusion polypeptides, and interspecies homologs. In certain embodiments, an HGF polypeptide includes terminal residues, such as, but not limited to, leader sequence residues, targeting residues, amino terminal methionine residues, lysine residues, tag residues and/or fusion protein residues.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an immunoglobulin. In certain embodiments, a specific binding agent is an immunoglobulin fragment. In certain embodiments, a specific binding agent is an antibody. In certain embodiments, a specific binding agent is an antigen binding region.

The term "specific binding agent to HGF" refers to a specific binding agent that specifically binds any portion of HGF. In certain embodiments, a specific binding agent to HGF is an immunoglobulin. In certain embodiments, a specific binding agent to HGF is an immunoglobulin fragment. In certain embodiments, a specific binding agent to HGF is an antibody to HGF. In certain embodiments, a specific binding agent is an antigen binding region.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore® assay. In certain embodiments, affinity is determined by a kinetic method. In certain embodiments, affinity is determined by an equilibrium/solution method.

The term "target" refers to a molecule or a portion of a molecule capable of being bound by a specific binding agent. In certain embodiments, a target may have one or more epitopes. In certain embodiments, a target is an antigen.

The term "epitope" refers to a portion of a molecule capable of being bound by a specific binding agent. Exemplary epitopes may comprise any polypeptide determinant capable of specific binding to an immunoglobulin and/or T-cell receptor. Exemplary epitope determinants include, but are not limited to, chemically active surface groupings of molecules, for example, but not limited to, amino acids, sugar side chains, phosphoryl groups, and sulfonyl groups. In certain embodiments, epitope determinants may have specific three dimensional structural characteristics, and/or specific charge characteristics. In certain embodiments, an epitope is a region of an antigen that is bound by an antibody. Epitopes may be contiguous or non-contiguous. In certain embodiments, epitopes may be mimetic in that they comprise a three dimensional structure that is similar to an epitope used to generate the antibody, yet comprise none or only some of the amino acid residues found in that epitope used to generate the antibody.

"Antibody" or "antibody peptide(s)" both refer to an intact antibody, or a fragment thereof. In certain embodiments, the fragment includes contiguous portions of an intact antibody. In certain embodiments, the fragment includes non-contiguous portions of an intact antibody. In certain embodiments, the antibody fragment may be a binding fragment that competes with the intact antibody for specific binding. The term "antibody" also encompasses polyclonal antibodies and monoclonal antibodies. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')2, Fv, scFv, maxibodies, and single-chain antibodies. Non-antigen binding fragments include, but are not limited to, Fc fragments. The term "antibody" also encompasses anti-idiotypic antibodies that specifically bind to the variable region of another antibody. In certain embodiments, an anti-idiotypic antibody specifically binds to the variable region of an anti-HGF antibody. In certain embodiments, anti-idiotypic antibodies may be used to detect the presence of a particular anti-HGF antibody in a sample or to block the activity of an anti-HGF antibody.

The term "polyclonal antibody" refers to a heterogeneous mixture of antibodies that bind to different epitopes of the same antigen.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

"Chimeric antibody" refers to an antibody that has an antibody variable region of a first species fused to another molecule, for example, an antibody constant region of another second species. See, e.g., U.S. Pat. No. 4,816,567 and Morrison et al., *Proc Natl Acad Sci* (*USA*), 81:6851-6855 (1985). In certain embodiments, the first species may be different from the second species. In certain embodiments, the first species may be the same as the second species. In certain embodiments, a chimeric antibody is a CDR-grafted antibody.

The term "CDR-grafted antibody" refers to an antibody in which the CDR from one antibody is inserted into the framework of another antibody. In certain embodiments, the antibody from which the CDR is derived and the antibody from which the framework is derived are of different species. In certain embodiments, the antibody from which the CDR is derived and the antibody from which the framework is derived are of different isotypes.

The term "multi-specific antibody" refers to an antibody wherein two or more variable regions bind to different epitopes. The epitopes may be on the same or different targets. In certain embodiments, a multi-specific antibody is a "bi-specific antibody," which recognizes two different epitopes on the same or different antigens.

The term "catalytic antibody" refers to an antibody in which one or more catalytic moieties is attached. In certain embodiments, a catalytic antibody is a cytotoxic antibody, which comprise a cytotoxic moiety.

The term "humanized antibody" refers to an antibody in which all or part of an antibody framework region is derived from a human, but all or part of one or more CDR regions is derived from another species, for example, including, but not limited to, a mouse.

The term "fully human antibody" refers to an antibody in which both the CDR and the framework comprise substantially human sequences. In certain embodiments, fully human antibodies are produced in non-human mammals, including, but not limited to, mice, rats, and lagomorphs. In certain embodiments, fully human antibodies are produced in hybridoma cells. In certain embodiments, fully human antibodies are produced recombinantly.

The term "anti-idiotype antibody" refers to an antibody that specifically binds to another antibody.

The term "heavy chain" includes any polypeptide having sufficient variable region sequence to confer specificity for a target. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxy-terminus. The term "heavy chain", as used herein, encompasses a full-length heavy chain and fragments thereof.

The term "light chain" includes any polypeptide having sufficient variable region sequence to confer specificity for a target. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof.

The term "Fab fragment" refers to an antibody comprising one light chain and the $C_H1$ and variable regions of one heavy chain. The heavy chain of a Fab fragment cannot form a disulfide bond with another heavy chain. In certain embodiments, the heavy chain of a Fab fragment forms a disulfide bond with the light chain of a Fab fragment.

The term "Fab' fragment" refers to an antibody comprising one light chain, the variable and $C_H1$ regions of one heavy chain, and some of the constant region between the $C_H1$ and $C_H2$ domains of the heavy chain. In certain embodiments, an interchain disulfide bond can be formed between two heavy chains of an Fab' fragment to form a F(ab')$_2$ molecule.

The term "F(ab')$_2$ molecule" refers to an antibody comprising two Fab' fragments connected by an interchain disulfide bond formed between two heavy chains.

An "Fv molecule" comprises the variable regions from both the heavy and light chains, but lacks the constant regions. A single chain variable fragment (scFv) comprises variable regions from both a heavy and a light chain wherein the heavy and light chain variable regions are fused to form a single polypeptide chain which forms an antigen-binding region. In certain embodiments, a scFV comprises a single polypeptide chain. A single-chain antibody comprises a scFV. In certain embodiments, a single-chain antibody comprises one or more additional polypeptides fused to a scFv. Exemplary additional polypeptides include, but are not limited to, one or more constant regions. Exemplary single-chain antibodies are discussed, e.g., in WO 88/01649 and U.S. Pat. Nos. 4,946,778 and 5,260,203.

The term "maxibody" refers to a scFv fused (may be by a linker or direct attachment) to an Fc or an Fc fragment. In certain embodiments, a single chain antibody is a maxibody. In certain embodiments, a single chain antibody is a maxibody that binds to HGF. Exemplary Ig-like domain-Fc fusions are disclosed in U.S. Pat. No. 6,117,655.

An "Fc fragment" comprises the $C_H2$ and $C_H3$ domains of the heavy chain and contains some of the constant region, between the $C_H1$ and $C_H2$ domains, such that an interchain disulfide bond can be formed between two heavy chains.

As used herein, a "flexible linker" refers to any linker that is not predicted by one skilled in the art, according to its chemical structure, to be fixed in three-dimensional space. In certain embodiments, a peptide linker comprising three or more amino acids is a flexible linker.

The terms "variable region" and "variable domain" are used interchangeably herein to refer to a portion of the light and/or heavy chains of an antibody. In various instances, variable domains include approximately the amino-terminal 120 to 130 amino acids in the heavy chain and about 100 to 110 amino-terminal amino acids in the light chain. In certain embodiments, variable regions of different antibodies differ extensively in amino acid sequence even among antibodies of the same species. The variable region of an antibody, in various instances, determines specificity of a particular antibody for its target.

The term "immunologically functional immunoglobulin fragment" refers to a polypeptide fragment comprising at least the variable domains of an immunoglobulin heavy chain and an immunoglobulin light chain. In certain embodiments, an immunologically functional immunoglobulin fragment is capable of binding to a ligand, preventing binding of the ligand to its receptor, and thereby interrupting a biological response resulting from ligand binding to the receptor. In certain embodiments, an immunologically functional immunoglobulin fragment is capable of binding to a receptor, preventing binding of the ligand to its receptor, and thereby interrupting a biological response resulting from ligand binding to the receptor. In certain embodiments, an immunologically functional immunoglobulin fragment is capable of binding a receptor and activating that receptor. In certain embodiments, an immunologically functional immunoglobulin fragment is capable of binding a receptor and inactivating that receptor.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "isolated polynucleotide" refers to a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The term "operably linked" refers to components that are in a relationship permitting them to function in their intended manner. For example, in the context of a polynucleotide sequence, a control sequence may be "operably linked" to a coding sequence when the control sequence and coding sequence are in association with each other in such a way that expression of the coding sequence is achieved under conditions compatible with the functioning of the control sequence.

The term "control sequence" refers to polynucleotide sequences which may effect the expression and processing of coding sequences with which they are in association. The nature of such control sequences may differ depending upon the host organism. Certain exemplary control sequences for prokaryotes include, but are not limited to, promoters, ribosomal binding sites, and transcription termination sequences. Certain exemplary control sequences for eukaryotes include, but are not limited to, promoters, enhancers, and transcription termination sequences. In certain embodiments, "control sequences" can include leader sequences and/or fusion partner sequences.

The terms "isolated polypeptide" and "isolated peptide" refer to any polypeptide that (1) is free of at least some proteins with which it would normally be found, (2) is essentially free of other proteins from the same source, e.g., from the same species, (3) is expressed by a cell from a different species, or (4) does not occur in nature.

The terms "polypeptide," "peptide," and "protein" are used interchangeably herein and refer to a polymer of two or more amino acids joined to each other by peptide bonds or modified peptide bonds, i.e., peptide isosteres. The terms apply to amino acid polymers containing naturally occurring amino acids as well as amino acid polymers in which one or more amino acid residues is a non-naturally occurring amino acid or a chemical analogue of a naturally occurring amino acid. An amino acid polymer may contain one or more amino acid residues that has been modified by one or more natural processes, such as post-translational processing, and/or one or more amino acid residues that has been modified by one or more chemical modification techniques known in the art.

As used herein, the twenty conventional amino acids and their abbreviations follow conventional usage, See Immunology—A Synthesis (2nd Edition, E. S. Golub and D. R. Gren, Eds., Sinauer Associates, Sunderland, Mass. (1991)). In certain embodiments, one or more unconventional amino acids may be incorporated into a polypeptide. The term "unconventional amino acid" refers to any amino acid that is not one of the twenty conventional amino acids. The term "non-naturally occurring amino acids" refers to amino acids that are not found in nature. Non-naturally occurring amino acids are a subset of unconventional amino acids. Unconventional amino acids include, but are not limited to, stereoisomers (e.g., D-amino acids) of the twenty conventional amino acids, unnatural amino acids such as α-, α-disubstituted amino acids, N-alkyl amino acids, lactic acid, homoserine, homocysteine, 4-hydroxyproline, γ-carboxyglutamate, ε-N, N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline) known in the art. In the polypeptide notation used herein, the left-hand direction is the amino terminal direction and the righthand direction is the carboxy-terminal direction, in accordance with standard usage and convention.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide. In certain embodiments, a variant of a reference polypeptide has an altered post-translational modification site (i.e., a glycosylation site). In certain embodiments, both a reference polypeptide and a variant of a reference polypeptide are specific binding agents. In certain embodiments, both a reference polypeptide and a variant of a reference polypeptide are antibodies.

Variants of a reference polypeptide include, but are not limited to, glycosylation variants. Glycosylation variants include variants in which the number and/or type of glycosylation sites have been altered as compared to the reference polypeptide. In certain embodiments, glycosylation variants of a reference polypeptide comprise a greater or a lesser number of N-linked glycosylation sites than the reference polypeptide. In certain embodiments, an N-linked glycosylation site is characterized by the sequence Asn-X-Ser or Asn-X-Thr, wherein the amino acid residue designated as X may be any amino acid residue except proline. In certain embodiments, glycosylation variants of a reference polypeptide comprise a rearrangement of N-linked carbohydrate chains wherein one or more N-linked glycosylation sites (typically those that are naturally occurring) are eliminated and one or more new N-linked sites are created.

Variants of a reference polypeptide include, but are not limited to, cysteine variants. In certain embodiments, cysteine variants include variants in which one or more cysteine residues of the reference polypeptide are replaced by one or more non-cysteine residues; and/or one or more non-cysteine residues of the reference polypeptide are replaced by one or more cysteine residues. Cysteine variants may be useful, in certain embodiments, when a particular polypeptide must be refolded into a biologically active conformation, e.g., after the isolation of insoluble inclusion bodies. In certain embodiments, cysteine variants of a reference polypeptide have fewer cysteine residues than the reference polypeptide. In certain embodiments, cysteine variants of a reference polypeptide have an even number of cysteines to minimize interactions resulting from unpaired cysteines. In certain embodiments, cysteine variants have more cysteine residues than the native protein.

In certain embodiments, conservative modifications to the heavy and light chains of a particular antibody (and corresponding modifications to the encoding nucleotides) will produce antibodies having functional and chemical characteristics similar to those of the original antibody. In contrast, in certain embodiments, substantial modifications in the functional and/or chemical characteristics of a particular antibody may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

Certain desired amino acid substitutions (whether conservative or non-conservative) can be determined by those skilled in the art at the time such substitutions are desired. In certain embodiments, amino acid substitutions can be used to identify important residues of particular antibodies, such as those which may increase or decrease the affinity of the antibodies or the effector function of the antibodies.

In certain embodiments, the effects of an antibody may be evaluated by measuring a reduction in the amount of symptoms of the disease. In certain embodiments, the disease of interest may be caused by a pathogen. In certain embodiments, a disease may be established in an animal host by other methods including introduction of a substance (such as a carcinogen) and genetic manipulation. In certain embodiments, effects may be evaluated by detecting one or more adverse events in the animal host. The term "adverse event" includes, but is not limited to, an adverse reaction in an animal host that receives an antibody that is not present in an animal host that does not receive the antibody. In certain embodiments, adverse events include, but are not limited to, a fever, an immune response to an antibody, inflammation, and/or death of the animal host.

Various antibodies specific to an antigen may be produced in a number of ways. In certain embodiments, an antigen containing an epitope of interest may be introduced into an animal host (e.g., a mouse), thus producing antibodies specific to that epitope. In certain instances, antibodies specific to an epitope of interest may be obtained from biological samples taken from hosts that were naturally exposed to the epitope. In certain instances, introduction of human immunoglobulin (Ig) loci into mice in which the endogenous Ig genes have been inactivated offers the opportunity to obtain human monoclonal antibodies (MAbs).

The term "agent" is used herein to denote a chemical compound, a mixture of chemical compounds, a biological molecule, a biological macromolecule, or an extract made from biological materials.

The term "stabilizing agent" refers to an agent that stabilizes a specific binding agent to HGF in a composition. A specific binding agent to HGF is "stabilized" in a composition if the specific binding agent retains more of its physical stability and/or chemical stability and/or biological activity in a composition comprising a stabilizing agent compared with the composition not comprising the stabilizing agent. In certain embodiments, a stabilizing agent reduces discoloration of a composition comprising a specific binding agent to HGF. In certain embodiments, a stabilizing agent is a cryoprotectant.

The phrase "retains its physical stability" means that a specific binding agent to HGF in a composition shows less aggregation, precipitation, and/or denaturation in a composition comprising a stabilizing agent compared with the composition not comprising the stabilizing agent.

The phrase "retains its chemical stability" means that a specific binding agent to HGF in a composition shows less chemical alteration in a composition comprising a stabilizing agent compared with the composition not comprising the stabilizing agent. Examples of chemical alteration include, but are not limited to, size modification, for example, including, but not limited to, clipping. Clipping refers to cleavage of a specific binding agent to HGF that results in smaller, lower molecular weight fragments. In certain embodiments, clipping is a result of proteolysis. Examples of chemical alteration include, but are not limited to, charge alteration, for example, including, but not limited to, deamidation. Examples of chemical alteration include, but are not limited to, hydrophilic/hydrophobic alteration, for example, including, but not limited to, oxidation.

The phrase "retains its biological activity" means that a specific binding agent to HGF in a composition demonstrates more biological activity at a given time after the composition was prepared in a composition comprising a stabilizing agent compared with the composition not comprising the stabilizing agent. In certain embodiments, biological activity is determined by an assay appropriate for determining biological activity. Exemplary assays to determine biological activity of a specific binding agent include, but are not limited to, antigen binding assays and receptor phosphorylation assays. Exemplary antigen binding assays include, but are not limited to, ELISA assays, immunoprecipitation assays, and affinity assays, for example, including, but not limited to, BIAcore® assays. Certain exemplary methods and assays to determine biological activity of specific binding agents to HGF have been described, e.g., in U.S. Publication No. 2005/0118643, published Jun. 2, 2005.

"Aggregation" refers to the formation of multimers of individual protein molecules through non-covalent or covalent interactions. Aggregation can be reversible or irreversible. In certain instances, when the loss of tertiary structure or partial unfolding occurs, hydrophobic amino acid residues which are typically hidden within the folded protein structure are exposed to the solution. In certain instances, this promotes hydrophobic-hydrophobic interactions between individual protein molecules, resulting in aggregation. Srisailam et al., J Am Chem Soc 124 (9):1884-8 (2002), for example, has determined that certain conformational changes of a protein accompany aggregation, and that certain regions of specific proteins can be identified as particularly responsible for the formation of aggregates. In certain instances, protein aggregation can be induced by heat (Sun et al., J Agric Food Chem 50(6): 1636-42 (2002)), organic solvents (Srisailam et al., supra), and reagents such as SDS and lysophospholipids (Hagihara et al., Biochem 41(3): 1020-6 (2002)). Aggregation can be a significant problem in in vitro protein purification and formulation.

"Aggregates" refers to multimers of individual protein molecules formed by aggregation. Aggregates can be insoluble or soluble. Insoluble aggregates can be detected in various ways, for example: visualization by eye as particles in a composition; filtration through a filter, for example a 0.2 µM filter followed by detection on the filter using microscopic techniques; formation of a pellet in a tube following centrifugation; and measurement of turbidity in a composition using an ultraviolet spectrophotometer. Soluble aggregates can be detected, for example, gel electrophoretic techniques such as gel electrophoresis (SDS-PAGE or native gel), and by native size exclusion chromatography-high performance liquid chromatography (SEC-HPLC).

"Denaturation" refers to an alteration of the three-dimensional structure of a polypeptide. In certain instances, the alteration is such that a polypeptide is partially or completely unfolded. In certain instances, the alteration of three-dimensional structure is sufficient to cause a partial or complete loss of function. In certain instances, denaturation can be induced by exposure of a polypeptide to any one or more of the following: heat; pH extremes; organic solvents, including, but not limited to, alcohol and acetone; detergents, including, but not limited to, SDS; and chaotropic reagents, including, but not limited to, urea and guanidine hydrochloride. In certain instances, denaturation of certain polypeptides, for example, globular proteins, by exposure to organic solvents, urea, and detergents results in disruption of hydrophobic interactions within the polypeptide. In certain instances, denaturation of a polypeptide by exposure to, for example, pH extremes results in alteration of the net charge of the polypeptide, which causes electrostatic repulsion and disruption of certain hydrogen bonding within the polypeptide.

A "nonpolar amino acid" refers to an amino acid comprising one or more uncharged lipohilic side chains. In certain embodiments, a nonpolar amino acid is a natural amino acid. In certain embodiments, a nonpolar amino acid is a non-natural amino acid. Exemplary nonpolar amino acids include, but are not limited to, glycine, alanine, valine, leucine, isoleucine, proline, methionine, phenylalanine, and tryptophan. In certain embodiments, a nonpolar amino acid is a levorotatory (L-) amino acid. In certain embodiments, a nonpolar amino acid is a dextrorotatory (D-) amino acid. In certain embodiments, a nonpolar amino acid is a mixture of D- and L-isomers. In certain embodiments, a nonpolar amino acid is L-methionine. In certain embodiments, a nonpolar amino acid is L-alanine. In certain embodiments, a nonpolar amino acid is L-leucine.

A "basic amino acid" refers to an amino acid comprising one or more positively charged side chains at pH 7.0. In certain embodiments, a basic amino acid is a natural amino acid. In certain embodiments, a basic amino acid is a non-natural amino acid. Exemplary basic amino acids include, but are not limited to, lysine, arginine, and histidine. In certain embodiments, a basic amino acid is a levorotatory (L-) amino acid. In certain embodiments, a basic amino acid is a dextrorotatory (D-) amino acid. In certain embodiments, a basic amino acid is a mixture of D- and L-isomers. In certain embodiments, a basic amino acid is L-arginine. In certain embodiments, a basic amino acid is L-histidine.

The term "cryoprotectant" refers to an agent that stabilizes a specific binding agent to HGF in a composition during one or more cycles of freezing and thawing. In certain embodiments, such cycles are referred to as freeze/thaw cycles. In certain embodiments, the composition subjected to freezing is a solid. In certain embodiments, the composition subjected to freezing is not a solid. In certain embodiments, the composition subjected to freezing is at a temperature between −20° C. and −80° C. In certain embodiments, a specific binding agent to HGF in a composition comprising a cryoprotectant shows less aggregation when subjected to one or more cycles of freeze/thaw compared with the composition not comprising the cryoprotectant. Exemplary cryoprotectants include, but are not limited to, hydrophilic polymers, for example, including, but not limited to, polyvinylpyrrolidone K15, PEG 200, PEG 400, PEG 600, PEG 4000, PEG 8000, and PEG 30,000; alcohols, for example, including, but not limited to, ethanol, 2-propanol, propylene glycol, hexanediol, L-(+)-2,3-butanediol, and (±)2-methyl-2,4-pentanediol; sugars and polyols, including, but not limited to, glucose, mannose, sucrose, lactose, mannitol, xylitol, erythritol, threitol, sorbitol, inositol, glycerol, L-gluconate, trehalose, and raffinose; and basic amino acids, including, but not limited to lysine, arginine, and histidine. In certain embodiments, a cryoprotectant is polyvinylpyrrolidone K15. In certain embodiments, a cryoprotectant is PEG 200. In certain embodiments, a cryoprotectant is PEG 400. In certain embodiments, a cryoprotectant is PEG 600. In certain embodiments, a cryoprotectant is PEG 4000. In certain embodiments, a cryoprotectant is (±)2-methyl-2,4-pentanediol. In certain embodiments, a cryoprotectant is hexanediol. In certain embodiments, a cryoprotectant is propylene glycol. In certain embodiments, a cryoprotectant is 2-propanol. In certain embodiments, a cryoprotectant is ethanol. In certain embodiments, a cryoprotectant is L-(+)-2,3-butanediol. In certain embodiments, a cryoprotectant is sucrose. In certain embodiments, a cryoprotectant is erythritol. In certain embodiments, a cryoprotectant is xylitol. In certain embodiments, a cryoprotectant is inositol. In certain embodiments, a cryoprotectant is raffinose. In certain embodiments, a cryoprotectant is trehalose. In certain embodiments, a cryoprotectant is glucose In certain embodiments, a cryoprotectant is arginine. In certain embodiments, a cryoprotectant is histidine.

An agent "reduces discoloration" in a composition comprising a specific binding agent when the composition comprising the agent is more photostable upon storage at any point from 12 hours to 24 months compared with the composition not comprising the agent. In certain embodiments, the composition comprising the agent is more photostable upon storage at any point from 12 hours to 18 months, or at any point from 12 hours to 12 months, or at any point from 12 hours to six months, or at any point from 12 hours to one month, or at any point from 12 hours to 14 days, or at any point from 12 hours to seven days, or at any point from 12 hours to three days compared with the composition not comprising the agent. In certain embodiments, photostability is assessed at a temperature between 2° C. and 8° C. In certain such embodiments, photostability is assessed at 4° C. In certain embodiments, photostability is assessed at ambient temperature. In certain such embodiments, photostability is assessed at a temperature between 20° C. and 26° C. In certain embodiments, photostability is assessed at a temperature between −20° C. and −80° C. In certain embodiments, photostability is determined by assessing the effect of light wavelength, light intensity, and/or length of exposure to light on the color of the composition. In certain embodiments, reduction of discoloration is determined by visual inspection. In certain embodiments, reduction of discoloration is determined quantitatively by measuring absorbance of a composition. In certain embodiments, free L-methionine in a composition reduces discoloration. In certain embodiments, free L-methionine in a composition reduces discoloration by a process that includes reducing oxidation of methionine residues in a protein. In certain embodiments, free L-methionine in a composition reduces discoloration by a process that does not include reducing oxidation of methionine residues in a protein. In certain embodiments, one or more anti-oxidant compounds, other than free L-methionine, in a composition reduce discoloration. In certain embodiments, such anti-oxidant compounds are suitable for injection. Exemplary anti-oxidant compounds suitable for injection include, but are not limited to, glutathione, cysteine ascorbate, L-taurine, and riboflavin.

A "buffering agent" or "buffer" refers to an agent that maintains the pH of a composition within a desired range.

The term "HGF activity" includes any biological effect of HGF. In certain embodiments, HGF activity is Met-HGF activity. In certain embodiments, HGF activity is Met independent HGF activity.

The term "Met-HGF signaling" includes the interaction of HGF with a Met receptor.

The term "Met-HGF activity" includes any biological activity resulting from Met-HGF signaling. Exemplary activities include, but are not limited to, neural induction, liver regeneration, wound healing, growth, invasion, morphologic differentiation, embryological development, scattering, proliferation, apoptosis, cell motility, metastasis, migration, cell adhesion, integrin clustering, phosphorylation of paxillin, formation of focal adhesions, and cancer resulting from aberrant Met-HGF signaling.

The term "aberrant Met-HGF signaling" includes any circumstance in which Met-HGF signaling fails to stimulate any Met-HGF activity when normally signaling would result in such activity. Aberrant Met-HGF signaling also includes any circumstance in which Met-HGF signaling results in less Met-HGF activity than would occur with normal signaling. Aberrant activity also includes any circumstance in which Met-HGF signaling results in greater Met-HGF activity than would occur with normal signaling. Aberrant Met-HGF signaling can result, for example, in certain cancers.

The term "Met independent HGF activity" refers to any biological activity affected by HGF that does not depend on binding of HGF to a Met receptor. Such activity includes, but is not limited to, biological activity affected by HGF interaction with other receptors and biological activity affected by HGF through other pathways, e.g., Ron or met/ron heterodimers.

The term "aberrant HGF activity" refers to any circumstance in which HGF activity is either higher or lower than it should be. In certain circumstances, aberrant HGF activity results from aberrant HGF signaling. In certain circumstances, aberrant HGF activity results from a concentration of HGF that is higher than it should be. In certain embodiments, aberrant HGF activity results from a concentration of HGF that is lower than it should be.

A specific binding agent "substantially inhibits binding" of a ligand to a receptor when an excess of specific binding agent reduces the quantity of receptor bound to the ligand by at least about 20%, 40%, 60%, 80%, 85%, or more (as measured in an in vitro competitive binding assay). In certain embodiments, a specific binding agent is an antibody. In certain such embodiments, an antibody substantially inhibits binding of HGF to a c-Met receptor.

The term "cancer" includes, but is not limited to solid tumors and hematologic malignancies. Exemplary cancers include, but are not limited to, breast cancer, colorectal cancer, gastric carcinoma, glioma, head and neck squamous cell carcinoma, hereditary and sporadic papillary renal carcinoma, leukemia, lymphoma, Li-Fraumeni syndrome, malignant pleural mesothelioma, melanoma, multiple myeloma, non-small cell lung carcinoma, osteosarcoma, ovarian cancer, pancreatic cancer, prostate cancer, small cell lung cancer, synovial sarcoma, thyroid carcinoma, and transitional cell carcinoma of urinary bladder.

The term "pharmaceutical agent or drug" as used herein refers to a chemical compound or composition capable of inducing a desired therapeutic effect when properly administered to a patient. As used herein, a therapeutic effect may or may not include a prophylactic effect.

The term "modulator," as used herein, is a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules, Peptibodies are described in, e.g., U.S. Pat. No. 6,660,843 and PCT Publication No. WO01/83525.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolecular species present in the composition. In certain embodiments, the object species is purified to essential homogeneity (contaminant species cannot be detected in the composition by conventional detection methods) wherein the composition consists essentially of a single macromolecular species.

The term "patient" includes human and animal subjects.

Certain Exemplary Specific Binding Agents

In certain instances, HGF binds a Met receptor to induce Met phosphorylation. In certain instances, normal HGF-induced Met phosphorylation regulates a variety of cellular processes. In certain instances, aberrant Met-HGF activity correlates with a number of human disease states. For example, in certain instances, too much HGF activity correlates with certain cancers. Therefore, in certain instances, modulating HGF activity may be therapeutically useful. In certain embodiments, specific binding agents to HGF are used to decrease the amount of HGF activity from an abnormally high level. In certain embodiments, decreasing HGF activity from an abnormally high level decreases tumorigenic activity and reduces the severity of cancer. According to certain embodiments, specific binding agents to HGF are used to treat cancer. In certain embodiments, specific binding agents to HGF are used to prevent cancer.

In certain embodiments, a specific binding agent to HGF is used to treat cancers in which HGF activity is normal. In such cancers, for example, reduction of HGF activity to below normal may provide a therapeutic effect.

In certain embodiments, a specific binding agent to HGF is used to modulate at least one Met-HGF activity. In certain embodiments, a specific binding agent to HGF is used to modulate at least one Met independent HGF activity. In certain embodiments, more than one specific binding agent to HGF is used to modulate HGF activity.

In certain embodiments, specific binding agents to HGF are fully human monoclonal antibodies. In certain embodiments, nucleotide sequences encoding, and amino acid sequences comprising, heavy and light chain immunoglobulin molecules, particularly sequences corresponding to the variable regions are provided. In certain embodiments, sequences corresponding to complementarity determining regions (CDR's), specifically from CDR1 through CDR3, are provided. According to certain embodiments, a hybridoma cell line expressing such an immunoglobulin molecule is provided. According to certain embodiments, a hybridoma cell line expressing such a monoclonal antibody is provided. In certain embodiments a hybridoma cell line is selected from at least one of 1.24.1, 1.29.1, 1.60.1, 1.61.3, 1.74.3. 1.75.1, 2.4.4, 2.12.1, 2.40.1, and 3.10.1. In certain embodiments, a purified human monoclonal antibody to human HGF is provided.

Additional exemplary antibodies and methods of making and using such antibodies are described in U.S. Publication No. 2005/0118643, published Jun. 2, 2005. In certain such embodiments, a purified human monoclonal antibody to human HGF is provided, See, e.g., U.S. Publication No. 2005/0118643. In certain such embodiments, a purified human monoclonal antibody to human HGF is 2.12.1, discussed in the Examples below.

One can engineer mouse strains deficient in mouse antibody production with large fragments of the human Ig loci in anticipation that such mice would produce human antibodies in the absence of mouse antibodies. Large human Ig fragments may preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains may yield high affinity fully human antibodies against any antigen of interest, including human antigens. Using the hybridoma technology, antigen-specific human MAbs with the desired specificity may be produced and selected. Certain exemplary methods are described in WO 98/24893, U.S. Pat. No. 5,545,807, EP 546073B1, and EP 546073A1.

In certain embodiments, one may use constant regions from species other than human along with the human variable region(s). In certain embodiments, one may use constant regions from human along with variable region(s) from species other than human.

Certain Exemplary Antibody Structure

Naturally occurring antibody structural units typically comprise a tetramer. Each such tetramer typically is composed of two identical pairs of polypeptide chains, each pair having one full-length light chain (in certain embodiments, about 25 kDa) and one full-length heavy chain (in certain embodiments, about 50-70 kDa).

The amino-terminal portion of each chain typically includes a variable region ($V_H$ in the heavy chain and $V_L$ in the light chain) of about 100 to 110 or more amino acids that typically is responsible for antigen recognition. The carboxy-terminal portion of each chain typically defines a constant region ($C_H$ domains in the heavy chain and $C_L$ in the light chain) that may be responsible for effector function. Antibody effector functions include activation of complement and stimulation of opsonophagocytosis. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)). The variable regions of each light/heavy chain pair typically form the antigen binding site.

The variable regions typically exhibit the same general structure of relatively conserved framework regions (FR) joined by three hypervariable regions, also called complementarity determining regions or CDRs. The CDRs from the heavy and light chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

As discussed in the "Certain Definitions" section above, there are several types of antibody fragments. Exemplary antibody fragments include, but are not limited to, Fab fragment, Fab' fragment, F(ab')$_2$ molecule, Fv molecule, scFv, maxibody, and Fc fragment.

In certain embodiments, functional domains, $C_H1$, $C_H2$, $C_H3$, and intervening sequences can be shuffled to create a different antibody constant region. For example, in certain embodiments, such hybrid constant regions can be optimized for half-life in serum, for assembly and folding of the antibody tetramer, and/or for improved effector function. In certain embodiments, modified antibody constant regions may be produced by introducing single point mutations into the amino acid sequence of the constant region and testing the resulting antibody for improved qualities, e.g., one or more of those listed above.

In certain embodiments, an antibody of one isotype is converted to a different isotype by isotype switching without losing its specificity for a particular target molecule Methods of isotype switching include, but are not limited to, direct recombinant techniques (see e.g., U.S. Pat. No. 4,816,397) and cell-cell fusion techniques (see e.g., U.S. Pat. No. 5,916,771), among others. In certain embodiments, an antibody can be converted from one subclass to another subclass using techniques described above or otherwise known in the art without losing its specificity for a particular target molecule, including, but not limited to, conversion from an IgG2 subclass to an IgG1, IgG3, or IgG4 subclass.

Bispecific or Bifunctional Antibodies

A bispecific or bifunctional antibody typically is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann Clin. Exp. Immunol 79: 315-321 (1990), Kostelny et al. J. Immunol. 148:1547-1553 (1992), Certain Preparation of Antibodies In certain embodiments, antibodies can be expressed in cell lines other than hybridoma cell lines. In certain embodiments, sequences encoding particular antibodies, including chimeric antibodies, can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus or by transfecting a vector using procedures known in the art, as exemplified by U.S. Pat. Nos. 4,399,216; 4,912,040; 4,740,461; and 4,959,455.

In certain embodiments, an expression vector comprises one or more polynucleotide sequences discussed herein, including, but not limited to, polynucleotide sequences encoding one or more antibodies. In certain embodiments, a method of making a polypeptide comprising producing the polypeptide in a cell comprising any of the above expression vectors in conditions suitable to express the polynucleotide contained therein to produce the polypeptide is provided.

In certain embodiments, an expression vector expresses an antibody heavy chain. In certain embodiments, an expression vector expresses an antibody light chain. In certain embodiments, an expression vector expresses both an antibody heavy chain and an antibody light chain. In certain embodiments, a method of making an antibody comprising producing the antibody in a cell comprising at least one of expression vectors in conditions suitable to express the polynucleotides contained therein to produce the antibody is provided.

In certain embodiments, the transfection procedure used may depend upon the host to be transformed. Certain methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain mammalian cell lines available as hosts for expression are known in the art and include, but are not limited to, many immortalized cell lines available from the American Type Culture Collection (ATCC), including but not limited to Chinese hamster ovary (CHO) cells, E5 cells, HeLa cells, baby hamster kidney (BHK) cells, monkey kidney cells (COS), human hepatocellular carcinoma cells (e.g., Hep G2), NS0 cells, SP20 cells, Per C6 cells, 293 cells, and a number of other cell lines. In certain embodiments, cell lines may be selected through determining which cell lines have high expression levels and produce antibodies with constitutive antigen binding properties.

In certain embodiments, the vectors that may be transfected into a host cell comprise control sequences that are operably linked to a polynucleotide encoding an antibody. In certain embodiments, control sequences facilitate expression of the linked polynucleotide, thus resulting in the production of the polypeptide encoded by the linked polynucleotide. In certain embodiments, the vector also comprises polynucleotide sequences that allow chromosome-independent replication in the host cell. Exemplary vectors include, but are not limited to, plasmids (e.g., BlueScript, puc, etc.), cosmids, and YACS.

Certain Specific Binding Agent Compositions

In certain embodiments, a composition comprising a specific binding agent to HGF, at least one stabilizing agent, and a buffering agent is provided. In certain such embodiments, the composition further comprises at least one additional pharmaceutical agent.

In certain embodiments, the at least one specific binding agent to HGF is at a concentration of 0.5 mg/ml to 200 mg/ml. In certain such embodiments, the at least one specific binding agent to HGF is present at a concentration of 30 mg/ml. In certain embodiments, compositions will include more than one different specific binding agent to HGF. In certain such embodiments, the more than one specific binding agents to HGF bind more than one epitope.

In certain embodiments, the at least one stabilizing agent is a nonpolar amino acid. In certain embodiments, the nonpolar amino acid is present at a concentration of at least 0.01 M. In certain embodiments, the nonpolar amino acid is present at a concentration of 0.01 M to 0.2 M. Those ranges and any ranges discussed in this application include the endpoints and all values between the endpoints. In certain embodiments, a nonpolar amino acid is L-methionine, which is present at a concentration of 0.01 M. In certain embodiments, a nonpolar amino acid is L-alanine, which is present at a concentration of 0.02 M. In certain embodiments, a nonpolar amino acid is L-alanine, which is present at a concentration of 0.2 M. In certain embodiments, a nonpolar amino acid is L-leucine, which is present at a concentration of 0.02 M. In certain embodiments, a nonpolar amino acid is L-leucine, which is present at a concentration of 0.075 M.

In certain embodiments, the at least one stabilizing agent is a cryoprotectant. In certain embodiments, a cryoprotectant is present at a concentration of 0.01 M to 0.2 M. In certain embodiments, a cryoprotectant is polyvinylpyrrolidone K15, which is present at a concentration of 0.1 M. In certain embodiments, a cryoprotectant is PEG 200, which is present at a concentration of 0.1 M. In certain embodiments, a cryoprotectant is PEG 400, which is present at a concentration of 0.1 M. In certain embodiments, a cryoprotectant is PEG 600, which is present at a concentration of 0.1 M. In certain embodiments, a cryoprotectant is PEG 4000, which is present at a concentration of 0.1 M. In certain embodiments, a cryoprotectant is (±)2-methyl-2,4-pentanediol, which is present at a concentration of 0.1 M. In certain embodiments, a cryoprotectant is hexanediol, which is present at a concentration of 0.1 M. In certain embodiments, a cryoprotectant is propylene glycol, which is present at a concentration of 0.1 M. In certain embodiments, a cryoprotectant is 2-propanol, which is present at a concentration of 0.1 M. In certain embodiments, a cryoprotectant is ethanol, which is present at a concentration of 0.1 M. In certain embodiments, a cryoprotectant is L-(+)-2,3-butanediol, which is present at a concentration of 0.1 M. In certain embodiments, a cryoprotectant is sucrose, which is present at a concentration of 0.1 M. In certain embodiments, a cryoprotectant is erythritol, which is present at a concentration of 0.1 M. In certain embodiments, a cryoprotectant is xylitol, which is present at a concentration of 0.1 M. In certain embodiments, a cryoprotectant is inositol, which is present at a concentration of 0.1 M. In certain embodiments, a cryoprotectant is raffinose, which is present at a concentration of 0.1 M. In certain embodiments, a cryoprotectant is trehalose, which is present at a concentration of 0.1 M. In certain embodiments, a cryoprotectant is glucose, which is present at a concentration of 0.1 M. In certain embodiments, a cryoprotectant is arginine, which is present at a concentration of 0.1 M. In certain embodiments, a cryoprotectant is histidine, which is present at a concentration of 0.1 M.

In certain embodiments, the at least one stabilizing agent is at least one nonpolar amino acid and at least one cryoprotectant, In certain embodiments, the at least one nonpolar amino acid is L-alanine, which is present at a concentration of 0.2 M, and the cryoprotectant is polyvinylpyrrolidone K15, which is present at a concentration of 0.1 M. In certain embodiments, the at least one nonpolar amino acid is L-alanine, which is present at a concentration of 0.2 M, and the cryoprotectant is PEG 200, which is present at a concentration of 0.1 M. In certain embodiments, the at least one nonpolar amino acid is L-alanine, which is present at a concentration of 0.2 M, and the cryoprotectant is PEG 400, which is present at a concentration of 0.1 M. In certain embodiments, the at least one nonpolar amino acid is L-alanine, which is present at a concentration of 0.2 M, and the cryoprotectant is PEG 600, which is present at a concentration of 0.1 M. In certain embodiments, the at least one nonpolar amino acid is L-alanine, which is present at a concentration of 0.2 M, and the cryoprotectant is PEG 4000, which is present at a concentration of 0.1 M. In certain embodiments, the at least one nonpolar amino acid is L-alanine, which is present at a concentration of 0.2 M, and the cryoprotectant is (±)2-methyl-2,4-pentanediol, which is present at a concentration of 0.1 M. In certain embodiments, the at least one nonpolar amino acid is L-alanine, which is present at a concentration of 0.2 M, and the cryoprotectant is hexanediol, which is present at a concentration of 0.1 M. In certain embodiments, the at least one nonpolar amino acid is L-alanine, which is present at a concentration of 0.2 M, and the cryoprotectant is propylene glycol, which is present at a concentration of 0.1 M. In certain embodiments, the at least one nonpolar amino acid is L-alanine, which is present at a concentration of 0.2 M, and the cryoprotectant is 2-propanol, which is present at a concentration of 0.1 M. In certain embodiments, the at least one nonpolar amino acid is L-alanine, which is present at a concentration of 0.2 M, and the cryoprotectant is ethanol, which is present at a concentration of 0.1 M. In certain embodiments, the at least one nonpolar amino acid is L-alanine, which is present at a concentration of 0.2 M, and the cryoprotectant is L-(+)-2,3-butanediol, which is present at a concentration of 0.1 M. In certain embodiments, the at least one nonpolar amino acid is L-alanine, which is present at a concentration of 0.2 M, and the cryoprotectant is sucrose, which is present at a concentration of 0.1 M. In certain embodiments, the at least one nonpolar amino acid is L-alanine, which is present at a concentration of 0.2 M, and the cryoprotectant is erythritol, which is present at a concentration of 0.1 M. In certain embodiments, the at least one nonpolar amino acid is L-alanine, which is present at a concentration of 0.2 M, and the cryoprotectant is xylitol, which is present at a concentration of 0.1 M. In certain embodiments, the at least one nonpolar amino acid is L-alanine, which is present at a concentration of 0.2 M, and the cryoprotectant is inositol, which is present at a concentration of 0.1 M. In certain embodiments, the at least one nonpolar amino acid is L-alanine, which is present at a concentration of 0.2 M, and the cryoprotectant is raffinose, which is present at a concentration of 0.1 M. In certain embodiments, the at least one nonpolar amino acid is L-alanine, which is present at a concentration of 0.2 M, and the cryoprotectant is trehalose, which is present at a concentration of 0.1 M. In certain embodiments, the at least one nonpolar amino acid is L-alanine, which is present at a concentration of 0.2 M, and the cryoprotectant is glucose, which is present at a concentration of 0.1 M. In certain embodiments, the at least one nonpolar amino acid is L-alanine, which is present at a concentration of 0.2 M, and the cryoprotectant is arginine, which is present at a concentration of 0.1 M. In certain embodiments, the at least one nonpolar amino acid is L-alanine, which is present at a concentration of 0.2 M, and the cryoprotectant is histidine, which is present at a concentration of 0.1 M.

In certain embodiments, the at least one stabilizing agent is at least one nonpolar amino acid and at least one cryoprotectant. In certain embodiments, the at least one nonpolar amino acid is L-leucine, which is present at a concentration of 0.2 M, and the cryoprotectant is polyvinylpyrrolidone K15, which is present at a concentration of 0.1 M. In certain embodiments, the at least one nonpolar amino acid is L-leucine, which is present at a concentration of 0.2 M, and the cryoprotectant is PEG 200, which is present at a concentration of 0.1 M. In certain embodiments, the at least one nonpolar amino acid is L-leucine, which is present at a concentration of 0.2 M, and the cryoprotectant is PEG 400, which is present at a concentration of 0.1 M. In certain embodiments, the at least one nonpolar amino acid is L-leucine, which is present at a concentration of 0.2 M, and the cryoprotectant is PEG 600, which is present at a concentration of 0.1 M. In certain embodiments, the at least one nonpolar amino acid is L-leucine, which is present at a concentration of 0.2 M, and the cryoprotectant is PEG 4000, which is present at a concentration of 0.1 M. In certain embodiments, the at least one nonpolar amino acid is L-leucine, which is present at a concentration of 0.2 M, and the cryoprotectant is (±)2-methyl-2,4-pentanediol, which is present at a concentration of 0.1 M. In certain embodiments, the at least one nonpolar amino acid is L-leucine, which is present at a concentration of 0.2 M, and the cryoprotectant is hexanediol, which is present at a concentration of 0.1 M. In certain embodiments, the at least one nonpolar amino acid is L-leucine, which is present at a concentration of 0.2 M, and the cryoprotectant is propylene glycol, which is present at a concentration of 0.1 M. In certain embodiments, the at least one nonpolar amino acid is L-leucine, which is present at a concentration of 0.2 M, and the cryoprotectant is 2-propanol, which is present at a concentration of 0.1 M. In certain embodiments, the at least one nonpolar amino acid is L-leucine, which is present at a concentration of 0.2 M, and the cryoprotectant is ethanol, which is present at a concentration of 0.1 M. In certain embodiments, the at least one nonpolar amino acid is L-leucine, which is present at a concentration of 0.2 M, and the cryoprotectant is L-(+)-2,3-butanediol, which is present at a concentration of 0.1 M. In certain embodiments, the at least one nonpolar amino acid is L-leucine, which is present at a concentration of 0.2 M, and the cryoprotectant is sucrose, which is present at a concentration of 0.1 M. In certain embodiments, the at least one nonpolar amino acid is L-leucine, which is present at a concentration of 0.2 M, and the cryoprotectant is erythritol, which is present at a concentration of 0.1 M. In certain embodiments, the at least one nonpolar amino acid is L-leucine, which is present at a concentration of 0.2 M, and the cryoprotectant is xylitol, which is present at a concentration of 0.1 M. In certain embodiments, the at least one nonpolar amino acid is L-leucine, which is present at a concentration of 0.2 M, and the cryoprotectant is inositol, which is present at a concentration of 0.1 M. In certain embodiments, the at least one nonpolar amino acid is L-leucine, which is present at a concentration of 0.2 M, and the cryoprotectant is raffinose, which is present at a concentration of 0.1 M. In certain embodiments, the at least one nonpolar amino acid is L-leucine, which is present at a concentration of 0.2 M, and the cryoprotectant is trehalose, which is present at a concentration of 0.1 M. In certain embodiments, the at least one nonpolar amino acid is L-leucine, which is present at a concentration of 0.2 M, and the cryoprotectant is glucose, which is present at a concentration of 0.1 M. In certain embodiments, the at least one nonpolar amino acid is L-leucine, which is present at a concentration of 0.2 M, and the cryoprotectant is arginine, which is present at a concentration of 0.1 M. In certain embodiments, the at least one nonpolar amino acid is L-leucine, which is present at a concentration of 0.2 M, and the cryoprotectant is histidine, which is present at a concentration of 0.1 M.

In certain embodiments, the at least one stabilizing agent is at least one nonpolar amino acid and at least one cryoprotectant. In certain embodiments, the at least one stabilizing agent is a first nonpolar amino acid, a second nonpolar amino acid, and a cryoprotectant. In certain embodiments, the first nonpolar amino acid is L-alanine, which is present at a concentration of 0.2 M, the second nonpolar amino acid is L-leucine, which is present at a concentration of 0.07 M, and the cryoprotectant is polyvinylpyrrolidone K15, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is PEG 200, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is PEG 400, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is PEG 600, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is PEG 4000, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is (±)2-methyl-2,4-pentanediol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is hexanediol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is propylene glycol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is 2-propanol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is ethanol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is L-(+)-2,3-butanediol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is sucrose, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is erythritol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is xylitol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is inositol, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is raffinose, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is trehalose, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is glucose, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is arginine, which is present at a concentration of 0.1 M. In certain embodiments, the first nonpolar amino acid is L-alanine, which is present at a concentration of 0.2 M, the second nonpolar amino acid is L-leucine, which is present at a concentration of 0.07 M, and the cryoprotectant is histidine, which is present at a concentration of 0.1 M.

In certain embodiments, the pH of a composition comprising a buffering agent is above 5.4. In certain embodiments, the pH of a composition comprising a buffering agent is between 5.5 and 8.0. In certain embodiments, the pH is 5.6. In certain embodiments, the pH is 5.7. Exemplary buffering agents include, but are not limited to, acetate, histidine, phosphate, citrate, and propionate. In certain embodiments, the concentration of a buffering agent ranges from 1 mM to 50 mM. In certain embodiments, the concentration of the buffering agent is 10 mM.

In certain embodiments, the composition further comprises at least one sugar. As used herein, the term "sugar" refers to monosaccharides such as glucose and mannose, or polysaccharides including disaccharides such as sucrose and lactose, as well as sugar derivatives including sugar alcohols and sugar acids. Sugar alcohols include, but are not limited to, mannitol, xylitol, erythritol, threitol, sorbitol, inositol, and glycerol. A non-limiting example of a sugar acid is L-gluconate. Certain exemplary sugars include, but are not limited to, trehalose and raffinose. In certain embodiments, a sugar is provided at a concentration between 0.01 M and 0.3 M. In certain embodiments, a sugar is provided at a concentration of 0.1 M. Exemplary sugars include, but are not limited to, sucrose, glucose, trehalose, and xylitol. In certain embodiments, a sugar is provided at a concentration between 2% and 9.5%. In certain embodiments, a sugar is 2.6% glycerol. In certain embodiments, a sugar is 5.0% sorbitol. In certain embodiments, a sugar is 9.25% sucrose. In certain embodiments, a sugar is 9.0% sucrose.

In certain embodiments, the composition further comprises at least one alcohol. As used herein, the term "alcohol" refers to any compound of the general formula ROH, where R is any alkyl group or any substituted alkyl group. Alcohols include, but are not limited to, methanol, ethanol, 2-propanol, propylene glycol, hexanediol, L-(+)-2,3-butanediol, and (±)2-methyl-2,4-pentanediol. In certain embodiments, an alcohol is provided at a concentration between 0.01 M and 0.3 M. In certain embodiments, an alcohol is provided at a concentration of 0.1 M. Exemplary alcohols include, but are not limited to, methanol, ethanol, 2-propanol, propylene glycol, hexanediol, L-(+)-2,3-butanediol, and (±)2-methyl-2,4-pentanediol.

In certain embodiments, the composition further comprises at least one surfactant. As used herein, the term "surfactant" refers to a surface-active agent comprising a hydrophobic portion and a hydrophilic portion. Examples of surfactants include, but are not limited to, detergents and bile acid salts. In certain instances, surfactants are categorized as anionic, nonionic, zwitterionic, or cationic, depending on whether they comprise one or more charged group. Nonionic surfactants contain non-charged polar groups and have no charge. Certain exemplary nonionic surfactants include, but are not limited to, polyethylene glycol (PEG), including, but not limited to, PEG 200, PEG 400, PEG 600, PEG 4000, PEG 8000, and PEG 30,000; and polysorbate, including but not limited to, polysorbate 80 and polysorbate 20. In certain embodiments, the surfactant is provided at a concentration between 0.001% and 1.0%. In certain embodiments, the surfactant is provided at a concentration between 0.003% and 0.3%. In certain embodiments, the surfactant is provided at a concentration of 0.004%. In certain embodiments, the surfactant is provided at a concentration of 0.25%.

In certain embodiments, a composition comprising at least one specific binding agent to HGF, at least one stabilizing agent, and a buffering agent provides stabilization of a specific binding agent to HGF. In certain embodiments, the composition provides stabilization with respect to formation of fewer aggregates and/or dimers. In certain embodiments, the composition provides stabilization with respect to formation of fewer aggregates and/or dimers when subjected to one or more freeze/thaw cycles. In certain embodiments, the composition provides stabilization with respect to formation of fewer chemically altered forms. In certain embodiments, the composition provides reduced discoloration. In certain embodiments, reduced discoloration is determined by visual examination of color and/or clarity. In certain embodiments, reduced discoloration is determined by spectrophotometric measurement.

In certain embodiments, the presence and degree of aggregation and/or chemically altered forms of a particular protein molecule in a sample can be determined by suitable methods known in the art, such as size exclusion chromatography (SEC), for example, also known as gel filtration chromatography or molecular sieving chromatography. In certain embodiments, a suitable method for determining the presence of aggregates and/or chemically altered forms in a sample is gel electrophoresis under non-denaturing conditions. The "gel" refers to a matrix of water and a polymer such as agarose or polymerized acrylamide. These methods separate molecules on the basis of the size of the molecule compared to the size of the pores of the gel. Certain other methods of measuring aggregation and/or chemically altered forms include, but are not limited to, hydrophobic interaction chromatography (HIC) and high performance liquid chromatography (HPLC). HIC separates native proteins on the basis of their surface hydrophobicity between the hydrophobic moieties of the protein and insoluble, immobilized hydrophobic groups on the matrix. Generally, the protein preparation in a high salt buffer is loaded on the HIC column. The salt in the buffer interacts with water molecules to reduce the salvation of the proteins in solution, thereby exposing hydrophobic regions in the protein which are then adsorbed by the hydrophobic groups on the matrix. The more hydrophobic the molecule, the less salt is needed to promote binding. Usually, a decreasing salt gradient is used to elute proteins from a column. As the ionic strength decreases, the exposure of the hydrophilic regions of the protein increases and proteins elute from the column in order of increasing hydrophobicity. See, for example, Protein Purification, 2d Ed., Springer-Verlag, New York, 176-179 (1988). HPLC provides a separation based on any one of adsorption, ion exchange, size exclusion, HIC, or reverse phase chromatography. In certain embodiments, the separations are improved through the use of high-resolution columns and decreased column retention times. See, for example, Chicz et al., Methods in Enzymology 182, pp. 392-421 (1990). Additional exemplary methods for monitoring protein stability are found in Lee, V., ed. *Peptide and Protein Drug Delivery* (Marcel Dekker, Inc., New York, N.Y., 1991). In certain embodiments, protein stability is measured at a certain temperature for a certain period of time. In certain embodiments, a specific binding agent to HGF is stabilized in a composition stored at room temperature (25° C.) for at least 1 month to 6 months. Exemplary storage periods include, but are not limited to, at least 1 month, at least 3 months, and at least 6 months. In certain embodiments, a specific binding agent to HGF is stabilized in a composition stored between 2° C. and 8° C. for at least 6 months to 24 months. Exemplary storage periods include, but are not limited to, at least 6 months, at least 9 months, at least 12 months, at least 18 months, and at least 24 months. In certain embodiments, a specific binding agent to HGF is stabilized in a composition stored between −20° C. and −80° C. for at least 6 months to 24 months. Exemplary storage periods include, but are not limited to, at least 6 months, at least 9 months, at least 12 months, at least 18 months, and at least 24 months. In certain embodiments, a specific binding agent to HGF is stabilized in a composition stored between −20° C. and −80° C. for at least 6 months to 24 months, and then thawed. Exemplary storage periods include, but are not limited to, at least 6 months, at least 9 months, at least 12 months, at least 18 months, and at least 24 months.

In certain embodiments, a specific binding agent to HGF is prepared, purified, and formulated as a liquid pharmaceutical composition. In certain embodiments, after preparation and purification, a specific binding agent to HGF is stored prior to formulation. In certain such embodiments, the specific binding agent to HGF subjected to freezing, for example, at −20° C. or lower. In certain such embodiments, the specific binding agent to HGF is thawed at room temperature for further formulation. In certain embodiments, a liquid pharmaceutical formulation comprises a therapeutically effective amount a specific binding agent to HGF. In certain embodiments, the amount of specific binding agent to HGF to formulate in a formulation will be determined by one skilled in the art, depending upon, for example, the route of administration and desired dose volume. In certain embodiments, the pharmaceutical formulation comprises a specific binding agent to HGF at a concentration of 0.5 mg/ml to 200 mg/ml. In certain embodiments, a pharmaceutical formulation comprises a therapeutically effective amount a specific binding agent to HGF and a buffer that maintains the pH of the formulation above 5.4. In certain embodiments, a buffer maintains the pH of the formulation between 5.4 and 8.0. That range and any ranges discussed in this application include the endpoints and all values between the endpoints.

In certain embodiments, a liquid pharmaceutical formulation is lyophilized. Certain methods for lyophilizing liquid compositions are known to those skilled in the art. In certain embodiments, the composition is reconstituted with a sterile diluent just prior to use. Exemplary sterile diluents include, but are not limited to, Ringer's solution, distilled water, and sterile saline. In certain embodiments, the composition is administered to patients upon reconstitution using methods known to those skilled in the art.

In certain embodiments, specific binding agents including, but not limited to, antibodies, which bind to a particular protein and block interaction with other binding compounds may have therapeutic use. In this application, when discussing the use of antibodies to treat diseases or conditions, such use may include use of compositions comprising antibodies; and/or combination therapies comprising antibodies and one or more additional active ingredients. When antibodies are used to "treat" a disease or condition, such treatment may or may not include prevention of the disease or condition.

In certain embodiments, a specific binding agent including, but not limited to, an antibody, is administered alone. In certain embodiments, an antibody is administered prior to the administration of at least one other therapeutic agent. In certain embodiments, an antibody is administered concurrent with the administration of at least one other therapeutic agent. In certain embodiments, an antibody is administered subsequent to the administration of at least one other therapeutic agent. Exemplary therapeutic agents, include, but are not limited to, at least one cancer therapy agent. Exemplary cancer therapy agents include, but are not limited to, radiation therapy and chemotherapy.

In certain embodiments, pharmaceutical compositions comprising specific binding agents, e.g., antibodies, can be administered in combination therapy, i.e., combined with other agents. Exemplary agents include, but are not limited to, in vitro synthetically prepared chemical compositions, antibodies, antigen binding regions, radionuclides, and combinations and conjugates thereof. In certain embodiments, an agent may act as an agonist, antagonist, allosteric modulator, or toxin. In certain embodiments, an agent may act to inhibit or stimulate its target (e.g., receptor or enzyme activation or inhibition), and thereby promote cell death or arrest cell growth. In certain embodiments, the combination therapy comprises a specific binding agent to HGF, in combination with at least one anti-angiogenic agent.

Exemplary chemotherapy treatments include, but are not limited to anti-neoplastic agents including, but not limited to, alkylating agents including, but not limited to: nitrogen mustards; nitrosoureas; ethylenimines/methylmelamine; alkyl sulfonates; antimetabolites; pyrimidine analogs; purine analogs; natural products, including, but not limited to, antimitotic drugs, vinca alkaloids, podophyllotoxins; antibiotics; enzymes; biological response modifiers; miscellaneous agents, including, but not limited to, platinum coordination complexes; anthracenediones; substituted urea; methylhydrazine derivatives; adrenocortical suppressants; hormones and antagonists.

Exemplary cancer therapies, which may be administered with a specific binding agent to HGF, also include, but are not limited to, targeted therapies. Examples of targeted therapies include, but are not limited to, use of therapeutic antibodies. Exemplary therapeutic antibodies, include, but are not limited to, mouse, mouse-human chimeric, CDR-grafted, humanized and fully human antibodies, and synthetic antibodies, including, but not limited to, those selected by screening antibody libraries. Exemplary antibodies include, but are not limited to, those which bind to cell surface proteins Her2, CDC20, CDC33, mucin-like glycoprotein, and epidermal growth factor receptor (EGFR) present on tumor cells, and optionally induce a cytostatic and/or cytotoxic effect on tumor cells displaying these proteins.

In certain embodiments, cancer therapy agents are anti-angiogenic agents which decrease angiogenesis. In certain embodiments, cancer therapy agents are angiogenesis inhibitors.

In certain embodiments, a specific binding agent to HGF may be administered prior to, concurrent with, and subsequent to treatment with a cancer therapy agent. In certain embodiments, a specific binding agent to HGF may be administered prophylactically to prevent or mitigate the onset of bone loss by metastatic cancer. In certain embodiments, a specific binding agent to HGF may be administered for the treatment of an existing condition of bone loss due to metastasis.

Exemplary cancers include, but are not limited to, breast cancer, colorectal cancer, gastric carcinoma, glioma, head and neck squamous cell carcinoma, hereditary and sporadic papillary renal carcinoma, leukemia, lymphoma, Li-Fraumeni syndrome, malignant pleural mesothelioma, melanoma, multiple myeloma, non-small cell lung carcinoma, osteosarcoma, ovarian cancer, pancreatic cancer, prostate cancer, small cell lung cancer, synovial sarcoma, thyroid carcinoma, and transitional cell carcinoma of urinary bladder.

In certain embodiments, a specific binding agent to HGF may be used alone or with at least one additional therapeutic agent for the treatment of cancer. In certain embodiments, a specific binding agent to HGF is used in conjunction with a therapeutically effective amount of an additional therapeutic agent.

In certain embodiments, a specific binding agent to HGF is used with one or more particular therapeutic agents to treat various cancers. In certain embodiments, a specific binding agent to HGF is used with one or more particular therapeutic agents to treat or prevent malaria. In certain embodiments, a specific binding agent to HGF is used with one or more particular therapeutic agents to treat or prevent proliferative diabetic retinopathy. In certain embodiments, in view of the condition and the desired level of treatment, two, three, or more agents may be administered. In certain embodiments, such agents may be provided together by inclusion in the same formulation. In certain embodiments, such agents and a specific binding agent to HGF may be provided together by inclusion in the same formulation. In certain embodiments, such agents may be formulated separately and provided together by inclusion in a treatment kit. In certain embodiments, such agents and a specific binding agent to HGF may be formulated separately and provided together by inclusion in a treatment kit. In certain embodiments, such agents may be provided separately. In certain embodiments, when administered by gene therapy, the genes encoding protein agents and/or a specific binding agent to HGF may be included in the same vector. In certain embodiments, the genes encoding protein agents and/or a specific binding agent to HGF may be under the control of the same promoter region. In certain embodiments, the genes encoding protein agents and/or a specific binding agent to HGF may be in separate vectors.

It is understood that the response by individual patients to the aforementioned medications or combination therapies may vary, and an appropriate efficacious combination of drugs for each patient may be determined by his or her physician.

In certain embodiments, pharmaceutical compositions comprising a specific binding agent to HGF together with a pharmaceutically acceptable diluent, carrier, solubilizer, emulsifier, preservative and/or adjuvant are provided.

In certain embodiments, pharmaceutical compositions comprising a specific binding agent to HGF and a therapeutically effective amount of at least one additional therapeutic agent, together with a pharmaceutically acceptable diluent, carrier, solubilizer, emulsifier, preservative and/or adjuvant are provided.

In certain embodiments, therapies comprising a specific binding agent to HGF and at least one serine protease inhibitor, and methods of treatment using such therapies are provided. In certain embodiments, a therapy comprises a specific binding agent to HGF, a serine protease inhibitor, and at least one additional agent described herein.

In certain instances, a disturbance of the protease/protease inhibitor balance can lead to protease-mediated tissue destruction, including, but not limited to, tumor invasion of normal tissue leading to metastasis.

In certain embodiments, a specific binding agent to HGF may be used with at least one therapeutic agent for inflammation. In certain embodiments, a specific binding agent to HGF may be used with at least one therapeutic agent for an immune disorder. Certain exemplary therapeutic agents for inflammation are described, e.g., in C. A. Dinarello and L. L. Moldawer *Proinflammatory and Anti-Inflammatory Cytokines in Rheumatoid Arthritis: A Primer for Clinicians* Third Edition (2001) Amgen. Inc. Thousand Oaks, Calif.

In certain embodiments, pharmaceutical compositions include more than one different specific binding agent to HGF. In certain such embodiments, the more than one specific binding agents to HGF bind more than one epitope.

In certain embodiments, liquid, lyophylized, or spray-dried compositions comprising one or more specific binding agent to HGF are prepared as aqueous or nonaqueous solutions or suspensions for subsequent administration to a patient.

In certain embodiments, materials for compositions are nontoxic to recipients at the dosages and concentrations employed.

In certain embodiments, the pharmaceutical composition contains formulation materials for modifying, maintaining or preserving, for example, the pH, osmolarity, viscosity, clarity, color, isotonicity, odor, sterility, stability, rate of dissolution or release, adsorption or penetration of the composition. Exemplary formulation materials include, but are not limited to, oils, vitamins, salts, amino acids (including, but not limited to, carnitine and betaine), nonpolar amino acids (including, but not limited to, glycine, alanine, valine, leucine, isoleucine, proline, methionine, phenylalanine, and tryptophan); basic amino acids (including, but not limited to, lysine, arginine, and histidine) antimicrobials; antioxidants (including, but not limited to, ascorbic acid, sodium sulfite and sodium hydrogen-sulfite); buffers (including, but not limited to, acetate, histidine, phosphate, citrate, and propionate); bulking agents (including, but not limited to, mannitol and glycine); chelating agents (including, but not limited to, ethylenediamine tetraacetic acid (EDTA)); complexing agents (including, but not limited to, caffeine, polyvinylpyrrolidone, beta-cyclodextrin and hydroxypropyl-beta-cyclodextrin); fillers; sugar or sugar alcohols (including, but not limited to, monosaccharides, disaccharides, polysaccharides, and water soluble glycans); other carbohydrates, for example, saccharides or glucans (including, but not limited to, fructose, glucose, mannose, sorbose, xylose, maltose, sucrose, lactose, dextran, pullulan, dextrin, $\alpha$ and $\beta$ cyclodextrin, soluble starch, hydroxyethyl starch, carboxymethylcellulose, and mixtures thereof); sugar alcohols (including, but not limited to, mannitol, erythritol, xylitol, inositol, and sorbitol); proteins (including, but not limited to, serum albumin, gelatin and immunoglobulins); coloring, flavoring and diluting agents; emulsifying agents; hydrophilic polymers (including, but not limited to, polyvinylpyrrolidone, including, but not limited to, polyvinylpyrrolidone with an average molecular weight between 2,000 and 3,000, polyvinylpyrrolidone with an average molecular weight of 10,0001 and polyethylene glycol, including, but not limited to, polyethylene glycol with an average molecular weight between 200 and 600, polyethylene glycol with an average molecular weight between 3,000 and 5,000, polyethylene glycol with an average molecular weight between 4,000 and 8,000, and polyethylene glycol with an average molecular weight of 30,000); low molecular weight polypeptides, salt-forming counterions (including, but not limited to, sodium); preservatives (including, but not limited to, benzalkonium chloride, benzoic acid, salicylic acid, thimerosal, phenethyl alcohol, methylparaben, propylparaben, chlorhexidine, sorbic acid and hydrogen peroxide); solvents (including, but not limited to, glycerin and propylene glycol); suspending agents; surfactants or wetting agents (including, but not limited to, pluronics, PEG, sorbitan esters, polysorbates including, but not limited to, polysorbate 20, polysorbate 80, triton, tromethamine, lecithin, cholesterol, and tyloxapol); stabilizing agents (including, but not limited to, nonpolar amino acids, polyethylene glycol, polyvinylpyrrolidone, alcohols, sugar alcohols, and basic amino acids); tonicity enhancing agents (including, but not limited to, alkali metal halides, for example, sodium chloride and potassium chloride; sugars, including, but not limited to, mannitol and sorbitol); delivery vehicles; diluents; excipients and pharmaceutical adjuvants. (*Remington's Pharmaceutical Sciences*, 18th Edition, A. R. Gennaro, ed., Mack Publishing Company (1990).

In certain embodiments, a specific binding agent to HGF and/or a therapeutic molecule is linked to a half-life extending vehicle known in the art. Such vehicles include, but are not limited to, the Fc domain, polyethylene glycol (PEG), polyoxyethylated polyols, and dextran. Such vehicles and methods are described, e.g., in U.S. Pat. Nos. 4,179,337; 4,495,285; 4,609,546; 4,766,106; 6,660,843; and published PCT Application No. WO 99/25044. In certain instances, PEG is soluble in water at room temperature and has the general formula: R(O—CH$_2$—CH$_2$)$_n$O—R where R is hydrogen, or a protective group, including, but not limited to, an alkyl or alkanol group, and where "n" is a positive integer. In certain embodiments, the protective group has between 1 and 8 carbons. In certain such embodiments, the protective group is methyl. In certain embodiments, "n" is between 1 and 1,000. In certain embodiments, PEG has an average molecular weight between 1,000 and 40,000. Those ranges and any ranges discussed in this application include the endpoints and all values between the endpoints. In certain embodiments, PEG has at least one hydroxy group. In certain such embodiments, the hydroxy group is a terminal hydroxy group. In certain such embodiments, the terminal hydroxy group is activated by N-hydroxysuccinimide to react with a free amino group on a specific binding agent to HGF to form a covalently conjugated molecule. In certain embodiments, the type and amount of the reactive groups may be varied to a achieve a covalently conjugated PEG/specific binding agent to HGF. Preparation of conjugated PEG molecules is within the skill of the art.

In certain embodiments, a half-life extending vehicle is polyoxyethylated polyol. Exemplary polyoxyethylated polyols include, but are not limited to, polyoxyethylated sorbitol, polyoxyethylated glucose, and polyoxyethylated glycerol (POG). In certain embodiments, POG has an average molecular weight between 1,000 and 40,000. That range and any ranges discussed in this application include the endpoints and all values between the endpoints. Certain exemplary structures of POG are found, for example, in Knauf et al., *J. Biol. Chem.* 263:15064-15070 (1988). Certain exemplary POG conjugates are found, for example, in U.S. Pat. No. 4,766,106.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antibodies of the invention.

In certain embodiments, the primary vehicle or carrier in a pharmaceutical composition is aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, the vehicle or carrier is sterile. In certain embodiments, additional components are included. Exemplary additional components include, but are not limited to, fixed oils; polyethylene glycols; glycerin; propylene glycol and other synthetic solvents; antibacterial agents including, but not limited to, benzyl alcohol and methyl parabens; antioxidants including, but not limited to, ascorbic acid and sodium bisulfite; and chelating agents including, but not limited to ethylenediaminetetraacetic acid.

In certain embodiments, neutral buffered saline or saline mixed with serum albumin are further exemplary vehicles. In certain embodiments, pharmaceutical compositions comprise Tris buffer of about pH 7.0-8.5, or acetate buffer above pH 5.4, which may further include sorbitol or a suitable substitute therefore. In certain embodiments, a composition comprising a specific binding agent to HGF, with or without at least one additional therapeutic agents, may be prepared for storage by mixing the selected composition having the desired degree of purity with optional formulation agents (*Remington's Pharmaceutical Sciences*, supra) in the form of an aqueous solution. In certain embodiments, a pharmaceutical composition is enclosed in a container. Exemplary containers include, but are not limited to, an ampoule, disposable syringe, and multiple dose vial made of glass or plastic.

In certain embodiments, pharmaceutical compositions can be selected for parenteral delivery. Exemplary parenteral delivery includes, but is not limited to, intravenous, intramuscular, intradermal, or subcutaneous administration. In certain embodiments, the compositions may be selected for delivery through the digestive tract, such as orally. The preparation of such pharmaceutically acceptable compositions is within the skill of the art.

In certain embodiments, the formulation components are present in concentrations that are acceptable to the site of administration. In certain embodiments, a pharmaceutical composition comprises a therapeutically effective amount a specific binding agent to HGF and a buffer. In certain embodiments, buffers are used to maintain the composition at physiological pH or at a slightly lower pH. In certain embodiments, buffers are above pH 5.4. In certain embodiments, buffers are between pH 5.5 and pH 8.0. Exemplary buffers include, but are not limited to, acids and/or salts thereof, including, but not limited to, succinic acid or succinate, citric acid or citrate, acetic acid or acetate, tartaric acid or tartarate, phosphoric acid or phosphate, propionic acid or propionate, gluconic acid or gluconate, glutamic acid or glutamate, histidine, glycine, aspartic acid or aspartate, maleic acid or maleate, and malic acid or malate buffers. In certain instances, a "salt" refers to an electrically-neutral substance formed between an anion of an acid and an oppositely charged ion. In certain such instances, the oppositely charged ion is referred to as a "counterion." Exemplary counterions include, but are not limited to, sodium, potassium, ammonium, calcium, and magnesium. In certain embodiments, the concentration of buffer in a formulation is between 1 mM and 50 mM. In certain embodiments, the concentration of buffer in a formulation is between 5 mM and 30 mM. In certain embodiments, the concentration of buffer in a formulation is between 10 mM and 20 mM. Those ranges and any ranges discussed in this application include the endpoints and all values between the endpoints. In certain embodiments, the concentration of buffer in a formulation is 10 mM.

In certain embodiments, the pharmaceutical formulation comprises a specific binding agent to HGF at a concentration of 0.5 mg/ml to 200 mg/ml and a buffer. In certain embodiments, the buffer is at a concentration between 1 mM and 50 mM, and the pH of the formulation is above 5.4. In certain such embodiments, the pharmaceutical formulation comprises a specific binding agent to HGF at a concentration of 30 mg/ml and a buffer at a concentration of 10 mM, and the pH of the formulation is 5.7. In certain embodiments, the pharmaceutical formulation comprises a specific binding agent to HGF at a concentration of 30 mg/ml and a buffer at a concentration of 10 mM, and the pH of the formulation is 5.6.

In certain embodiments, a pharmaceutical formulation comprises a therapeutically effective amount a specific binding agent to HGF and a buffer. Exemplary buffers include, but are not limited to, histidine buffer, propionate buffer, and acetate buffer, at a concentration that maintains the pH of the formulation above 5.4. In certain embodiments, the pH of the formulation is between 5.5 and 8.0. The term "histidine buffer" refers to a buffer comprising a salt of histidine. The term "propionate buffer" refers to a buffer comprising a salt of propionic acid. In certain embodiments, the propionate counterion is sodium. In certain such embodiments, the buffer is sodium propionate. Other exemplary counterions include, but are not limited to, potassium, ammonium, calcium, and magnesium. The term "acetate buffer" refers to a buffer comprising a salt of acetic acid. In certain embodiments, the acetate counterion is sodium. In certain such embodiments, the buffer is sodium acetate. Other exemplary counterions include, but are not limited to, potassium, ammonium, calcium, and magnesium. In certain embodiments, the concentration of the buffer in the formulation is between 1 mM and 50 mM. In certain embodiments, the concentration of the buffer in the formulation is between 5 mM and 30 mM. In certain embodiments, the concentration of the buffer in the formulation is between 10 mM and 20 mM. Those ranges and any ranges discussed in this application include the endpoints and all values between the endpoints. In certain embodiments, the buffer is histidine, which is present at a concentration of 10 mM. In certain embodiments, the buffer is propionate, which is present at a concentration of 10 mM. In certain embodiments, the buffer is acetate, which is present at a concentration of 10 mM. In certain embodiments, the pharmaceutical formulation comprises a specific binding agent to HGF at a concentration of 0.5 mg/ml to 200 mg/ml and a buffer. Exemplary buffers include, but are not limited to, histidine buffer, propionate buffer, and acetate buffer, at a concentration between 1 mM and 50 mM, and the pH of the formulation is above 5.4. In certain embodiments, the pharmaceutical formulation comprises a specific binding agent to HGF at a concentration of 30 mg/ml, histidine buffer at a concentration of 10 mM, and the pH of the formulation is 5.7. In certain embodiments, the pharmaceutical formulation comprises a specific binding agent to HGF at a concentration of 30 mg/ml, propionate buffer at a concentration of 10 mM, and the pH of the formulation is 5.7. In certain embodiments, the pharmaceutical formulation comprises a specific binding agent to HGF at a concentration of 30 mg/ml, acetate buffer at a concentration of 10 mM, and the pH of the formulation is 5.7. In certain embodiments, the pharmaceutical formulation comprises a specific binding agent to HGF at a concentration of 30 mg/ml, histidine buffer at a concentration of 10 mM, and the pH of the formulation is 5.6. In certain embodiments, the pharmaceutical formulation comprises a specific binding agent to HGF at a concentration of 30 mg/ml, propionate buffer at a concentration of 10 mM, and the pH of the formulation is 5.6. In certain embodiments, the pharmaceutical formulation comprises a specific binding agent to HGF at a concentration of 30 mg/ml, acetate buffer at a concentration of 10 mM, and the pH of the formulation is 5.6.

In certain embodiments, a pharmaceutical formulation comprises a therapeutically effective amount of a specific binding agent to HGF; a buffer at a concentration that maintains the pH of the formulation above pH 5.4; and an amount of an isotonizing agent sufficient to provide a formulation that is isotonic. Exemplary buffers include, but are not limited to, histidine buffer, propionate buffer, and acetate buffer. A formulation that is "isotonic" has an osmolarity between 270 mOsm and 370 mOsm. In certain embodiments, the pH of the formulation is between 5.5 and 8.0. Certain methods of determining the isotonicity of a solution are within the knowledge of those skilled in the art. See, e.g., Setnikar et al., *J. Am. Pharm. Assoc.* 48:628-30 (1959). Exemplary isotonizing agents include, but are not limited to, sodium chloride; amino acids, including, but not limited to, alanine, valine, and glycine; sugars and sugar alcohols (polyols), including, but not limited to, glucose, dextrose, fructose, sucrose, maltose, mannitol, trehalose, glycerol, sorbitol, and xylitol; acetic acid, other organic acids or their salts, and relatively minor amounts of citrates or phosphates. In certain embodiments, the isotonizing agent is sorbitol. In certain such embodiments, sorbitol is provided at a concentration of at least 5%.

In certain embodiments, a pharmaceutical formulation comprises a therapeutically effective amount a specific binding agent to HGF; a buffer at a concentration that maintains the pH of the formulation above 5.4; and a surfactant. Exemplary buffers include, but are not limited to, histidine buffer, propionate buffer, and acetate buffer. In certain embodiments, the pH of the formulation is between 5.5 and 8.0. In certain embodiments, the surfactant is a nonionic surfactant. Certain exemplary nonionic surfactants include, but are not limited to, polyoxyethylene sorbital esters (polysorbates), polyoxypropylene-polyoxyethylene esters (pluronics), polyoxyethylene alcohols, simethicone, polyethylene glycols, lysophosphatidylcholine, and polyoxyethylene-p-t-octylphenols. Certain exemplary surfactants include, but are not limited to, PEG 200, PEG 400, PEG 600, PEG 4000, PEG 8000, PEG 30,000, polysorbate 80, and polysorbate 20. In certain embodiments, the surfactant is provided at a concentration between 0.001% and 1.0%. In certain embodiments, the surfactant is provided at a concentration between 0.003% and 0.3%. In certain embodiments, the surfactant is provided at a concentration of 0.004%. Those ranges and any ranges discussed in this application include the endpoints and all values between the endpoints. In certain embodiments, the surfactant is provided at a concentration of 0.25%.

In certain embodiments, when parenteral administration is contemplated, a therapeutic composition may be in the form of a pyrogen-free, parenterally acceptable aqueous solution comprising a desired specific binding agent to HGF, with or without additional therapeutic agents, in a pharmaceutically acceptable vehicle. In certain embodiments, a vehicle for parenteral injection is sterile distilled water in which a specific binding agent to HGF, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

Additional pharmaceutical compositions will be evident to those skilled in the art, including formulations involving specific binding agents to HGF, with or without at least one additional therapeutic agents, in sustained- or controlled-delivery formulations. In certain embodiments, techniques for formulating a variety of other sustained- or controlled-delivery vehicles, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices may include polyesters, hydrogels, polylactides (U.S. Pat. No. 3,773,919 and EP 058, 481), copolymers of L-glutamic acid and gamma ethyl-L-glutamate (Sidman et al., *Biopolymers*, 22:547-556 (1983)), poly(2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra) or poly-D(–)-3-hydroxybutyric acid (EP 133,988). In certain embodiments, sustained release compositions may also include liposomes, which can be prepared by any of several methods known in the art. See, e.g., Gabizon et al, *Cancer Research* 42:4734-4739 (1982); Eppstein et al., *Proc. Natl. Acad. Sci. USA,* 82:3688-3692 (1985); Szoka et al., *Ann. Rev. Biophys. Eng.* 9:467-508 (1980); EP 036,676; EP 088, 046 and EP 143,949. In certain embodiments, drug delivery systems known in the art are used. Such drug delivery systems are described in, for example, Poznansky et al., *Drug Delivery Systems*, R. L. Juliano, ed., Oxford, N.Y., pp. 253-315 (1980); Poznansky et al., *Pharmacol Rev.* 36:277-336 (1984).

The pharmaceutical composition to be used for in vivo administration typically is sterile. In certain embodiments, this may be accomplished by filtration through sterile filtration membranes. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution. In certain embodiments, such formulations may be stored either in a ready-to-use form or in a form (e.g., concentrated) that is diluted prior to administration.

In certain embodiments, the effective amount of a pharmaceutical composition comprising a specific binding agent to HGF, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a specific binding agent to HGF, with or without at least one additional therapeutic agent, is being used, the route of administration, and the size (body weight, height, body surface and/or organ size) and/or condition (the age, physical condition, and/or general health) of the patient. In certain embodiments, the clinician will consider the severity and history of the disease for which a specific binding agent to HGF, with or without at least one additional therapeutic agent, is being used. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, a higher dosage of specific binding agent to HGF is used with increasing weight of the patient undergoing therapy. In certain embodiments, the dosage may range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of a specific binding agent to HGF and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, the effective dosage of a specific binding agent to HGF used for treatment increases over the course of a patient treatment. In certain embodiments, the effective dosage of a specific binding agent to HGF used for treatment decreases over the course of a patient treatment. In certain embodiments, appropriate dosages may be ascertained through use of appropriate dose-response data.

In certain embodiments, the dosing regimen includes an initial administration of a therapeutically effective dose of a specific binding agent to HGF, with or without at least one additional therapeutic agent, on days 1, 7, 14, and 21 of a treatment period. In certain embodiments, the dosing regimen includes an initial administration of a therapeutically effective dose of a specific binding agent to HGF, with or without at least one additional therapeutic agent, on days 1, 2, 3, 4, 5, 6, and 7 of a week in a treatment period. In certain embodiments, the dosing regimen includes an initial administration of a therapeutically effective dose of a specific binding agent to HGF, with or without at least one additional therapeutic agent, on days 1, 3, 5, and 7 of a week in a treatment period. In certain embodiments, the dosing regimen includes an initial administration of a therapeutically effective dose of a specific binding agent to HGF, with or without at least one additional therapeutic agent, on days 1 and 3 of a week in a treatment period. In certain embodiments, the dosing regimen includes an initial administration of a therapeutically effective dose of a specific binding agent to HGF, with or without at least one additional therapeutic agent, on day 1 of a week in a treatment period. In certain embodiments, the treatment period comprises 1 week, 2 weeks, 3 weeks, one month, 3 months, 6 months, one year, or more. In certain embodiments, treatment periods are subsequent or separated from each other by one day, one week, 2 weeks, one month, 3 months, 6 months, one year, or more.

In certain embodiments, the same therapeutically effective dose of a specific binding agent to HGF is administered at each dosing over the course of a treatment period. In certain embodiments, different therapeutically effective doses of a specific binding agent to HGF are administered at each dosing over the course of a treatment period. In certain embodiments, the same therapeutically effective dose of a specific binding agent to HGF is administered at certain dosings over the course of a treatment period and different therapeutically effective doses are administered at certain other dosings.

In certain embodiments, the initial therapeutically effective dose of a specific binding agent to HGF is in a lower dosing range, for example, from 0.1 µg/kg up to 20 mg/kg, with subsequent doses in an upper dosing range, for example, from 20 mg/kg up to 100 mg/kg. In certain embodiments, the initial therapeutically effective dose of a specific binding agent to HGF is in an upper dosing range, for example, from 20 mg/kg up to 100 mg/kg, with subsequent doses in a lower dosing range, for example, from 0.1 µg/kg up to 20 mg/kg. Those ranges and any ranges discussed in this application include the endpoints and all values between the endpoints.

In certain embodiments, the initial therapeutically effective dose of a specific binding agent to HGF is administered as a "loading dose." "Loading dose" refers to an initial dose of a specific binding agent to HGF that is administered to a patient, where the dose of the specific binding agent to HGF administered falls within a higher dosing range, for example, 20 mg/kg up to 100 mg/kg. That range and any ranges discussed in this application include the endpoints and all values between the endpoints. In certain embodiments, the loading dose is administered as a single administration, for example, including, but not limited to, a single infusion administered intravenously. In certain embodiments, the loading dose is administered as multiple administrations, for example, including, but not limited to, multiple infusions administered intravenously. In certain embodiments, the loading dose is administered over a 24-hour period. In certain embodiments, after administration of the loading dose, the patient is administered one or more additional therapeutically effective doses of the specific binding agent to HGF. In certain such embodiments, subsequent therapeutically effective doses of the specific binding agent to HGF are administered according to a weekly dosing schedule, for example, but not limited to, once every two weeks, once every three weeks, or once every four weeks. In certain such embodiments, the dose of subsequent therapeutically effective doses falls within a lower dosing range, for example, 0.1 µg/kg up to 20 mg/kg.

In certain embodiments, after administration of the loading dose, the patient is administered one or more additional therapeutically effective doses of the specific binding agent to HGF according to a "maintenance schedule." Exemplary maintenance schedules include, but are not limited to, administration once a month, once every six weeks, once every two months, once every ten weeks, once every three months, once every 14 weeks, once every four months, once every 18 weeks, once every five months, once every 22 weeks, once every six months, once every seven months, once every eight months, once every nine months, once every ten months, once every eleven months, or once every twelve months. In certain embodiments, subsequent doses are administered at more frequent intervals, for example, once every two weeks to once every month. In certain such embodiments, subsequent doses of a specific binding agent to HGF fall within a lower dosing range, for example, 0.1 µg/kg up to 20 mg/kg. In certain embodiments, subsequent doses are administered at less frequent intervals, for example, once every month to once every twelve months. In certain such embodiments, subsequent doses of a specific binding agent to HGF fall within a higher dosing range, for example, 20 mg/kg up to 100 mg/kg.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, intravenous administration occurs by infusion over a period of 1 to 10 hours. In certain embodiments, intravenous administration occurs by infusion over a period of 1 to 8 hours. In certain embodiments, intravenous administration occurs by infusion over a period of 2 to 7 hours. In certain embodiments, intravenous administration occurs by infusion over a period of 4 to 6 hours. Those ranges and any ranges discussed in this application include the endpoints and all values between the endpoints. In certain embodiments, the infusion period depends on the specific binding agent to HGF to be administered. The determination of certain appropriate infusion periods is within the skill of the art. In certain embodiments, the initial infusion is given over a period of 4 to 6 hours, with subsequent infusions delivered more quickly. In certain such embodiments, subsequent infusions are administered over a period of 1 to 6 hours.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising a specific binding agent to HGF, with or without at least one additional therapeutic agent, in an ex vivo manner. In such instances, cells, tissues and/or organs that have been removed from the patient are exposed to a pharmaceutical composition comprising a specific binding agent to HGF, with or without at least one additional therapeutic agent, after which the cells, tissues and/or organs are subsequently implanted back into the patient.

In certain embodiments, a specific binding agent to HGF and/or any additional therapeutic agents can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

Example 1

To evaluate the effects of different compositions on a specific binding agent to HGF, compositions of 2.12.1, which is a fully human IgG2 monoclonal antibody against HGF, were formulated in 6 different formulations shown in Table 1 below. The concentration of 2.12.1 in all formulations was 30 mg/ml. The pH of all formulations was 5.7. Compositions were filled to a final volume of 1 ml in 3-cc vials. Compositions were incubated at 37° C. for 0 weeks, 4 weeks, 8 weeks, or 12 weeks. For each composition at each timepoint, a sample was removed from each vial for monitoring of antibody monomer by native SEC-HPLC.

TABLE 1

| Formulation | Stabilizing agent(s) | Buffering agent | Polysorbate 20 |
| --- | --- | --- | --- |
| H57S-20 | 5% (w/v) sorbitol | 10 mM L-his | 0.004% (w/v) |
| H57Su-20 | 9.5% (w/v) sucrose | 10 mM L-his | 0.004% (w/v) |
| H57Arg-20 | 100 mM L-arg | 10 mM L-his | 0.004% (w/v) |
| H57GL-20 | 5% (v/v) glycerol | 10 mM L-his | 0.004% (w/v) |
| H57Ala-Leu-20 | 60 mM L-ala; 60 mM L-leu | 10 mM L-his | 0.004% (w/v) |
| H57Lys-20 | 100 mM L-lys | 10 mM L-his | 0.004% (w/v) |

Native SEC-HPLC was performed using a TSK-GEL Super SW3000 4.6 mm×30 cm column (Tosoh Bioscience), with 4 µm particle size, on an Agilent 1100 Series HPLC with diode array detection. The mobile phase was 50 mM sodium phosphate, 100 mM sodium chloride, 5% ethanol, pH 7.5.

The flow rate was 0.3 ml/minute. The column eluate was monitored at 215 nm and at 280 nm. Integrated peak areas in the chromatograms were used to quantify the amounts of monomer and high molecular weight species.

FIG. 1 shows the results of native SEC-HPLC analysis of 2.12.1 compositions listed in Table 1 incubated at 37° C. for 0 weeks, 4 weeks, 8 weeks, or 12 weeks. As shown in Table 1, six stabilizing agents were tested and analyzed. Those were sorbitol, sucrose, glycerol, L-arginine, L-lysine, and a combination of L-alanine and L-leucine. "% Main Peak" reflects the quantity of 2.12.1 monomer. The results indicate that the "% Main Peak" after 12 weeks at 37° C. was highest in the 2.12.1 formulations containing one of the following: sorbitol, sucrose, glycerol, a combination of L-alanine and L-leucine. The results also indicate that the "% Main Peak" after 12 weeks at 37° C. was lowest in the 2.12.1 formulations containing either L-lysine or L-arginine. The results indicate that the effectiveness of stabilization of 2.12.1 by a combination of L-alanine and L-leucine was similar to that by sorbitol, sucrose, or glycerol. Note that while the results shown and discussed above are for experiments conducted at 37° C., similar results were obtained at other temperatures, including 4° C. (data not shown).

Example 2

To evaluate the effects of different compositions on a specific binding agent to HGF, compositions of 2.12.1 were formulated in 21 different formulations shown in Table 2 below. The concentration of 2.12.1 in all formulations was 30 mg/ml. Compositions were filled to a final volume of 1 ml in 3-cc vials. Compositions were incubated at 37° C. or 45° C. for a period of time as described in detail below. The pH of the formulation indicated in Table 2 was determined at the start of the experiment. The pH was stable for at least eight weeks at 45° C. In certain cases, the pH was unchanged from the starting pH after eight weeks at 45° C. in certain cases, the pH was 0.1-0.2 pH unit higher than the starting pH after eight weeks at 45° C. Certain compositions were monitored for antibody monomer by native SEC-HPLC (FIGS. 2-6). Certain compositions were also monitored for antibody aggregation and/or clips by non-reduced, denatured SEC-HPLC (FIG. 7).

TABLE 2

| Formulation | Stabilizing agent(s) | Buffering agent | pH | Polysorbate 20 |
|---|---|---|---|---|
| A52ST | 5% (w/v) sorbitol | 10 mM sodium acetate | 5.2 | 0.004% (w/v) |
| H57S | 5% (w/v) sorbitol | 10 mM L-his | 5.7 | none |
| H57S-20 | 5% (w/v) sorbitol | 10 mM L-his | 5.7 | 0.004% (w/v) |
| H57Su | 9.25% (w/v) sucrose | 10 mM L-his | 5.7 | none |
| H57Su-20 | 9% (w/v) sucrose | 10 mM L-his | 5.7 | 0.004% (w/v) |
| H57Arg-20 | 140 mM L-arg | 10 mM L-his | 5.7 | 0.004% (w/v) |
| H57Lys-20 | 140 mM L-lys | 10 mM L-his | 5.7 | 0.004% (w/v) |
| H57S-Lys-20 | 140 mM L-lys; 5% (w/v) sorbitol | 10 mM L-his | 5.7 | 0.004% (w/v) |
| H57GL-20 | 2.6% (v/v) glycerol | 10 mM L-his | 5.7 | 0.004% (w/v) |
| H57Ala-Leu-20 | 20 mM L-ala; 20 mM L-leu | 10 mM L-his | 5.7 | 0.004% (w/v) |
| H57SAla-Leu | 20 mM L-ala; 20 mM L-leu; 5% (w/v) sorbitol | 10 mM L-his | 5.7 | none |
| H57SAla-Leu-20 | 20 mM L-ala; 20 mM L-leu; 5% (w/v) sorbitol | 10 mM L-his | 5.7 | 0.004% (w/v) |
| H57PEG-20 | 0.25% PEG 8000 | 10 mM L-his | 5.7 | 0.004% (w/v) |
| H57-Mg-20 | 25 mM MgCl$_2$ | 10 mM L-his | 5.7 | 0.004% (w/v) |

TABLE 2-continued

| Formulation | Stabilizing agent(s) | Buffering agent | pH | Polysorbate 20 |
|---|---|---|---|---|
| H57-Ca-20 | 110 mM CaCl$_2$ | 10 mM L-his | 5.7 | 0.004% (w/v) |
| P57GL | 2.6% (v/v) glycerol | 10 mM propionate | 5.7 | none |
| P57-S20 | 5% (w/v) sorbitol | 10 mM propionate | 5.7 | 0.004% (w/v) |
| P57Ala-Leu | 200 mM L-ala; 75 mM L-leu | 10 mM propionate | 5.7 | none |
| P57Ala-Leu-20 | 200 mM L-ala; 75 mM L-leu | 10 mM propionate | 5.7 | 0.004% (w/v) |
| P57-PEG | 0.25% PEG 8000 | 10 mM propionate | 5.7 | none |
| P57-PEG-20 | 0.25% PEG 8000 | 10 mM propionate | 5.7 | 0.004% (w/v) |

For each composition at each timepoint indicated in FIGS. 2-6 described below, a sample was removed from each vial for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

Figure 2:
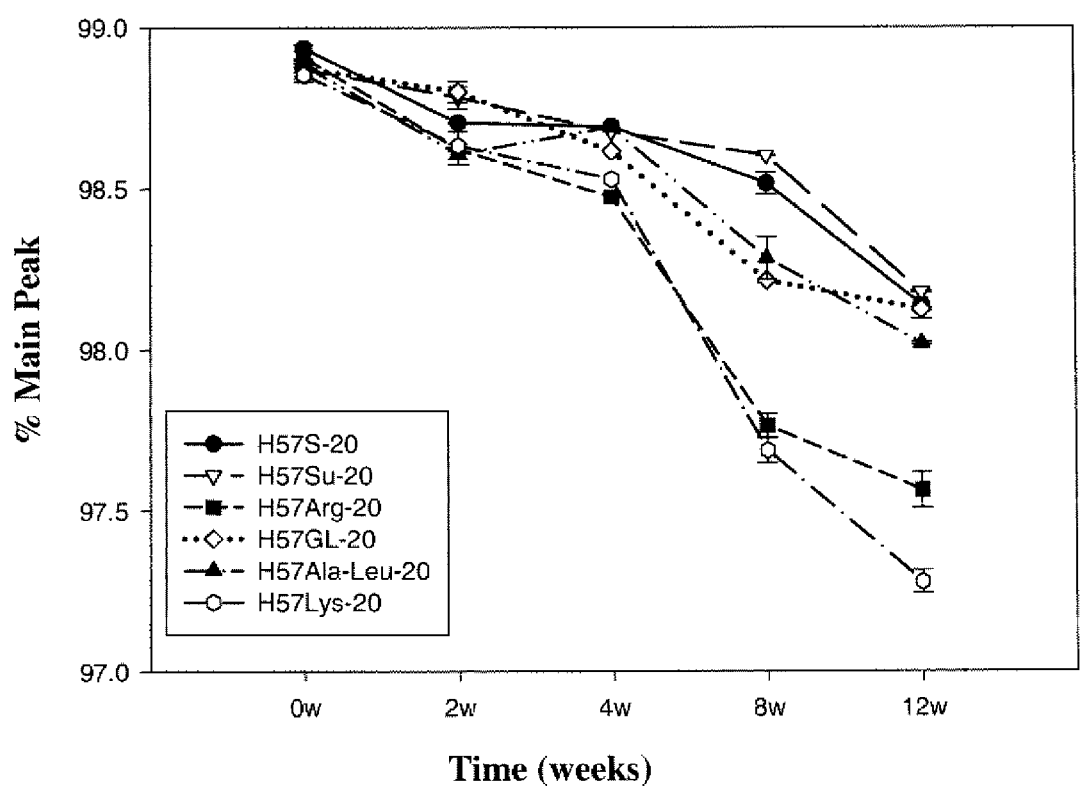
FIG. 2 shows the results of native SEC-HPLC analysis (expressed as percent main peak (monomer)) of various 2.12.1 compositions incubated at 45° C. for 0 weeks, 2 weeks, 4 weeks, 8 weeks, or 12 weeks according to the work discussed in Example 2.

FIG. 2 shows the results of native SEC-HPLC analysis of certain 2.12.1 compositions listed in Table 2 (as indicated in the FIG. 2 legend) incubated at 45° C. for 0 weeks, 2 weeks, 4 weeks, 8 weeks, or 12 weeks. Six stabilizing agents were tested and analyzed. Those were sorbitol, sucrose, glycerol, L-arginine, L-lysine, and a combination of L-alanine and L-leucine. "% Main Peak" reflects the quantity of 2.12.1 monomer. The results indicate that the "% Main Peak" for all compositions decreased at a faster rate at 45° C. compared to 37° C. (compare FIG. 1). In addition, the results indicate that, as in FIG. 1, after 12 weeks, the "% Main Peak" was highest in the 2.12.1 formulations containing one of the following: sorbitol, sucrose, glycerol, a combination of L-alanine and L-leucine. And, as in FIG. 1, the "% Main Peak" after 12 weeks was lowest in the 2.12.1 formulations containing either L-lysine or L-arginine. The results indicate that the effectiveness of stabilization of 2.12.1 by a combination of L-alanine and L-leucine was similar to that by sorbitol, sucrose, or glycerol.

Figure 3:
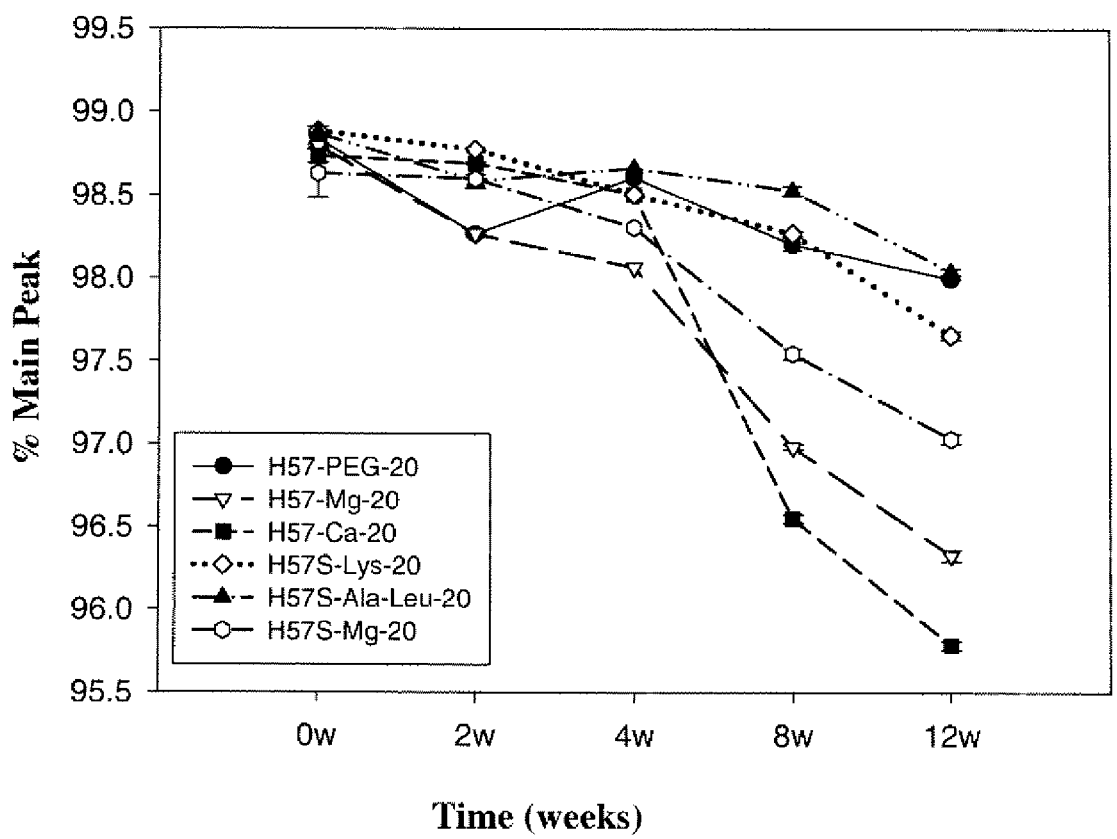
FIG. 3 shows the results of native SEC-HPLC analysis (expressed as percent main peak (monomer)) of various 2.12.1 compositions incubated at 450° C. for 0 weeks, 2 weeks, 4 weeks, 8 weeks, or 12 weeks according to the work discussed in Example 2.

FIG. 3 shows the results of native SEC-HPLC analysis of certain 2.12.1 compositions listed in Table 2 (as indicated in the FIG. 3 legend) incubated at 45° C. for 0 weeks, 2 weeks, 4 weeks, 8 weeks, or 12 weeks. Five stabilizing agents, alone or in combination with sorbitol as indicated, were tested and analyzed. Those were PEG 8000, MgCl$_2$, CaCl$_2$, L-lysine, and a combination of L-alanine and L-leucine. "% Main Peak" reflects the quantity of 2.12.1 monomer. The results indicate that the "% Main Peak" after 12 weeks at 45° C. was highest in 2.12.1 formulations containing PEG 8000 or containing a combination of L-alanine and L-leucine. The results also indicate that the "% Main Peak" after 12 weeks at 45° C. was lowest in the 2.12.1 formulations containing either of the divalent cations, Mg$^{2+}$ or Ca$^{2+}$. For the 2.12.1 formulation containing the positively-charged amino acid, lysine, the "% Main Peak" after 12 weeks at 45° C. was between the results for a combination of L-alanine and L-leucine and the results for Mg$^{2+}$ and Ca$^{2+}$.

Figure 4:
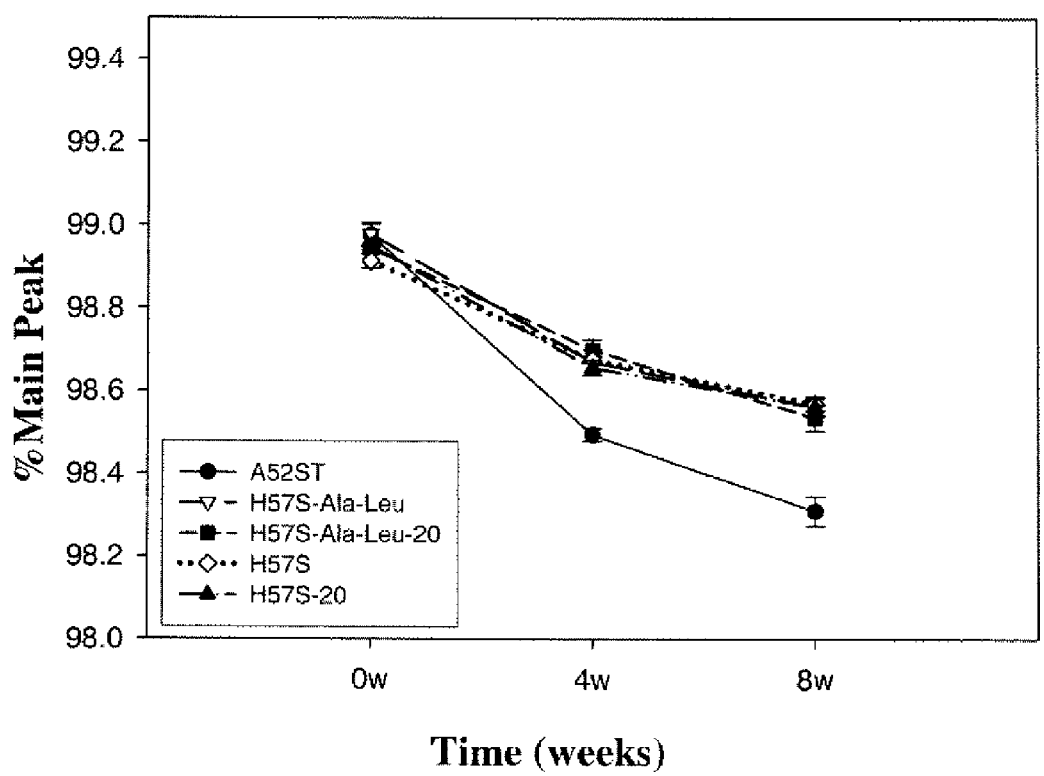
FIGS. 4 and 5 show the results of native SEC-HPLC analysis (expressed as percent main peak (monomer)) of various 2.12.1 compositions incubated at 45° C. for 0 weeks, 4 weeks, or 8 weeks according to the work discussed in Example 2.

FIG. 4 shows the results of native SEC-HPLC analysis of certain 2.12.1 compositions listed in Table 2 (as indicated in the FIG. 4 legend) incubated at 45° C. for 0 weeks, 4 weeks, or 8 weeks. Two buffering agents, L-histidine or acetate, and two stabilizing agents, sorbitol or a combination of L-alanine and L-leucine, were tested and analyzed. "% Main Peak" reflects the quantity of 2.12.1 monomer. The results indicate that the "% Main Peak" after 8 weeks at 45° C. was highest in 2.12.1 formulations containing L-histidine as a buffering agent, and either sorbitol as a stabilizing agent or a combination of sorbitol, L-alanine, and L-leucine as stabilizing agents. The results also indicate that the "% Main Peak" after 8 weeks at 45° C. was lowest in the 2.12.1 formulation containing acetate as a buffering agent and sorbitol as a stabilizing agent. In addition, the results indicate that the addition of polysorbate 20 to the 2.12.1 formulations containing L-histidine as a buffering agent, and either sorbitol as a stabilizing agent or a combination of sorbitol, L-alanine, and L-leucine as stabilizing agents did not have a measurable effect on stability in this assay.

Figure 5:
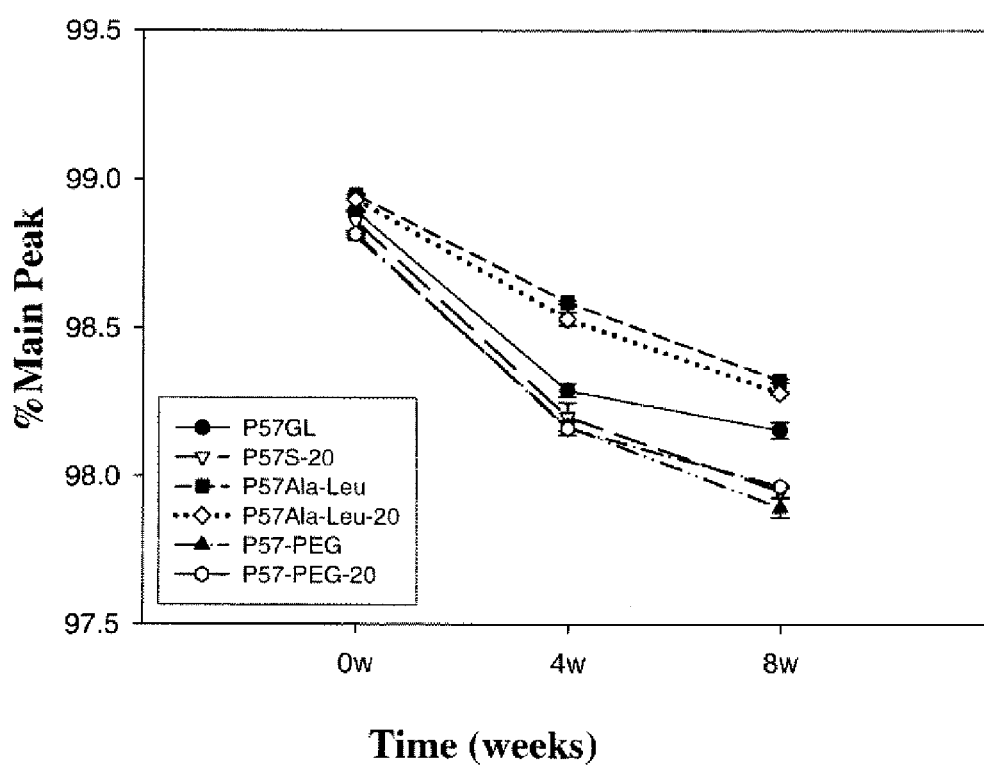

FIG. 5 shows the results of native SEC-HPLC analysis of certain 2.12.1 compositions listed in Table 2 (as indicated in the FIG. 5 legend) incubated at 45° C. for 0 weeks, 4 weeks, or 8 weeks. All of the 2.12.1 formulations contained propionate as a buffering agent. Four stabilizing agents were tested and analyzed. Those were glycerol, sorbitol, PEG 8000, and a combination of L-alanine and L-leucine. "% Main Peak" reflects the quantity of 2.12.1 monomer. The results indicate that the "% Main Peak" after 8 weeks at 45° C. was highest for the 2.12.1 formulations containing a combination L-alanine and L-leucine as stabilizing agents.

Figure 6:
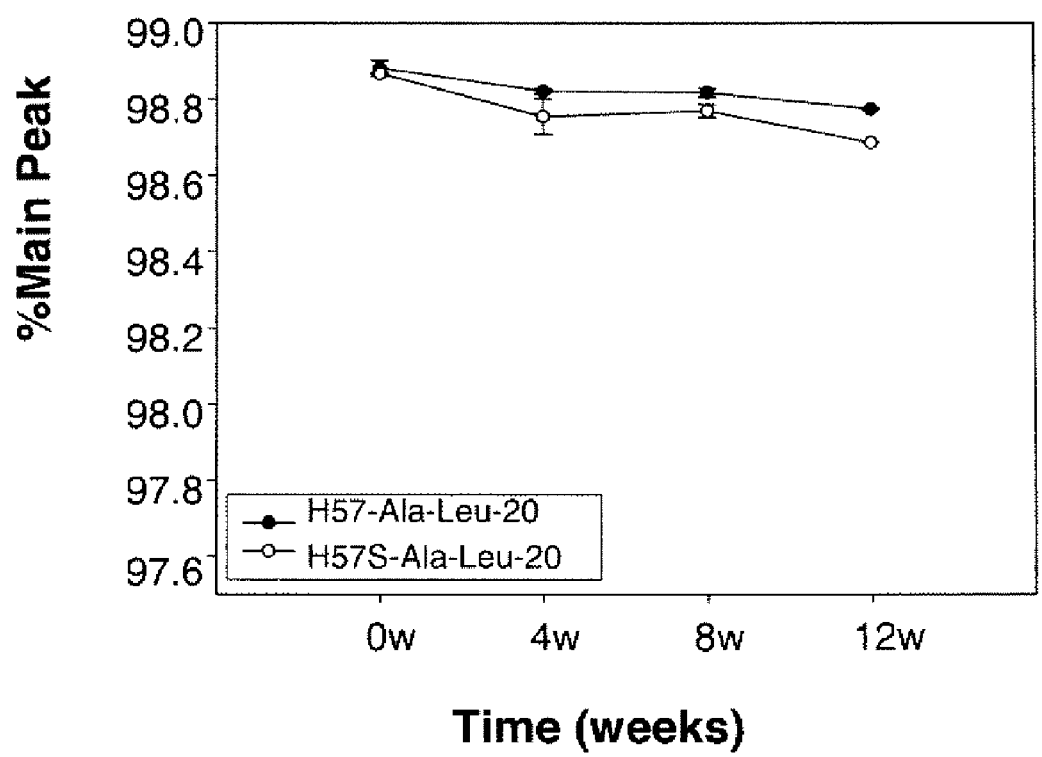
FIG. 6 shows the results of native SEC-HPLC analysis (expressed as percent main peak (monomer)) of two 2.12.1 compositions incubated at 37° C. for 0 weeks, 4 weeks, 8 weeks, or 12 weeks according to the work discussed in Example 2.
Figure 7:
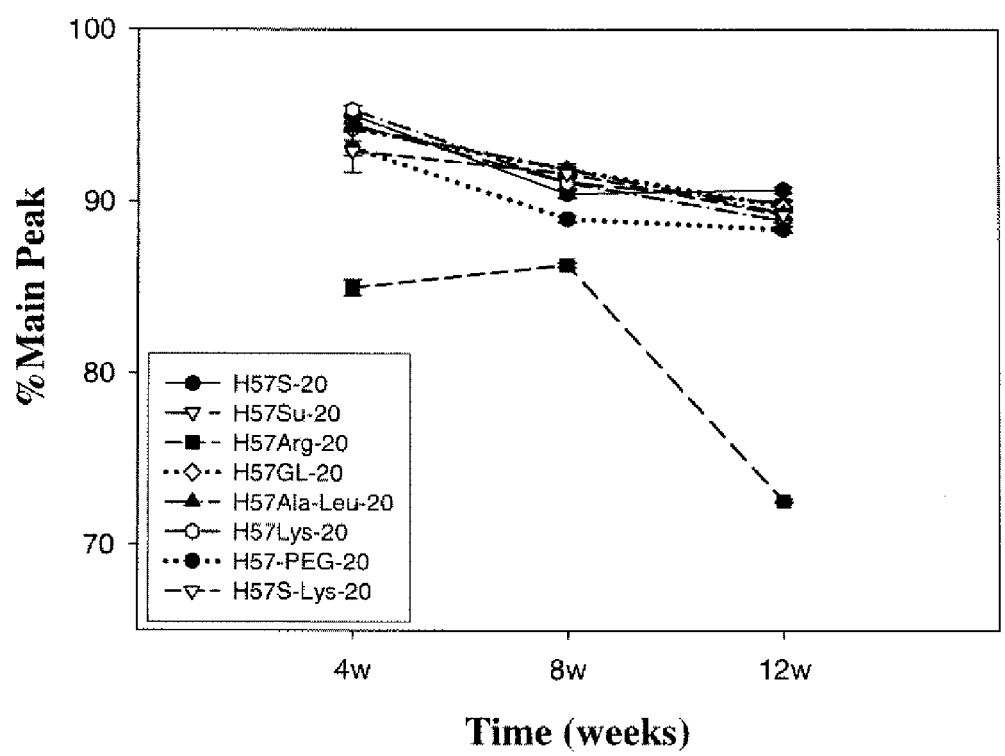
FIG. 7 shows the results of non-reduced denatured SEC-HPLC analysis (expressed as percent main peak (monomer)) of various 2.12.1 compositions incubated at 45° C. for 4 weeks, 8 weeks, or 12 weeks according to the work discussed in Example 2.

FIG. 6 shows the results of native SEC-HPLC analysis of two 2.12.1 compositions listed in Table 2 (as indicated in the FIG. 6 legend) incubated at 37° C. for 0 weeks, 4 weeks, 8 weeks, or 12 weeks. Both of the formulations contained L-histidine as a buffering agent and a combination of L-alanine and L-leucine as stabilizing agents. One formulation contained sorbitol, while the second did not. "% Main Peak" reflects the quantity of 2.12.1 monomer. The results indicate that the "% Main Peak" after 12 weeks at 37° C. for the 2.12.1 formulation lacking sorbitol was similar or slightly higher than for the 2.12.1 formulation containing sorbitol.

To monitor certain antibody stability, such as aggregation and clipping, certain 2.12.1 compositions listed in Table 2 (as indicated in the FIG. 7 legend) were analyzed by non-reduced, denatured SEC-HPLC. For each composition at each timepoint indicated in FIG. 7 described below, a sample was removed from each vial for analysis by non-reduced, denatured SEC-HPLC. Prior to performing non-reduced, denatured SEC-HPLC, both sodium dodecyl sulphate (SDS) and iodoacetamide were added to each sample. The final concentration of SDS in each sample was 2%. The final concentration of iodoacetamide in each sample was 15 mM. The final protein concentration in each sample was 1.5 mg/ml. After adding SDS and iodoacetamide, samples were incubated at 80° C. for 20 minutes. Non-reduced, denatured SEC-HPLC was performed using two TSKgel G3000-SWxL 7.8 mm×300 mm columns (Tosoh Bioscience) employed in series, on an Agilent 1050 Series HPLC with diode array detection. The buffer for the mobile phase was 150 mM sodium phosphate, 100 mM sodium chloride, 0.1% SDS, pH 6.9. The sample chamber was kept at room temperature. The buffer for the mobile phase was filtered just prior to starting HPLC. Integrated peak areas in the chromatograms were used to quantify the amounts of monomer, high molecular weight species, and low molecular weight species.

FIG. 7 shows the results of non-reduced, denatured SEC-HPLC analysis of certain 2.12.1 compositions listed in Table 2 (as indicated in the FIG. 7 legend) incubated at 45° C. for 4 weeks, 8 weeks, or 12 weeks. Eight stabilizing agents were tested and analyzed. Those were sorbitol, sucrose, glycerol, polyethylene glycol, L-arginine, L-lysine, a combination of L-lysine and sorbitol, and a combination of L-alanine and L-leucine. "% Main Peak" reflects the quantity of 2.12.1 monomer. The quantity of antibody that is stable is proportional to the "% Main Peak" result. Thus, the higher the "% Main Peak," the higher the amount of antibody stability. And the lower the "% Main Peak," the lower the amount of antibody stability.

The results shown in FIG. 7 indicate that the "% Main Peak" over the 12 week time course at 45° C. was similar for all of the 2.12.1 formulations tested, except for the formulation containing L-arginine. The 2.12.1 formulation containing L-arginine showed the lowest "% Main Peak" at all time points at 45° C., with a sharp decline from 8 weeks to 12 weeks. That result suggests that antibody formulations containing L-arginine were less stable than the other formulations analyzed.

In addition, the "% Main Peak" during the 12 week time course at 45° C. for the 2.12.1 formulation containing a combination of L-alanine and L-leucine was similar to that for the 2.12.1 formulations containing L-lysine. That result suggests that antibody stability in each of those formulations was similar. However, as discussed above in connection with FIGS. 1, 2, and 3, formulations containing L-lysine, either without sorbitol (FIGS. 1 and 2) or with sorbitol (FIG. 3), showed a greater loss of antibody monomer over time compared to the formulations containing a combination of L-alanine and L-leucine. That conclusion was suggested by the greater decline in "% Main Peak" observed over time for the L-lysine-containing formulations compared to the formulations containing a combination of L-alanine and L-leucine, as determined by native SEC-HPLC. Thus, the combination of the results presented in FIGS. 1, 2, 3, and 7 suggests that formulations containing nonpolar amino acids, such as L-alanine and L-leucine, stabilized antibodies more effectively than formulations containing positively charged amino acids, such as L-arginine and L-lysine.

To summarize, FIGS. 1-7 show the % Main Peak results, which reflect the quantity of 2.12.1 monomer. Accordingly, antibody stability is proportional to the % Main Peak results shown. Thus, the results shown in FIGS. 1-7 suggest that nonpolar amino acids, such as L-alanine and L-leucine, effectively stabilized 2.12.1.

Example 3

To evaluate the effects of free L-methionine ("Met") in compositions comprising a specific binding agent to HGF, compositions of 2.12.1, either with Met or without Met, were exposed to light of various wavelengths and intensities, for various periods of time. The concentration of 2.12.1 in the compositions was between 29 and 30 mg/ml and was formulated in 10 mM sodium acetate, 5% sorbitol, pH 5.2. The concentration of Met, when present in a composition, was 10 mM. Compositions were filled to a final volume of 1 ml in 3-cc glass vials. For each light condition tested, the visual clarity and turbidity of the formulations were inspected by eye and/or by ultraviolet/visible (UV/Vis) spectrophotometric measurements, as described in detail below.

For the experiments described below, UV/Vis spectrophotometric measurements were made using a diode array UV-visible spectrophotometer (Agilent Model No. 8453, Santa Clara, Calif.). After exposure to a test condition, samples were placed in the spectrophotometer. As indicated below, the absorbance of light by the samples was measured either at a single wavelength or across a spectrum of wavelengths using the spectrophotometer according to the manufacturer's instructions. "Spectrophotometric scanning" refers to measurements made across a spectrum of wavelengths. In the examples described below, wavelengths of 200-400 nm correspond to the ultraviolet (UV) range of light. Wavelengths of 401-800 nm correspond to the visible (Vis) range of light. For each of the measurements discussed in the examples below, a "blank sample" of the buffer without protein was used to set the spectrophotometer to zero. For measurement of protein-containing compositions, undiluted samples were used.

Figure 8:
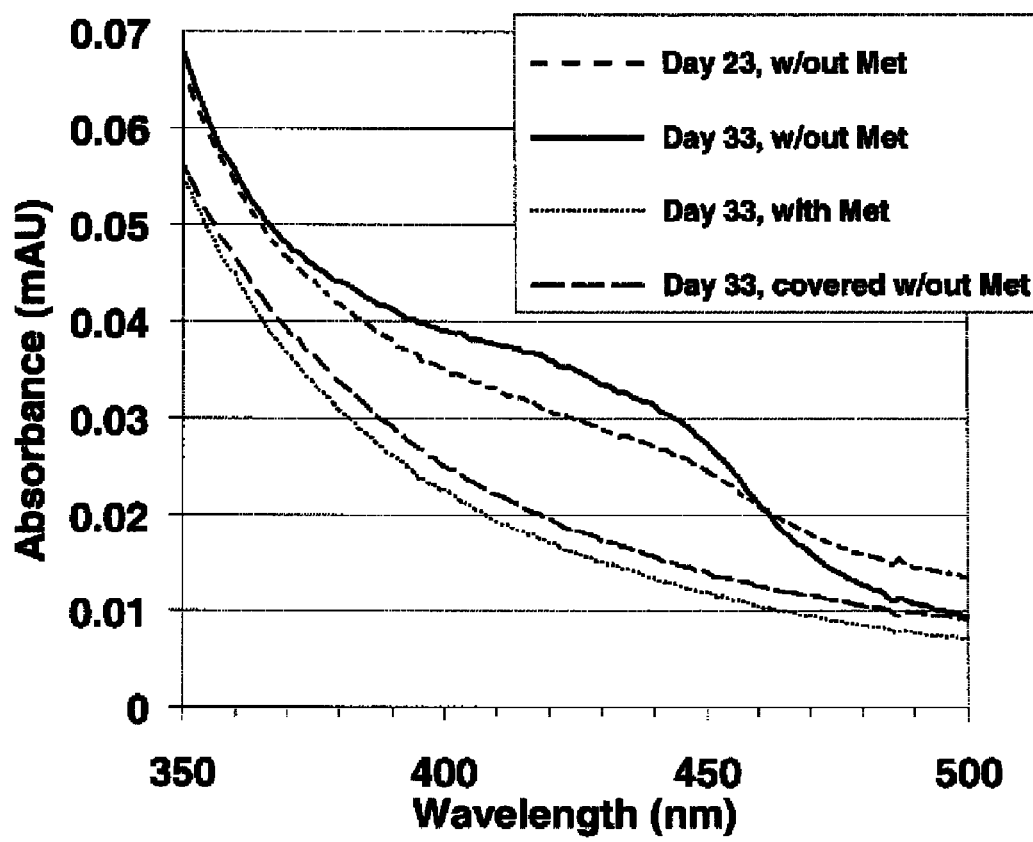
FIG. 8 shows the results of UV/Vis spectrophotometric scanning (expressed as light absorbance) of various 2.12.1 compositions, with or without free L-methionine added, exposed to fluorescent (visible) light for 23 days or 33 days, according to the work discussed in Example 3.

FIG. 8 shows the results of spectrophotometric scanning of 2.12.1 compositions in the range from 350 nm (UV) to 500 nm (Vis). Except for the control, the compositions were exposed to a fluorescent lamp that emitted visible light in a "deli case-style" cold box (Storage Refrigerator with glass doors, VWR) at 3° C. to 5° C. Four conditions were tested and analyzed: (1) without Met, exposed to visible light for 23 days (labeled Day 23, w/out Met, green line, FIG. 8 legend); (2) without Met, exposed to visible light for 33 days (labeled Day 33, w/out Met, red line, FIG. 8 legend); (3) with Met, exposed to visible light for 33 days (labeled Day 33, with Met, blue line, FIG. 8 legend); and (4) without Met, covered for 33 days, not exposed to visible light (control) (labeled Day 33, covered w/out Met, black line, FIG. 8 legend).

the composition at 430 nm. The results also suggest that addition of Met to 2.12.1 compositions reduced discoloration of the composition following exposure to visible light.

Figure 9:
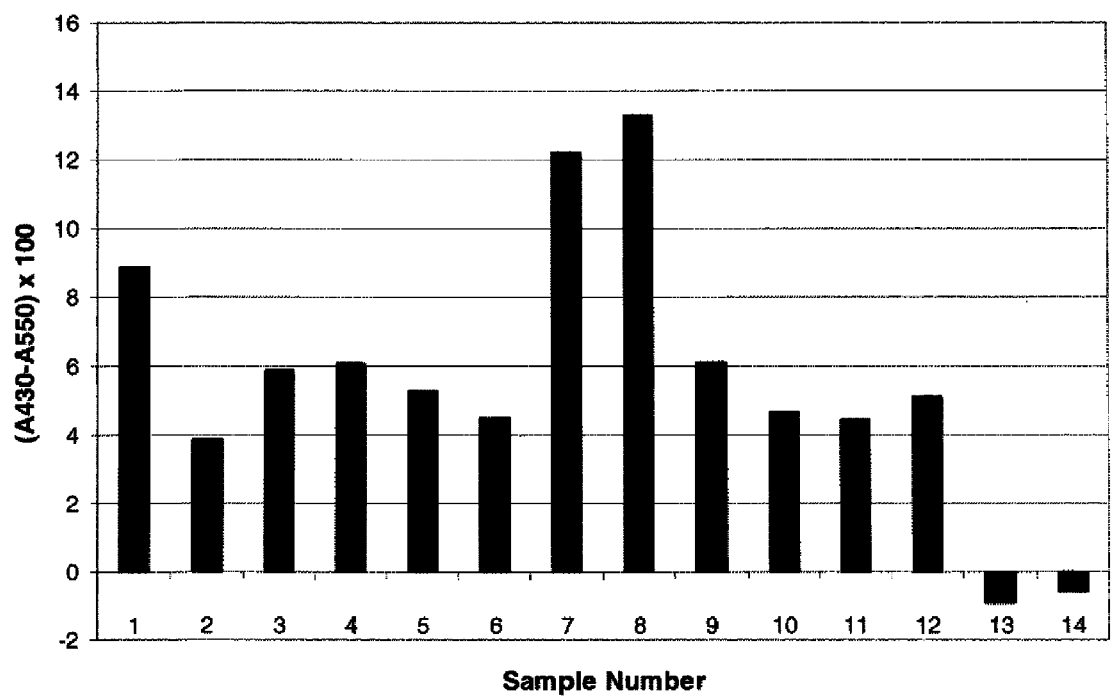
FIG. 9 shows the results of spectrophotometric measurements made at 430 nm and 550 nm (expressed as light absorbance) of various 2.12.1 compositions, with or without free L-methionine added, exposed to xenon (UV and visible) light for 12 hours at 25° C., according to the work discussed in Example 3. The figure depicts the difference between the spectrophotometric measurements made at 430 nm and 550 nm. The formulations of the 2.12.1 compositions are indicated in Table 3.

FIG. 9 shows the results of spectrophotometric measurements of 2.12.1 compositions exposed to a xenon lamp that emitted UVA, UVB, and visible light in a Q-Sun Light Box (Q-Lab Corporation, Cleveland, Ohio). The formulations of the 2.12.1 compositions are shown in Table 3 below. The wavelengths of light emitted by the xenon lamp were between 170 nm and 900 nm. Samples were exposed to the xenon lamp for 12 hours at room temperature (25° C.) and relative humidity of 33%. The lamp strength was in the range of 219-235 kJ/m². Following exposure to the xenon lamp, the samples were covered and held at 4° C. until performing absorbance measurements and analysis. All samples were held for the same amount of time and under the same conditions prior to measuring absorbance. Light absorbance of each sample was measured in the visible range at 430 nm and 550 nm. FIG. 9 shows the relative discoloration of each sample depicted as the difference in absorbance between 430 nm and 550 nm. The results show that one 2.12.1 composition with Met (sample number 2 in FIG. 9 and Table 3) demonstrated the smallest difference in absorbance between 430 nm and 550 nm. That result suggests that addition of Met to the 2.12.1 composition reduced discoloration of the composition following exposure to the xenon lamp (UVA, UVB, and visible light).

TABLE 3

Formulations of 2.12.1 compositions shown in FIG. 9.

| Sample No. | Stabilizing agent(s) | Buffering agent; additional agent(s) | pH | Surfactant |
| --- | --- | --- | --- | --- |
| 1 | 5% (w/v) sorbitol | 10 mM sodium acetate | 5.2 | none |
| 2 | 5% (w/v) sorbitol; 1 mM L-Methionine | 10 mM L-his; 0.5 mM EDTA | 5.7 | 0.004% (w/v) polysorbate 20 |
| 3 | 5% (w/v) sorbitol | 10 mM L-his; 0.5 mM EDTA | 5.7 | 0.004% (w/v) polysorbate 20 |
| 4 | 5% (w/v) sorbitol; 1 mM L-Methionine | 10 mM L-his; 0.5 mM EDTA | 5.7 | 0.004% (w/v) polysorbate 80 |
| 5 | 5% (w/v) sorbitol | 10 mM L-his | 5.7 | none |
| 6 | 4.5% (w/v) sorbitol; 20 mM L-ala, 20 mM L-leu | 10 mM L-his | 5.7 | none |
| 7 | 5% (w/v) sorbitol | 10 mM glutamate | 5.0 | none |
| 8 | 5% (w/v) sorbitol | 10 mM glutamate | 5.0 | 0.004% (w/v) polysorbate 20 |
| 9 | 9.25% (w/v) sucrose | 10 mM potassium phosphate | 6.0 | none |
| 10 | 9.25% (w/v) sucrose | 10 mM potassium phosphate | 6.0 | 0.004% (w/v) polysorbate 20 |
| 11 | 200 mM L-ala; 75 mM L-leu | 10 mM propionate | 5.7 | none |
| 12 | 200 mM L-ala; 75 mM L-leu | 10 mM propionate | 5.7 | 0.004% (w/v) polysorbate 20 |
| 13 (No 2.12.1) | 5% (w/v) sorbitol | 10 mM glutamate | 5.0 | 0.004% (w/v) polysorbate 20 |
| 14 (No 2.12.1) | 200 mM L-ala; 75 mM L-leu | 10 mM propionate | 5.7 | 0.004% (w/v) polysorbate 20 |

Figure 10:
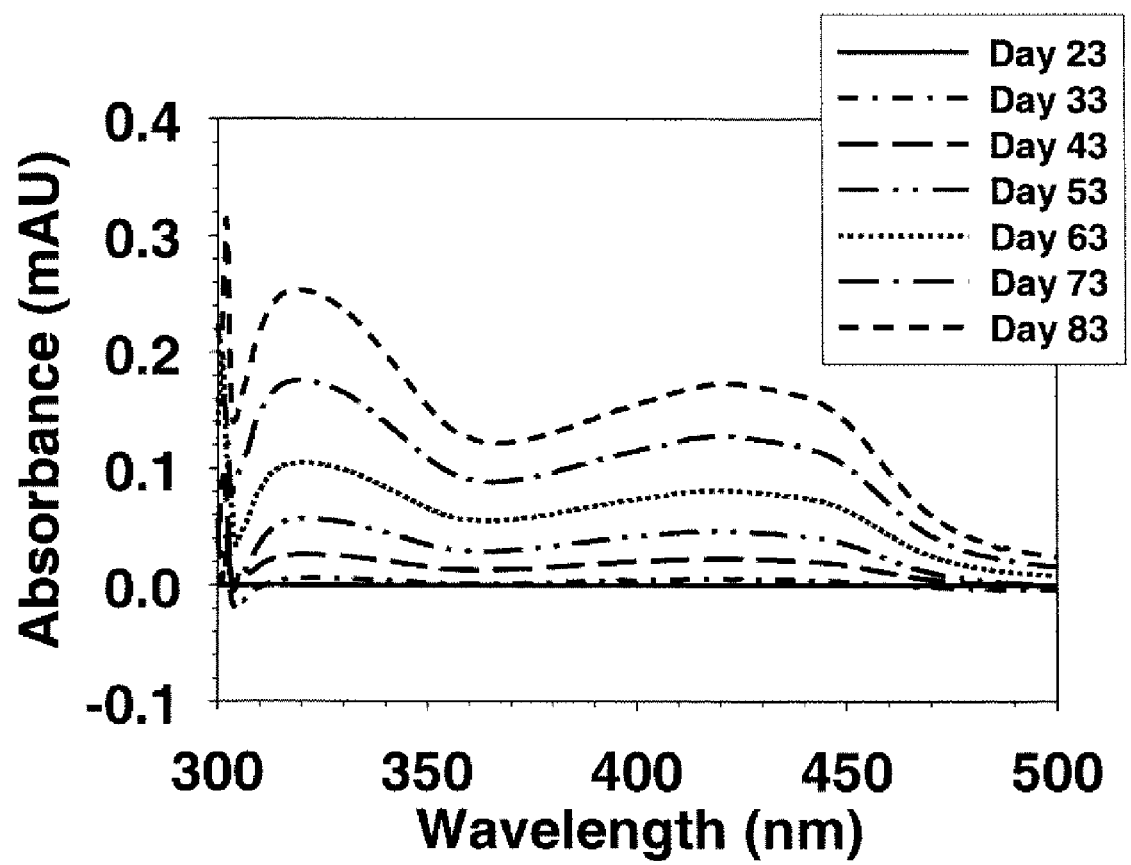
FIG. 10 shows the results of UV/Vis spectrophotometric scanning (expressed as light absorbance (mAU)) of a 2.12.1 composition, without free L-methionine added, exposed to fluorescent (visible) light for a period of time ranging from 23 days to 83 days according to the work discussed in Example 3. The graph is a plot of spectral difference between the indicated timepoint and day 23.
Figure 11:
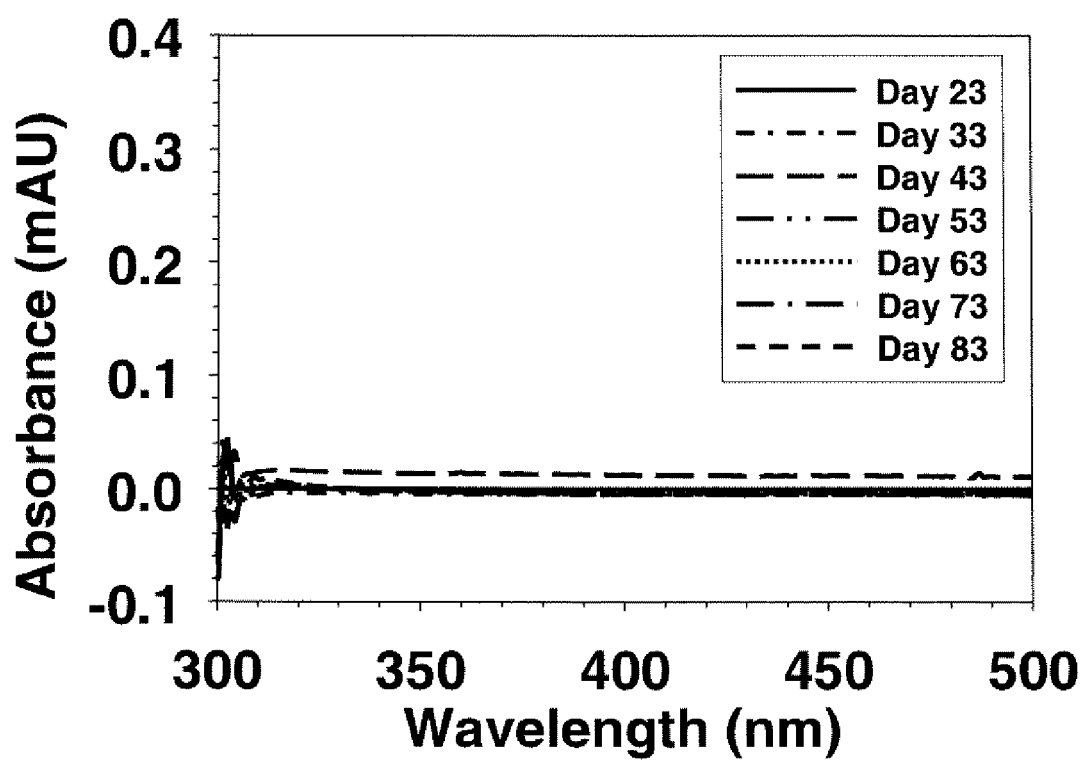
FIG. 11 shows the results of UV/Vis spectrophotometric scanning (expressed as light absorbance (mAU)) of a 2.12.1 composition, with free L-methionine added, exposed to fluorescent (visible) light for a period of time ranging from 23 days to 83 days according to the work discussed in Example 3. The graph is a plot of spectral difference between the indicated timepoint and day 23.

The results show that the compositions without Met and exposed to visible light absorbed light in the visible range of 410 nm to 460 nm. The absorption peak was at 430 nm. Those compositions were also discolored, as determined by visual inspection of the vials (data not shown). The results also show that the composition with Met and exposed to visible light and the control did not exhibit an absorption peak at 430 nm. In addition, those compositions were not discolored, as determined by visual inspection of the vials (data not shown). Thus, the results suggest that discoloration of 2.12.1 compositions could be quantitated by measuring light absorbance of FIG. 10 shows the results of spectrophotometric scanning in the range from 300 nm (UV) to 450 nm (Vis), of an 2.12.1 composition, without Met, exposed to a fluorescent lamp that emitted visible light in a "deli case-style" cold box (Storage Refrigerator with glass doors, VWR) at 3° C. to 5° C. The composition was exposed to the lamp for a period of time ranging from 23 days to 83 days at 4-8° C. The graph is a plot of spectral difference between the indicated timepoint and day 23. The results show that, in the absence of Met, absorbance at 430 nm increased with increased exposure time to fluorescent light. The results also show increased absorbance with increased exposure time across the spectrum with peaks at 320 nm and 425 nm to 445 nm FIG. 11 shows the results of spectrophotometric scanning in the range from 300 nm (UV) to 450 nm (Vis), of an 2.12.1 composition, with Met, exposed to a fluorescent lamp that emitted visible light in a "deli case-style" cold box (Storage Refrigerator with glass doors, VWR) at 3° C. to 5° C. The composition was exposed to the lamp for a period of time ranging from 23 days to 83 days at 4-8° C. The graph is a plot of spectral difference between the indicated timepoint and day 23. The results show that, in the presence of Met, absorbance across the spectrum remained constant for the entire time period tested. The results shown in FIG. 11, compared to the results shown in FIG. 10, suggest that addition of Met to 2.12.1 compositions reduced discoloration of the composition following continuous exposure to fluorescent (visible) light for a period of time of at least 83 days.

Figure 12:
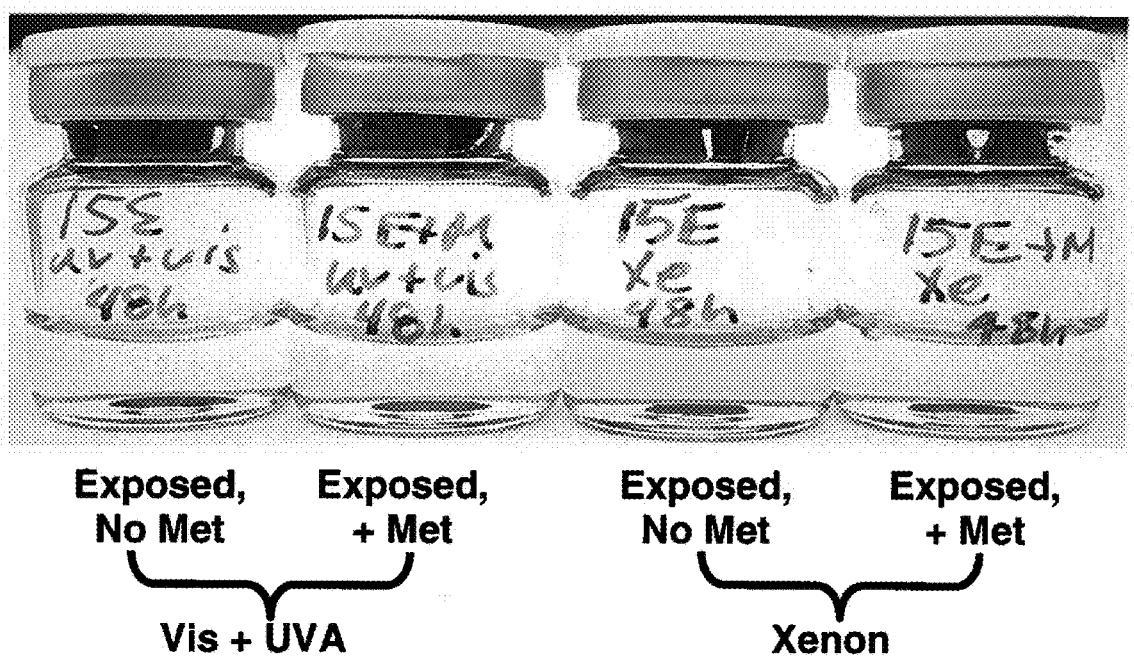
FIG. 12 is a digital photograph showing discoloration of 2.12.1 compositions in vials exposed to either UVA plus visible light (left two vials) or to xenon light (right two vials) for 48 hours according to the work discussed in Example 3. For each light source, one vial contained free L-methionine ("+Met"), and one did not ("No Met").

FIG. 12 shows a digital photograph of 2.12.1 compositions in vials exposed to one of two different light sources for 48 hours. One light source was UVA (315 nm to 380 nm) plus visible light ("UVA/Vis"). The second light source was a xenon lamp that emitted UVA, UVB, and visible light in a Q-Sun Light Box. The wavelengths of light emitted by the xenon lamp were between 170 nm and 900 nm. For each of the light sources, one 2.12.1-containing vial contained Met and one did not contain Met. The photograph shows that, for the vials exposed to UV/Vis, addition of Met to the composition reduced discoloration. The photograph also shows that, for the vials exposed to xenon light, which is stronger than UVA/Vis, addition of Met also reduced discoloration, although to a lesser degree than in the samples exposed to UVA/Vis. Thus, those results are consistent with the data shown in FIGS. 8-11, which suggest that addition of Met to 2.12.1 compositions reduced discoloration of the composition following exposure to various light sources.

Figure 13:
FIG. 13 shows digital photographs showing discoloration of 2.12.1 compositions in vials exposed to xenon light for 0 hours, 4 hours, 8 hours, 12 hours, 24 hours, or 48 hours according to the work discussed in Example 3. Top row (a): without free L-methionine added; middle row (b): with free L-methionine added; bottom row (c); without free L-methionine added, covered.
Figure 13:
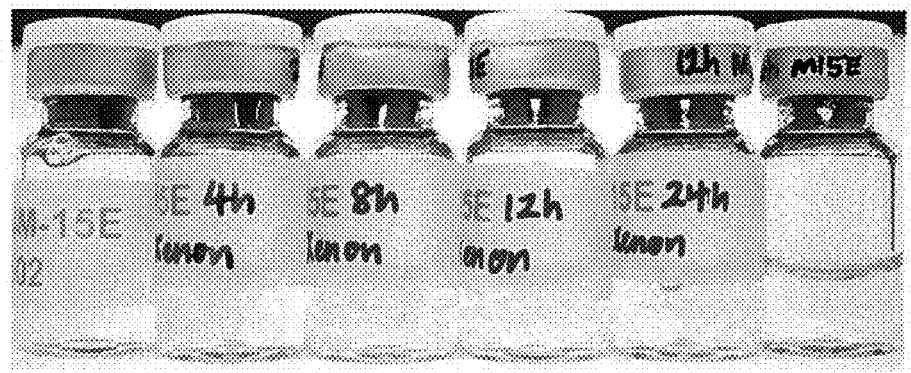
Figure 13:
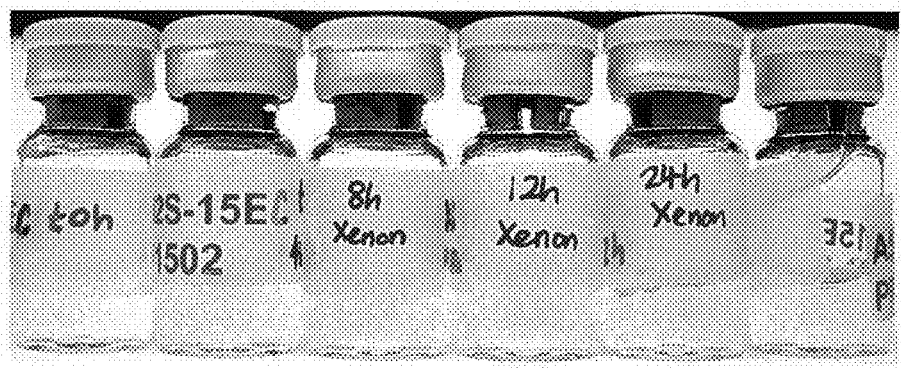

FIG. 13 shows digital photographs of 2.12.1 compositions in vials exposed to a xenon lamp that emitted UVA, UVB, and visible light in a Q-Sun Light Box for 0 hours, 4 hours, 8 hours, 12 hours, 24 hours, or 48 hours at 25-30° C. The wavelengths of light emitted by the xenon lamp were between 170 nm and 900 nm. The vials in the top row (a) did not contain Met. The vials in the middle row (b) contained Met. The vials in the bottom row (c) did not contain Met, and were covered. Comparison of the photograph in (a) to the photograph in (b) shows that addition of Met to the composition reduced discoloration for up to 12 hours of exposure to a xenon lamp. Comparison of the photograph in (a) to the photograph in (b) also shows that, for 12 hours to 48 hours of exposure to a xenon lamp, addition of Met also reduced discoloration, although to a lesser degree than in the samples exposed for less than 12 hours. Thus, those results are consistent with the data shown in FIGS. 8-12, which suggest that addition of Met to 2.12.1 compositions reduced discoloration of the composition following exposure to various light sources.

Example 4

To evaluate the effects of different compositions on a specific binding agent to HGF, compositions of 2.12.1 were formulated in 17 different formulations shown in Table 4 below. The concentration of 2.12.1 in all formulations was 30 mg/ml. Compositions were filled to a final volume of 1 ml in 3-cc vials. Compositions were incubated at 29° C., 37° C., or 45° C. for a period of time as described in detail below. The pH of the formulation indicated in Table 4 was determined at the start of the experiment. The pH was stable for at least eight weeks at 45° C. In certain cases, the pH was unchanged from the starting pH after eight weeks at 45° C. In certain cases, the pH was 0.1-0.2 pH unit higher than the starting pH after eight weeks at 45° C. Certain compositions were monitored for antibody monomer by native SEC-HPLC (data not shown).

TABLE 4

| Formulation | Stabilizing agent(s) | Buffering agent | pH | Polysorbate 20 |
| --- | --- | --- | --- | --- |
| A52ST | 5% (w/v) sorbitol | 10 mM sodium acetate | 5.2 | 0.004% (w/v) |
| A56Ala-Leu | 200 mM L-ala; 75 mM L-leu | 10 mM sodium acetate | 5.6 | none |
| A56Ala-Leu-4 | 200 mM L-ala; 75 mM L-leu | 10 mM sodium acetate | 5.6 | 0.004% (w/v) |
| A56Ala-Leu-8 | 200 mM L-ala; 75 mM L-leu | 10 mM sodium acetate | 5.6 | 0.008% (w/v) |
| A56Ala-Leu-12 | 200 mM L-ala; 75 mM L-leu | 10 mM sodium acetate | 5.6 | 0.012% (w/v) |
| H57SuM | 9.25% (w/v) sucrose 1 mM L-met | 10 mM L-his | 5.7 | none |
| H57SuM-20-4 | 9.25% (w/v) sucrose 1 mM L-met | 10 mM L-his | 5.7 | 0.004% (w/v) |
| H57SuM-20-8 | 9.25% (w/v) sucrose 1 mM L-met | 10 mM L-his | 5.7 | 0.008% (w/v) |
| H57SuM-20-12 | 9.25% (w/v) sucrose 1 mM L-met | 10 mM L-his | 5.7 | 0.012% (w/v) |
| P57Ala-Leu | 200 mM L-ala; 75 mM L-leu | 10 mM sodium propionate | 5.7 | none |
| P57Ala-Leu-20-4 | 200 mM L-ala; 75 mM L-leu | 10 mM sodium propionate | 5.7 | 0.004% (w/v) |
| P57Ala-Leu-20-8 | 200 mM L-ala; 75 mM L-leu | 10 mM sodium propionate | 5.7 | 0.008% (w/v) |
| P57Ala-Leu-20-12 | 200 mM L-ala; 75 mM L-leu | 10 mM sodium propionate | 5.7 | 0.012% (w/v) |
| K6Su | 9.25% (w/v) sucrose | 10 mM potassium phosphate | 6.0 | none |
| K6Su-20-4 | 9.25% (w/v) sucrose | 10 mM potassium phosphate | 6.0 | 0.004% (w/v) |
| K6Su-20-8 | 9.25% (w/v) sucrose | 10 mM potassium phosphate | 6.0 | 0.008% (w/v) |

TABLE 4-continued

| Formulation | Stabilizing agent(s) | Buffering agent | pH | Polysorbate 20 |
|---|---|---|---|---|
| K6Su-20-12 | 9.25% (w/v) sucrose | 10 mM potassium phosphate | 6.0 | 0.012% (w/v) |

For each composition at certain timepoints (0 weeks, 2 weeks, 4 weeks, 8 weeks, or 12 weeks), a sample was removed from each vial for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

2.12.1 formulations (Table 4) in either an acetate buffer or a propionate buffer and containing a combination of L-alanine and L-leucine as the stabilizing agent, were tested and compared to the following: (1) a formulation in histidine buffer and containing sucrose and methionine as the stabilizing agent; (2) a formulation in phosphate buffer and containing sucrose as the stabilizing agent; and (3) a formulation in an acetate buffer and containing sorbitol as the stabilizing agent. "% Main Peak" reflected the quantity of 2.12.1 monomer. The results indicated that the "% Main Peak" for all compositions decreased at a faster rate at 45° C. compared to 37° C. or 29° C. (data not shown). In addition, the results indicated that the "% Main Peak" in the two 2.12.1 formulations containing a combination of L-alanine and L-leucine was comparable to the "% Main Peak" in the formulation in an acetate buffer and containing sorbitol as the stabilizing agent (data not shown). The results are in agreement with those discussed in Example 2 and confirm that the effectiveness of stabilization of 2.12.1 by a combination of L-alanine and L-leucine was similar to that by sorbitol.

To evaluate formulations containing a combination of L-alanine and L-leucine and subjected to freezing and thawing, formulations A56Ala-Leu and P57Ala-Leu (Table 4) were tested for stability after being subjected to one freeze/thaw cycle, with the freeze temperature at –20° C. or at –30 C. Following the freeze/thaw cycle, the formulations were analyzed by native SEC-HPLC. In some experiments, the formulations were subjected to three freeze/thaw cycles. The results demonstrated aggregate formation in both A56Ala-Leu and P57Ala-Leu formulations (data not shown).

To evaluate the effects of various agents in compositions containing a specific binding agent to HGF and one or more non-polar amino acids and subjected to one or more freeze/thaw cycles, compositions of 2.12.1 were formulated in 24 different formulations shown in Table 5 below. The concentration of 2.12.1 in all formulations was 30 mg/ml. All of the 2.12.1 formulations listed in Table 5 contained 200 mM L-alanine, 75 mM L-leucine, and 10 mM sodium acetate, pH 5.6. Each of the agents listed in Table 5 was present at a concentration of 100 mM. Compositions were filled to a final volume of 0.5 ml in 3-cc vials.

TABLE 5

| Formulation | Agent |
|---|---|
| A56AL-G | glycine |
| A56AL-EG | ethylene glycol |
| A56AL-PEG 200 | polyethylene glycol 200 |
| A56AL-PEG 400 | polyethylene glycol 400 |
| A56AL-PEG 600 | polyethylene glycol 600 |
| A56AL-PEG 4000 | polyethylene glycol 4000 |
| A56AL-PVP | polyvinylpyrrolidone K15 |
| A56AL-MP | (±)2-methyl-2,4-pentanediol |
| A56AL-Hex | 1,6-hexanediol |
| A56AL-PG | propylene glycol |
| A56AL-P | 2-propanol |
| A56AL-E | ethanol |
| A56AL-M | methanol |
| A56AL-Su | sucrose |
| A56AL-ME | meso-erythritol |
| A56AL-X | xylitol |
| A56AL-I | inositol |
| A56AL-Ra | raffinose |
| A56AL-Tr | trehalose |
| A56AL-Gl | glucose |
| A56AL-Bu | 2,3-butanediol |
| A56AL-LBu | L-(+)-2,3-butanediol |
| A56AL-R | arginine |
| A56AL-H | histidine |

Compositions were subjected to zero, three, or five freeze/thaw cycles, with the freeze temperature at –30° C. in one experiment, and at –70° C. in another experiment. For each cycle, compositions were placed in the freezer (a –30° C. freezer or a –70° C. freezer) for 16 hours and then thawed by placing at room temperature (25° C.) for one-two hours. After thawing, compositions were stored at 4° C. for up to ten days and then analyzed by native SEC-HPLC. Certain compositions were monitored for antibody monomer by native SEC-HPLC (FIGS. 14 (a) and (b)).

Figure 14:
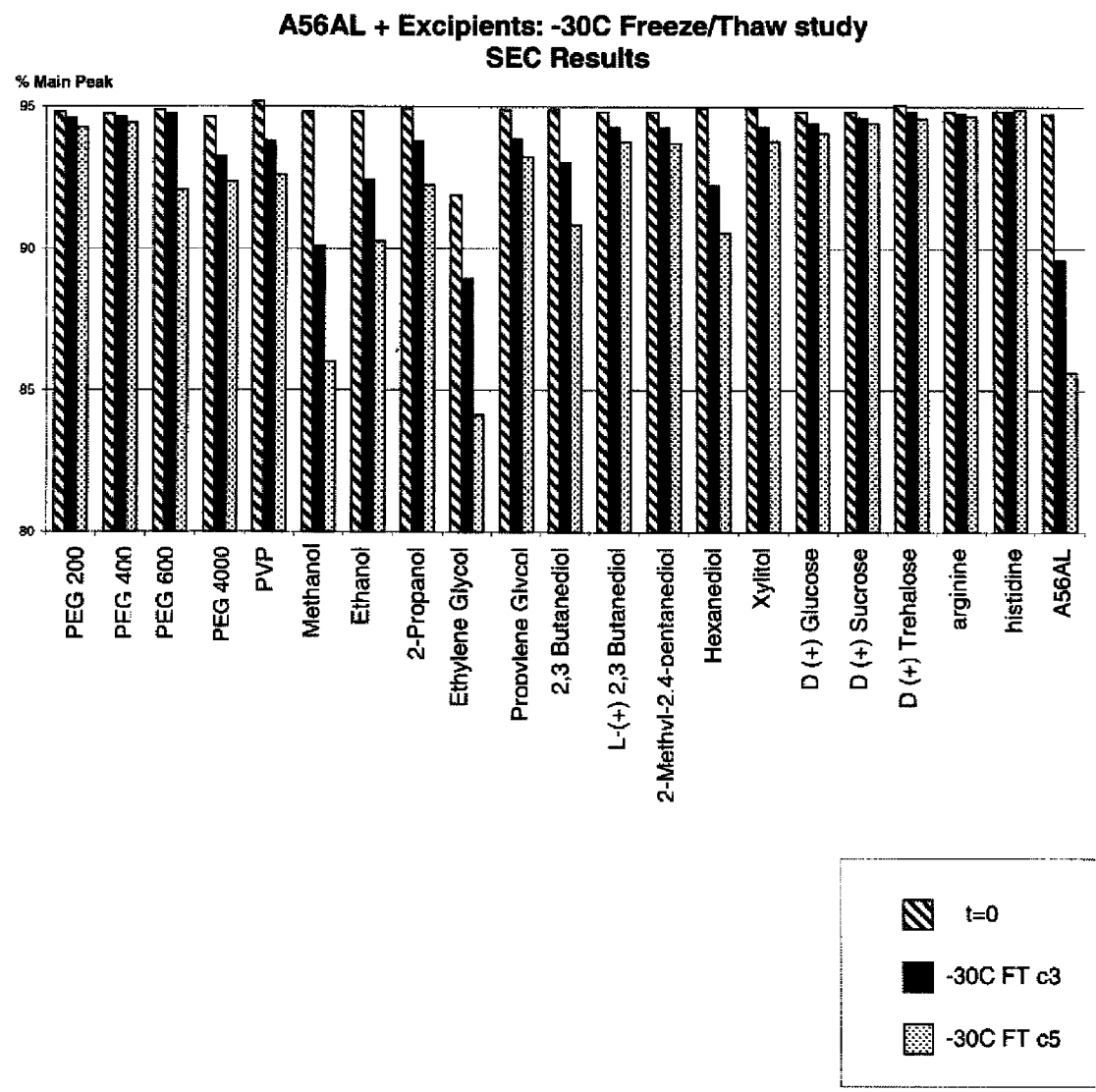
FIG. 14 (*a*) shows the results of native SEC-HPLC analysis (expressed as percent main peak (monomer)) of various 2.12.1 compositions subjected to zero, three, or five freeze/thaw cycles, with the freeze temperature at −30° C., according to the work discussed in Example 4.
Figure 14:
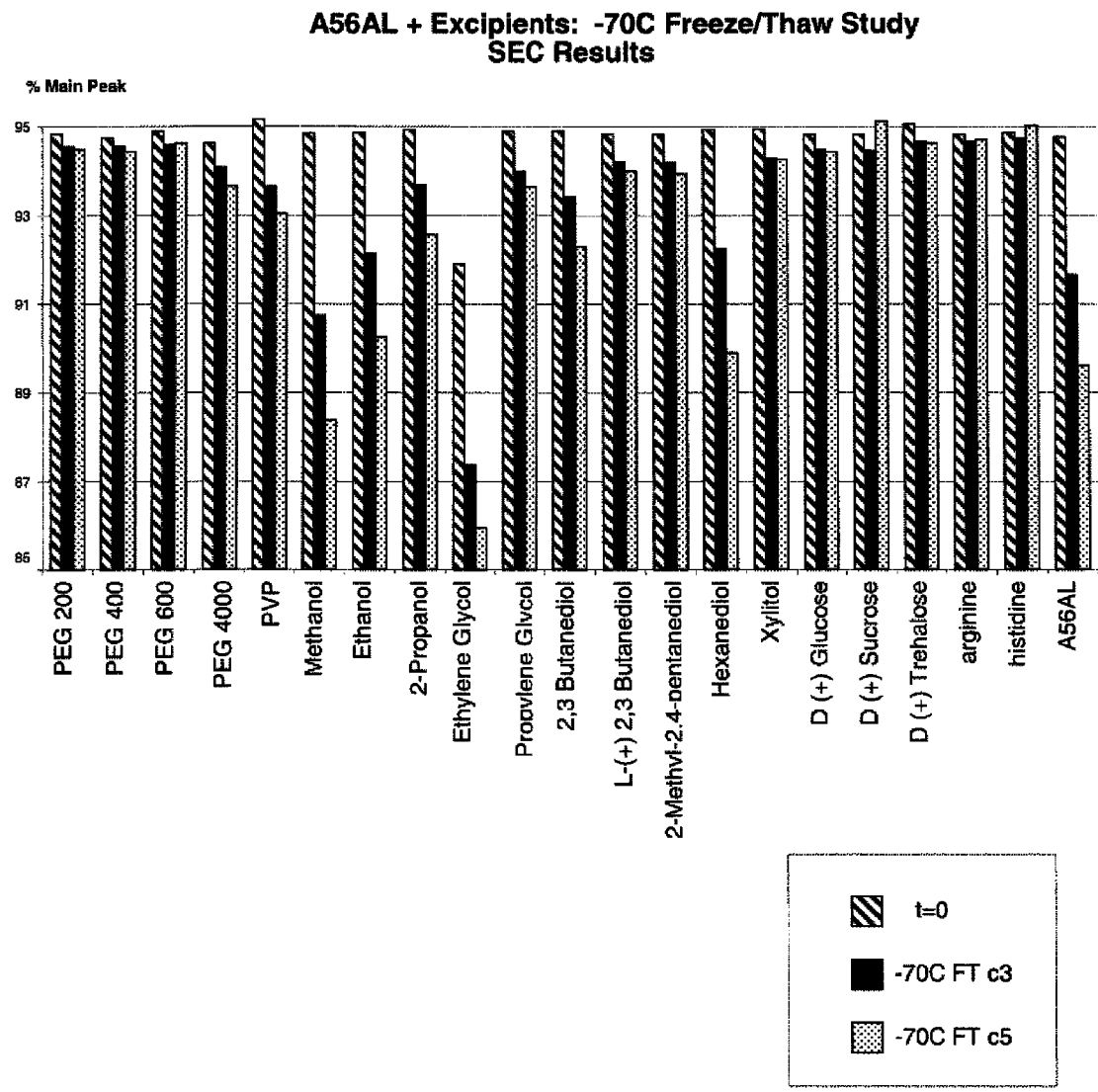
Figure 15:
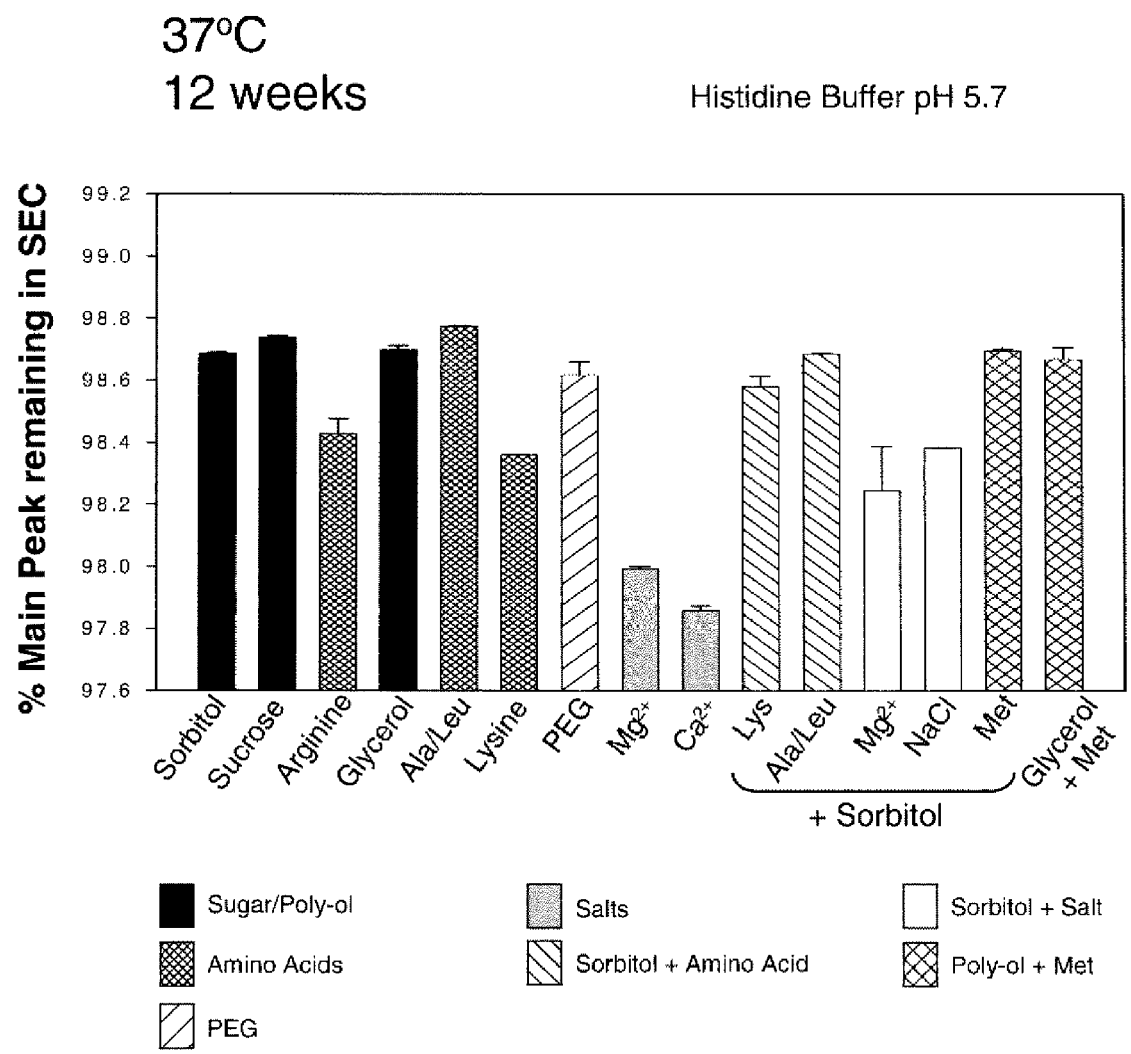
FIG. 15 shows the results of native SEC-HPLC analysis (expressed as percent main peak (monomer)) of various 2.12.1 compositions incubated at 37° C. for 12 weeks according to the work discussed in Example 5.
Figure 16:
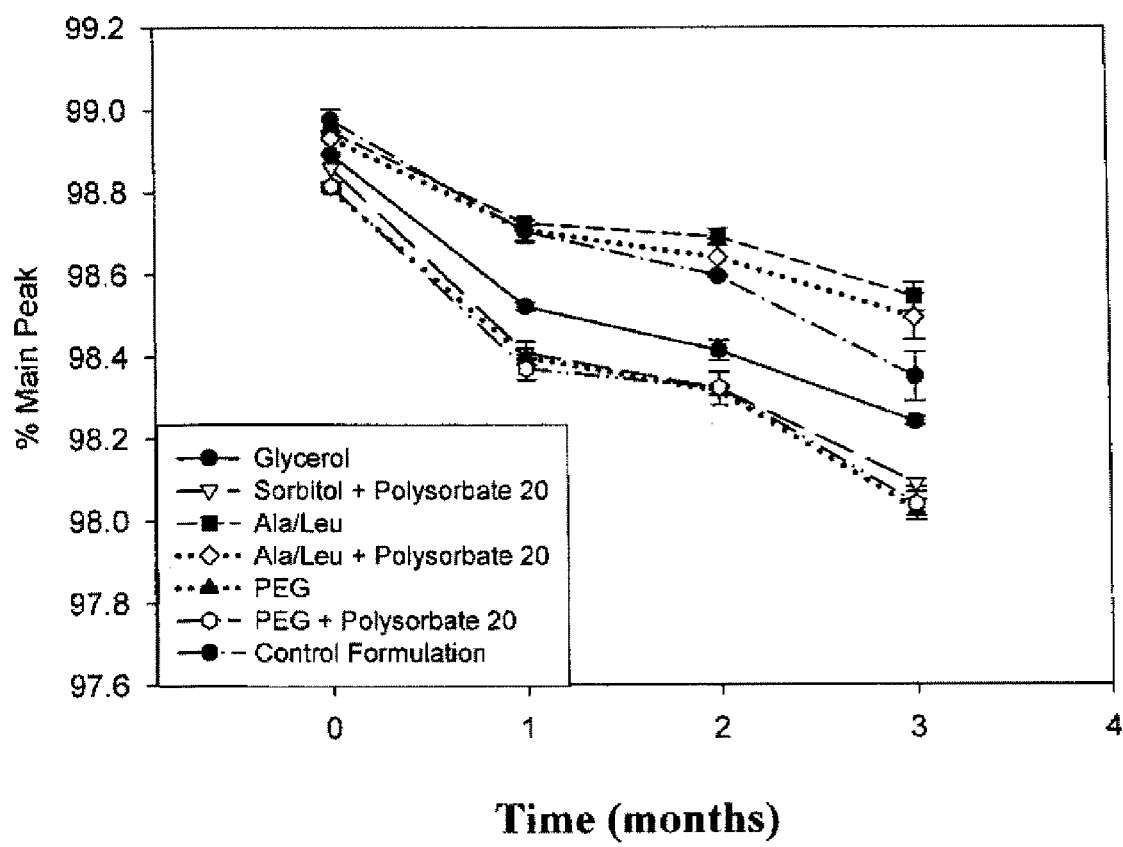
FIG. 16 shows the results of native SEC-HPLC analysis (expressed as percent main peak (monomer)) of various 2.12.1 compositions incubated at 37° C. for 0 months, 1 month, 2 months, or 3 months according to the work discussed in Example 6.

For each composition at each number of freeze/thaw cycles indicated in FIGS. 14 (a) and (b), a sample was removed from each vial for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIGS. 14 (a) and (b) show the results of native SEC-HPLC analysis of certain 2.12.1 compositions listed in Table 5 (as indicated along each horizontal axis of FIGS. 14 (a) and (b)) subjected to zero, three, or five freeze/thaw cycles (as indicated in each legend of FIGS. 14 (a) and (b)), with the freeze temperature at –30° C. (FIG. 14 (a)) or at –70° C. (FIG. 14 (b)). "% Main Peak" reflects the quantity of 2.12.1 monomer. The results indicate that the "% Main Peak" for A56AL, the 2.12.1 formulation containing a combination of L-alanine and L-leucine and lacking an agent (Table 5, FIGS. 14 (a) and (b)), decreased by about 9% when subjected to freeze/thaw cycles, suggesting aggregate formation. In contrast, the "% Main Peak" for 18 of the 2.12.1 formulations containing a combination of L-alanine and L-leucine and an agent (Table 5, FIGS. 14 (a) and (b)) showed minor or no significant changes when subjected to freeze/thaw cycles. The 18 agents in those formulations were PEG 200, PEG 400, PEG 600, PEG 4000, polyvinylpyrrolidone K15, ethanol, 2-propanol, propylene glycol, 2,3-butanediol, L-(+)-2,3-butanediol, (±)2-methyl-2,4-pentanediol, 1,6-hexanediol, xylitol, glucose, sucrose, trehalose, arginine, and histidine. Thus, the data suggests that each of those 18 agents reduced aggregate formation in compositions of 2.12.1 formulated in a combination of L-alanine and L-leucine when those compositions were subjected to one or more freeze/thaw cycles. Therefore, it may be desirable to include any of those agents, as cryoprotectants, in compositions of a specific binding agent to HGF formulated in one or more non-polar amino acids and subjected to one or more freeze/thaw cycles.

Example 5

To evaluate the effects of different compositions on a specific binding agent to HGF, compositions of 2.12.1 were formulated in 15 different formulations shown in Table 6 below. The concentration of 2.12.1 in all formulations was 30 mg/ml. Compositions were filled to a final volume of 2 ml in 3-cc vials. Compositions were incubated at 37° C. for twelve weeks.

TABLE 6

| Formulation | Stabilizing agent(s) | Buffering agent | pH | Polysorbate 20 |
|---|---|---|---|---|
| Sorbitol | 5% (w/v) sorbitol | 10 mM L-his | 5.7 | .004% |
| Sucrose | 9.5% sucrose | 10 mM L-his | 5.7 | .004% |
| Arginine | 140 mM L-arg | 10 mM L-his | 5.7 | .004% |
| Glycerol | 2.6% glycerol | 10 mM L-his | 5.7 | .004% |
| Ala/Leu | 200 mM L-ala; 75 mM L-leu | 10 mM L-his | 5.7 | .004% |
| Lysine | 140 mM L-lys | 10 mM L-his | 5.7 | .004% |
| PEG | .25% PEG 8000 | 10 mM L-his | 5.7 | .004% |
| $Mg^{2+}$ | 110 mM $Mg^{2+}$ | 10 mM L-his | 5.7 | .004% |
| $Ca^{2+}$ | 110 mM $Ca^{2+}$ | 10 mM L-his | 5.7 | .004% |
| Lys + Sorbitol | 25 mM L-lys; 5% sorbitol | 10 mM L-his | 5.7 | .004% |
| Ala/Leu + Sorbitol | 20 mM L-ala; 20 mM L-leu; 5% sorbitol | 10 mM L-his | 5.7 | .004% |
| $Mg^{2+}$ + Sorbitol | 25 mM $Mg^{2+}$; 5% sorbitol | 10 mM L-his | 5.7 | .004% |
| NaCl + Sorbitol | 25 mM NaCl; 5% sorbitol | 10 mM L-his | 5.7 | .004% |
| Met + Sorbitol | 1 mM L-met; 5% sorbitol | 10 mM L-his | 5.7 | .004% |
| Glycerol + Met | 2.6% glycerol; 1 mM L-ala | 10 mM L-his | 5.7 | .004% |

For each composition, at 12 weeks, a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIG. 15 shows the results of native SEC-HPLC analysis of the 2.12.1 compositions listed in Table 5 incubated at 37° C. for 12 weeks. The results indicate that the "% Main Peak" after 12 weeks at 37° C. was highest in the 2.12.1 formulation containing a combination of L-alanine and L-leucine.

Example 6

To evaluate the effects of different compositions on a specific binding agent to HGF, compositions of 2.12.1 were formulated in 7 different formulations shown in Table 7 below. The concentration of 2.12.1 in all formulations was 30 mg/ml. Compositions were filled to a final volume of 2 ml in 5-cc vials. Compositions were incubated at 37° C. for 0, 1, 2, or 3 months.

TABLE 7

| Formulation | Stabilizing agent(s) | Buffering agent | pH | Polysorbate 20 |
|---|---|---|---|---|
| Glycerol | 2.6% glycerol | 10 mM propionate | 5.7 | |
| Sorbitol + Polysorbate 20 | 5% (w/v) sorbitol | 10 mM propionate | 5.7 | 0.004% (w/v) |
| Ala/Leu | 200 mM L-ala; 75 mM L-leu | 10 mM propionate | 5.7 | |
| Ala/Leu + Polysorbate 20 | 200 mM L-ala; 75 mM L-leu | 10 mM propionate | 5.7 | 0.004% (w/v) |
| PEG | 0.25% PEG 8000 | 10 mM propionate | 5.7 | |
| PEG + Polysorbate 20 | 0.25% PEG 8000 | 10 mM propionate | 5.7 | 0.004% (w/v) |
| Control | None | 10 mM acetate | 5.2 | None |

For each composition, at certain timepoints (0 months, 1 month, 2 months, or 3 months), a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIG. 16 shows the results of native SEC-HPLC analysis of the 2.12.1 compositions listed in Table 6 incubated at 37° C. for 0 month, 1 month, 2 months, or 3 months. The results indicate that the "% Main Peak" after 3 months at 37° C. was highest in the 2.12.1 formulations containing a combination of L-alanine and L-leucine. The results also indicate that the addition of polysorbate 20 to a 2.12.1 composition in a formulation containing either a combination of L-alanine and L-leucine or PEG did not have a measurable effect on stability in this assay.

Example 7

To evaluate the effects of different compositions on a specific binding agent to HGF, compositions of 2.12.1 were formulated in 4 different formulations shown in Table 8 below. The concentration of 2.12.1 in all formulations was 30 mg/ml. Compositions were filled to a final volume of 2 ml in 5-cc vials. Compositions were incubated at 4° C. for two years.

TABLE 8

| Formulation | Stabilizing agent(s) | Buffering agent | pH | Polysorbate 20 |
|---|---|---|---|---|
| A52ST | 5% (w/v) sorbitol | 10 mM sodium acetate | 5.2 | 0.004% (w/v) |
| KP6SuT | 9.25% (w/v) sucrose | 10 mM potassium phosphate | 6.0 | 0.004% (w/v) |
| P57ST | 5% (w/v) sorbitol | 10 mM sodium propionate | 5.7 | 0.004% (w/v) |
| P57AlaLeuT | 200 mM L-ala; 75 mM L-leu | 10 mM sodium propionate | 5.7 | 0.004% (w/v) |

For each composition, at two years, a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

Figure 17:
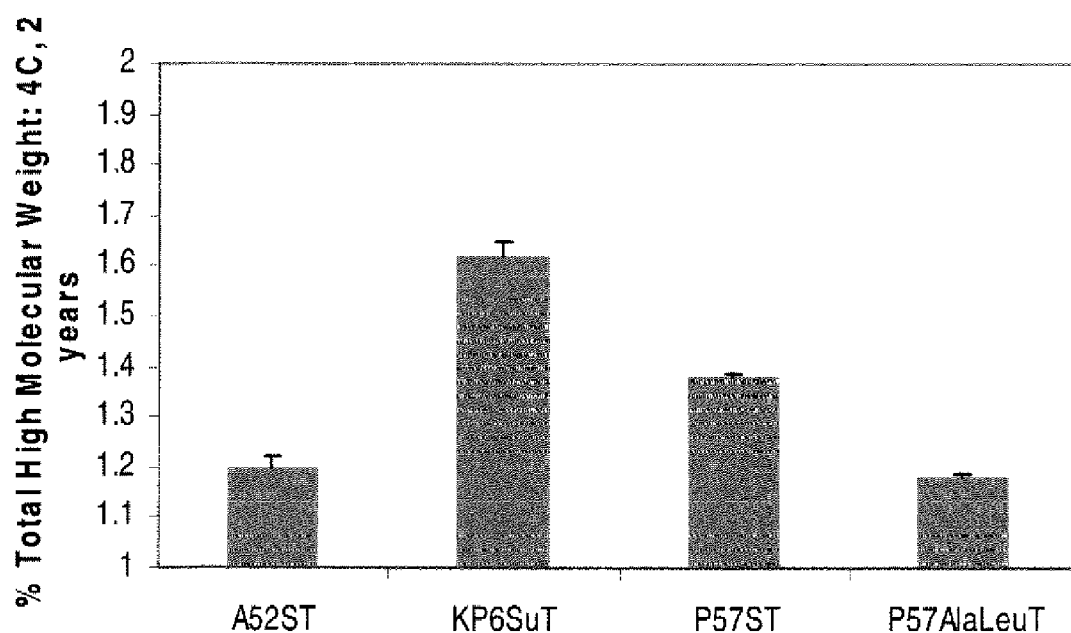
FIG. 17 shows the results of native SEC-HPLC analysis (expressed as percent high molecular weight species) of various 2.12.1 compositions incubated at 4° C. for 2 years according to the work discussed in Example 7.

FIG. 17 shows the results of native SEC-HPLC analysis of the 2.12.1 compositions listed in Table 7 (as indicated in FIG. 17) incubated at 4° C. for two years. The results indicate that the "% Total High Molecular Weight" after 2 years at 4° C. was lowest in the following two 2.12.1 formulations: (1) the formulation containing propionate as a buffering agent and a combination of L-alanine and L-leucine as a stabilizing agent; and (2) the formulation containing acetate as a buffering agent and sorbitol as a stabilizing agent.

Example 8

To evaluate the effects of different compositions on a specific binding agent to HGF, compositions of 2.12.1 were formulated in 6 different formulations shown in Table 9 below. The concentration of 2.12.1 in all formulations was 30 mg/ml. Compositions were filled to a final volume of 0.5 ml in 3-cc vials. Compositions were incubated at 37° C. for 0 weeks, 1 week, 2 weeks, 4 weeks, or 3 months, or at −30° C. for 0 weeks, 4 weeks, or 3 months.

TABLE 9

| Formulation | Stabilizing agent(s) | Buffering agent | pH | Polysorbate 20 |
|---|---|---|---|---|
| A56AL | 200 mM L-ala; 75 mM L-leu | 10 mM sodium acetate | 5.6 | None |
| A56AL PEG200 | 200 mM L-ala; 75 mM L-leu; 100 mM PEG 200 | 10 mM sodium acetate | 5.6 | None |
| A56S | 5% (w/v) sorbitol | 10 mM sodium acetate | 5.6 | None |
| A56ALT | 200 mM L-ala; 75 mM L-leu | 10 mM sodium acetate | 5.6 | .004% |
| A56AL PEG200T | 200 mM L-ala; 75 mM L-leu; 100 mM PEG 200 | 10 mM sodium acetate | 5.6 | .004% |
| A56ST | 5% (w/v) sorbitol | 10 mM sodium acetate | 5.6 | .004% |

For each composition, at certain timepoints (0 weeks, 1 week, 2 weeks, 4 weeks, or 3 months), a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

Figure 18:
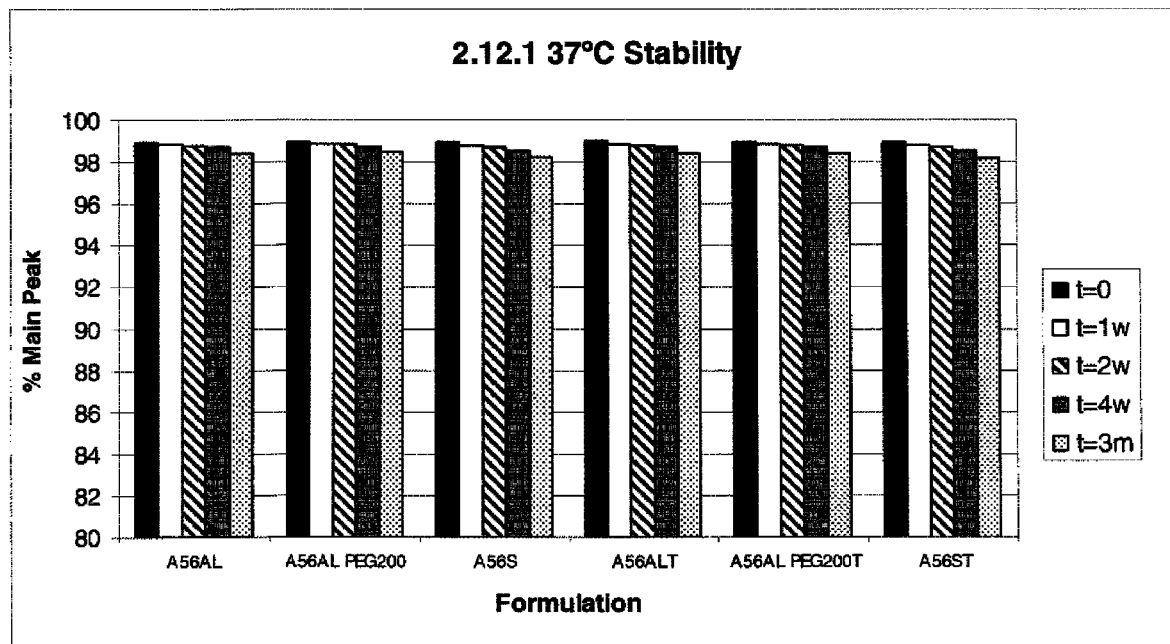
FIG. 18 (a) shows the results of native SEC-HPLC analysis (expressed as percent main peak (monomer)) of various 2.12.1 compositions incubated at 37° C. for 0 weeks, 1 week, 2 weeks, 4 weeks, or 3 months according to the work discussed in Example 8.
Figure 18:
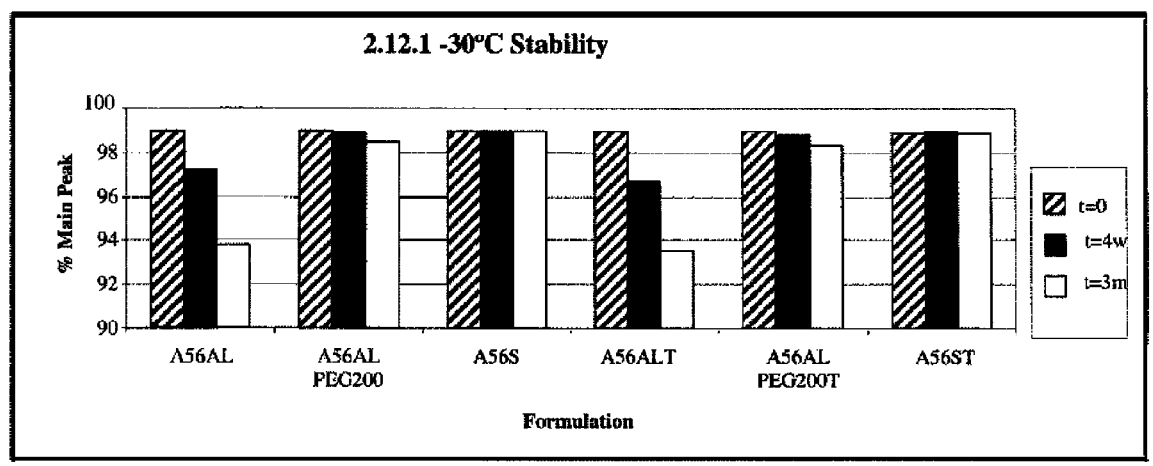

FIG. 18 (a) shows the results of native SEC-HPLC analysis of the 2.12.1 compositions listed in Table 8 incubated at 37° C. for 0 weeks, 1 week, 2 weeks, 4 weeks, or 3 months. The A56AL formulation contained a combination of L-alanine and L-leucine. The A56AL PEG200 formulation contained a combination of L-alanine and L-leucine and PEG 200. The results indicate that for both the A56AL and A56AL PEG200 formulations, the "% Main Peak" decreased only slightly when the compositions were incubated at 37° C. for 3 months. The results indicate that the addition of PEG 200 to a formulation containing a combination of L-alanine and L-leucine did not have a measurable effect on stability in this assay. The results also indicate that the addition of polysorbate 20 to a formulation containing: (1) a combination of L-alanine and L-leucine; (2) a combination of L-alanine and L-leucine and PEG 200; or (3) or sorbitol; did not have a measurable effect on stability in this assay.

FIG. 18 (b) shows the results of native SEC-HPLC analysis of the 2.12.1 compositions listed in Table 8 incubated at −30° C. for 0 weeks, 4 weeks, or 3 months. The A56AL formulation contained a combination of L-alanine and L-leucine. The A56AL PEG200 formulation contained a combination of L-alanine and L-leucine and PEG 200. The results indicate that for A56AL, the "% Main Peak" decreased by about 5% when the composition was incubated at −30° C. for 3 months. In contrast, for the A56AL PEG200 formulation, the "% Main Peak" decreased by less than 1% when the composition was incubated at −30° C. for 3 months. The data suggest that PEG 200 reduced aggregate formation in a composition of 2.12.1 formulated in a combination of L-alanine and L-leucine when that composition was incubated at −30° C. for 3 months. The results also indicate that the addition of polysorbate 20 to a 2.12.1 formulation containing: (1) a combination of L-alanine and L-leucine; (2) a combination of L-alanine and L-leucine and PEG; or (3) sorbitol; did not have a significant effect on stability in this assay.

Example 9

To evaluate the effects of different agents in compositions subjected to one or more freeze/thaw cycles on a specific binding agent to HGF, compositions of 2.12.1 were formulated in 3 different formulations shown in Table 9: A56L; A56L PEG200; and A56S. The concentration of 2.12.1 in all formulations was 30 mg/ml. All of the formulations contained 10 mM sodium acetate, pH 5.6. Compositions were filled to a final volume of 0.5 ml in 3-cc vials.

Compositions were subjected to 0, 1, 5, or 10 freeze/thaw cycles, with the freeze temperature at −30° C. For each cycle, compositions were placed in a −30° C. freezer for 16 hours and then thawed by placing at room temperature (25° C.) for one to two hours. After thawing, compositions were stored at 4° C. for up to ten days and then analyzed by native SEC-HPLC.

For each composition, at 0, 1, 5, or 10 freeze/thaw cycles (as indicated in the FIG. 19 legend), a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

Figure 19:
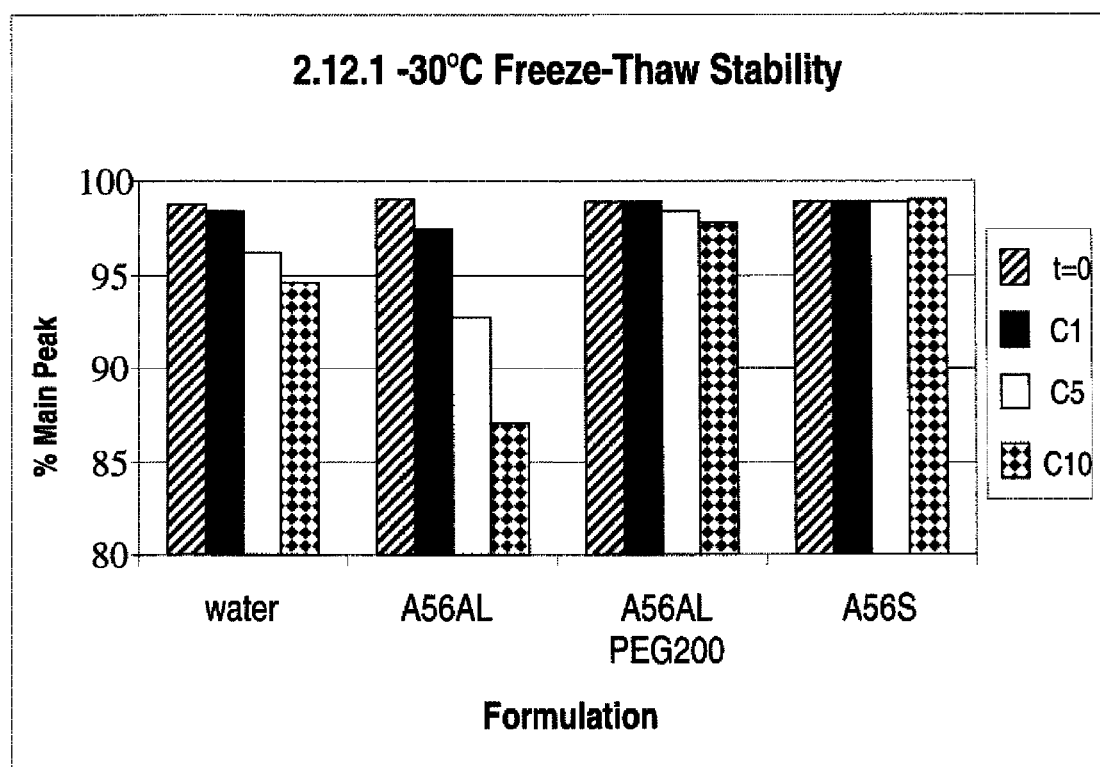
FIG. 19 shows the results of native SEC-HPLC analysis (expressed as percent main peak (monomer)) of various 2.12.1 compositions subjected to zero, one, five, or ten freeze/thaw cycles, with the freeze temperature at −30° C., according to the work discussed in Example 9.
Figure 20:
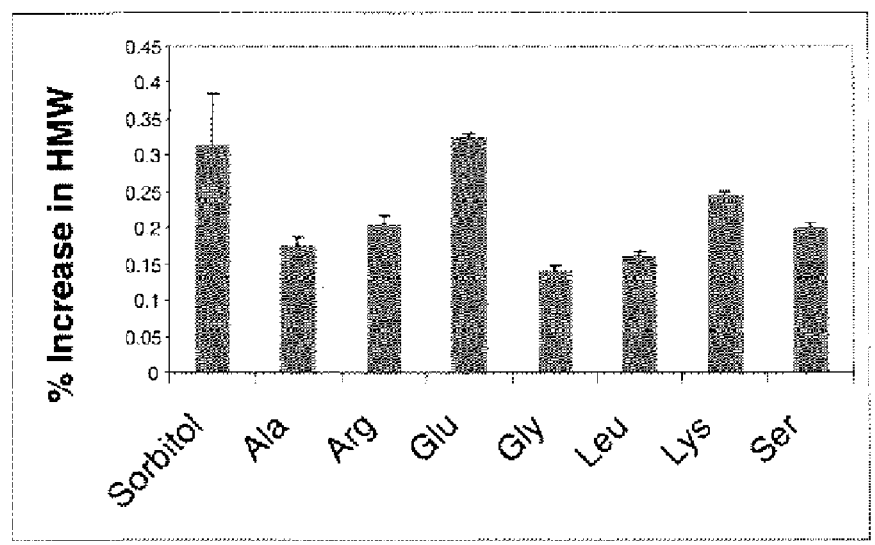
FIG. 20 (a) shows the results of native SEC-HPLC analysis (expressed as percent high molecular weight species) of various 2.12.1 compositions incubated at 37° C. for 4 weeks according to the work discussed in Example 10.
Figure 20:
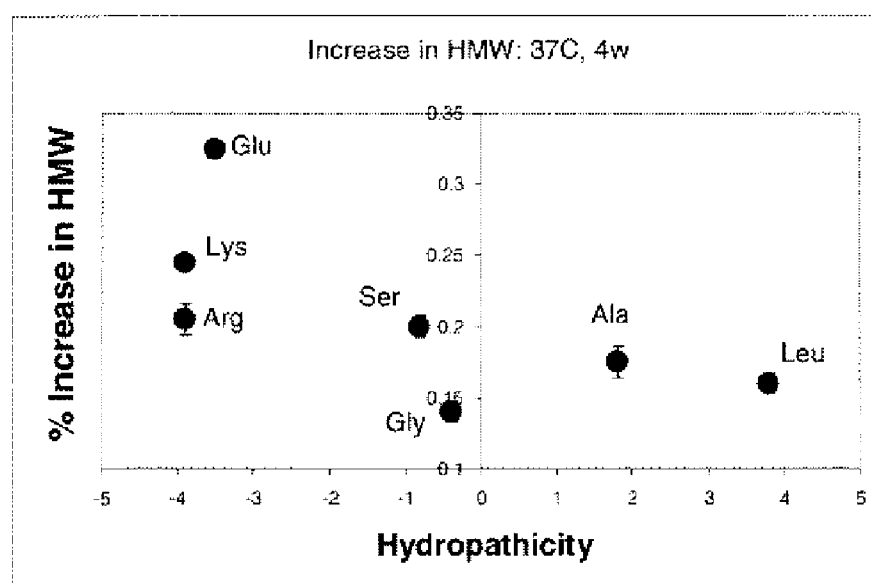
Figure 21:
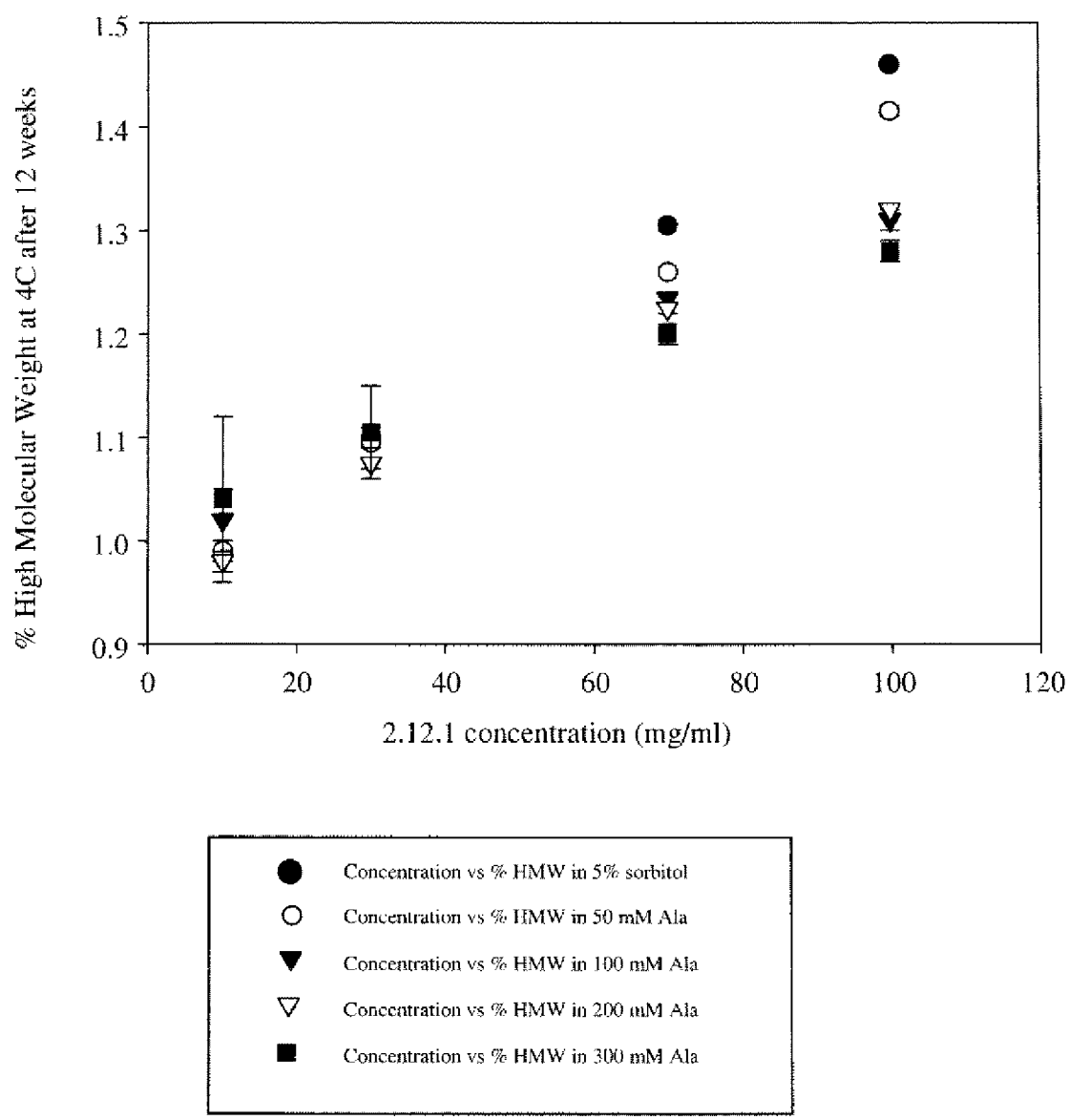
FIG. 21 shows a plot of "2.12.1 concentration" vs. "% High Molecular Weight" of various 2.12.1 compositions incubated at 4° C. for 12 weeks according to the work discussed in Example 11.
Figure 22:
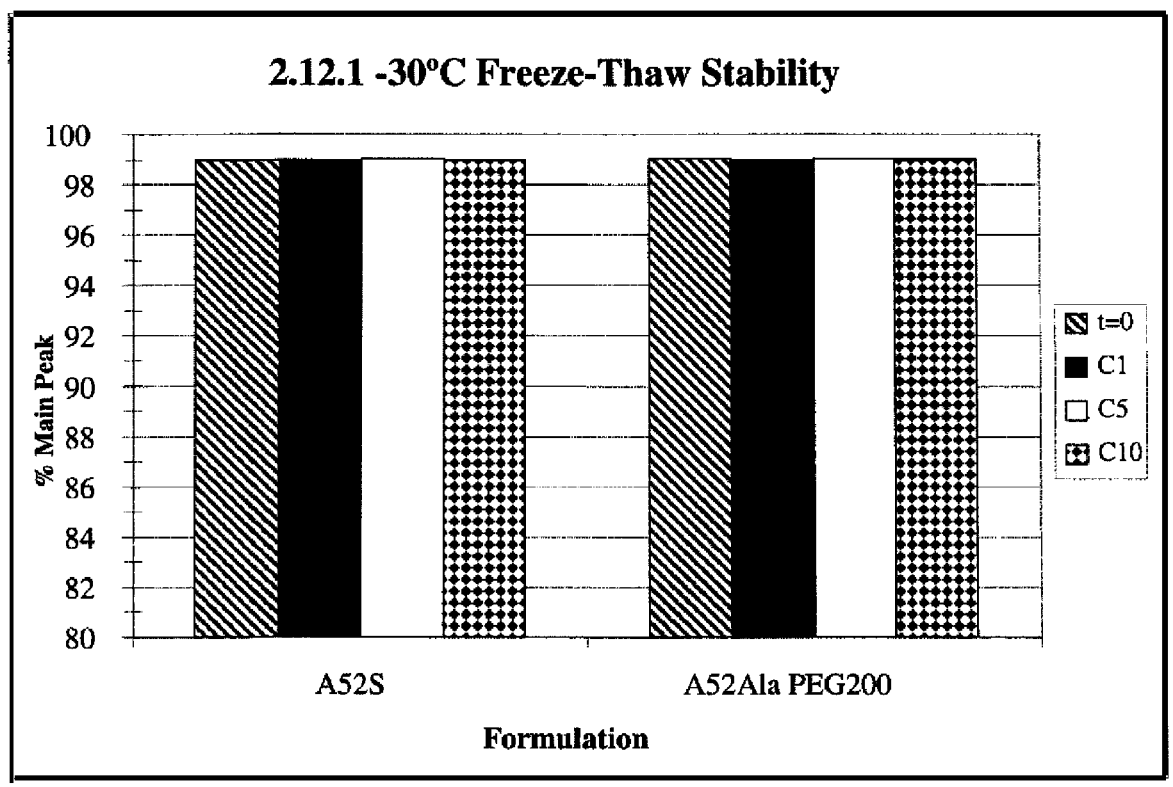
FIG. 22 shows the results of native SEC-HPLC analysis (expressed as percent main peak (monomer)) of two 2.12.1 compositions subjected to zero, one, five, or ten freeze/thaw cycles, with the freeze temperature at −30° C., according to the work discussed in Example 12.

FIG. 19 shows the results of native SEC-HPLC analysis of 2.12.1 compositions subjected to 0, 1, 5, or 10 freeze/thaw cycles. "Water" contained only 2.12.1 and water. The A56AL formulation contained a combination of L-alanine and L-leucine. The A56AL PEG200 formulation contained a combination of L-alanine and L-leucine and PEG 200. The results indicate that for Water, the "% Main Peak" decreased by about 4 to 5% when the composition was subjected to 10 freeze/thaw cycles, suggesting aggregate formation. The results further indicate for A56AL, the "% Main Peak" decreased by about 12% when the composition was subjected to 10 freeze/thaw cycles, suggesting that a combination of L-alanine and L-leucine increased aggregate formation compared to water. The results further indicate that for A56AL PEG200, the "% Main Peak" decreased by about 1% when the composition was subjected to 10 freeze/thaw cycles. The results suggest that the addition of PEG to a combination of L-alanine and L-leucine resulted in decreased aggregate formation as compared to a combination of L-alanine and L-leucine.

Example 10

To evaluate the effects of different compositions on a specific binding agent to HGF, compositions of 2.12.1 were formulated in 8 different formulations shown in Table 10 below. The concentration of 2.12.1 in all formulations was 30 mg/ml. Compositions were filled to a final volume of 0.25 ml in 3-cc vials. Compositions were incubated at 37° C. for four weeks.

TABLE 10

| Formulation | Stabilizing agent(s) | Buffering agent | pH | Polysorbate 20 |
|---|---|---|---|---|
| Sorbitol | 5% (w/v) sorbitol | 10 mM acetate | 5.2 | |
| Alanine | 100 mM L-alanine | 10 mM acetate | 5.2 | |
| Arginine | 100 mM L-arginine | 10 mM acetate | 5.2 | |
| Glutamate | 100 mM L-glutamate | 10 mM acetate | 5.2 | |
| Glycine | 100 mM L-glycine | 10 mM acetate | 5.2 | |
| Leucine | 100 mM L-leucine | 10 mM acetate | 5.2 | |
| Lysine | 100 mM L-lysine | 10 mM acetate | 5.2 | |
| Serine | 100 mM L-serine | 10 mM acetate | 5.2 | |

For each composition, at four weeks, a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIG. 20 (*a*) shows the results of native SEC-HPLC analysis of the 2.12.1 compositions listed in Table 10 incubated at 37° C. for four weeks. The results indicate that there was less "% Increase in HMW" in the formulations containing L-glycine, L-leucine, L-alanine, L-arginine, and L-serine than in the formulations containing L-lysine, L-glutamate, or sorbitol.

FIG. 20 (*b*) shows, for each of the amino acids contained in a formulation in Table 10, a plot of the "% Increase in HMW" v. the hydropathic index of the amino acid. The results indicate that the four most hydropathic amino acids, L-leucine, L-alanine, L-glycine, and L-serine, were among the amino acids with the smallest % Increase in HMW.

Example 11

To evaluate the effects of different compositions on a specific binding agent to HGF at different concentrations of that specific binding agent, compositions of 2.12.1 were formulated in 20 different formulations. Five different stabilizing agents were tested: 5% sorbitol, 50 mM L-alanine, 100 mM L-alanine, 200 mM L-alanine, and 300 mM L-alanine. For each formulation, four different concentrations of 2.12.1 were tested: 10, 30, 70, and 100 mg/ml. Each formulation contained 10 mM sodium acetate, pH 5.2, as a buffering agent. Compositions were filled to a final volume of 0.25 ml in 3-cc vials Compositions were incubated at 4° C. for 3 months.

For each composition, at 3 months, a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIG. 21 shows a plot of "2.12.1 concentration" vs. "1% High Molecular Weight" after 3 months at 4° C. The results indicate that at 2.12.1 concentrations of 10 and 30 mg/ml, the "% High Molecular Weight" was similar for each of the formulations. The results further indicate that at 2.12.1 concentrations of 70 and 100 mg/ml, the "% High Molecular Weight" was lower for L-alanine than it was for sorbitol.

Example 12

To evaluate the effects of different agents in compositions subjected to one or more freeze/thaw cycles on a specific binding agent to HGF, compositions of 2.12.1 were formulated in sorbitol ("A52S) or in L-alanine and PEG 200 ("A52Ala PEG200"). The concentration of 2.12.1 in each formulation was 30 mg/ml. Each formulation contained 10 mM sodium acetate, pH 5.2. A52S contained 5% (w/v) sorbitol. A52Ala PEG200 contained 100 mM L-alanine and 200 mM PEG 200. Compositions were filled to a final volume of 0.5 ml in 3-cc vials.

Compositions were subjected to 0, 1, 5, or 10 freeze/thaw cycles, with the freeze temperature at −30° C. For each cycle, compositions were placed in a −30° C. freezer for 16 hours and then thawed by placing at room temperature (25° C.) for one to two hours. After thawing, compositions were stored at 4° C. for up to ten days and then analyzed by native SEC-HPLC.

For each composition, at 0, 1, 5, or 10 freeze/thaw cycles (as indicated in the FIG. 22 legend), a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

FIG. 22 shows the results of native SEC-HPLC analysis of 2.12.1 compositions subjected to 0, 1, 5, or 10 freeze/thaw cycles. The A52S formulation contained sorbitol. The A52Ala PEG200 formulation contained L-alanine and PEG 200. The results indicate that for both A52S and A52Ala PEG200, the "% Main Peak" did not change when the composition was subjected to freeze/thaw cycles.

Example 13

To evaluate the effects of different agents in compositions subjected to one or more freeze/thaw cycles on a specific binding agent to HGF, compositions of 2.12.1 were formulated in sorbitol ("A56S") or in L-alanine and PEG 200 ("A56AlaP"). The concentration of 2.12.1 in each formulation was 30 mg/ml. Each formulation contained 10 mM sodium acetate, pH 5.6. A56S contained 5% (w/v) sorbitol. A56AlaP contained 100 mM L-alanine and 200 mM PEG 200. Compositions were filled to a final volume of 0.5 ml in 3-cc vials.

Compositions were subjected to 0, 5, or 10 freeze/thaw cycles, with the freeze temperature at −30° C. For each cycle, compositions were placed in a −30° C. freezer for 16 hours and then thawed by placing at room temperature (25° C.) for one to two hours. After thawing, compositions were stored at 4° C. for up to ten days and then analyzed by native SEC-HPLC.

For each composition, at 0, 5, or 10 freeze/thaw cycles (as indicated in the FIG. 23 legend), a sample was removed for analysis by native SEC-HPLC. Native SEC-HPLC was performed using a TSK-GEL Super SW3000 4.6 mm×30 cm column (Tosoh Bioscience), with 4 μm particle size, on an Agilent 1100 Series HPLC with diode array detection. The mobile phase was 50 mM sodium phosphate, 100 mM sodium chloride, 5% ethanol, pH 7.5. The flow rate was 0.3 ml/minute. The column eluate was monitored at 215 nm and 280 nm. Integrated peak areas in the chromatograms were used to quantify the amounts of monomer and high molecular weight species.

Figure 23:
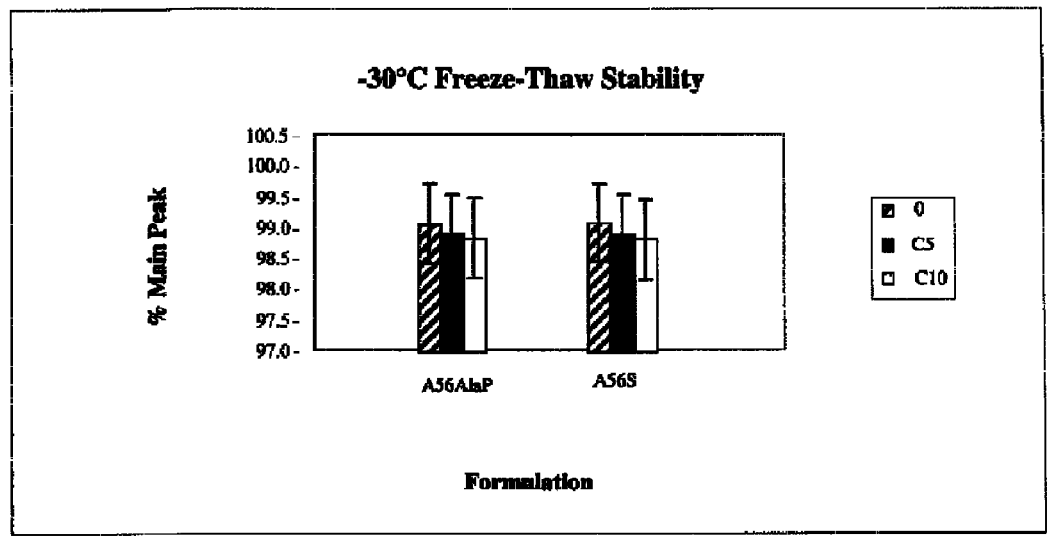
FIG. 23 (a) shows the results of native SEC-HPLC analysis (expressed as percent main peak (monomer)) of two 2.12.1 compositions subjected to zero, five, or ten freeze/thaw cycles, with the freeze temperature at −30° C., according to the work discussed in Example 13.
Figure 23:
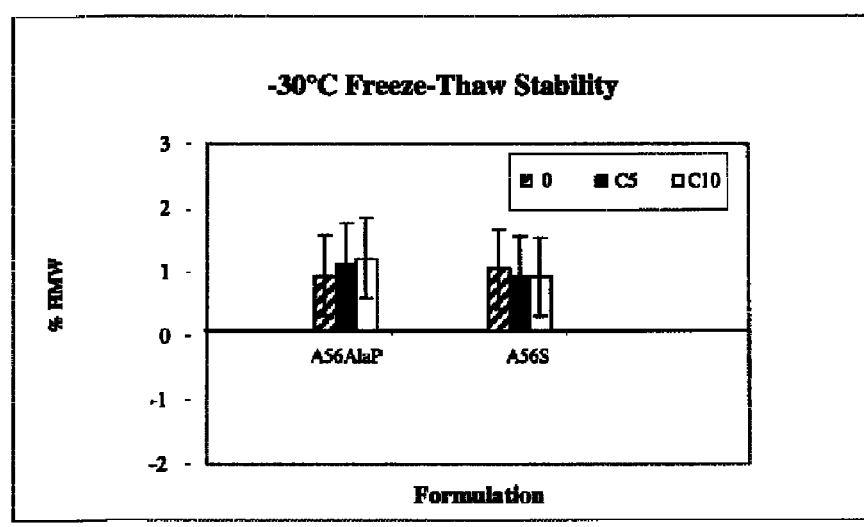

FIG. 23 (a) shows the results of native SEC-HPLC analysis of 2.12.1 compositions subjected to 0, 5, or 10 freeze/thaw cycles. The A56S formulation contained sorbitol. The A56AlaP formulation contained L-alanine and PEG 200. The results (taking into account the error bars) indicate that for both A56S and A56AlaP, the "% Main Peak" remained unchanged when the composition was subjected to freeze/thaw cycles.

FIG. 23 (b) shows the results of native SEC-HPLC analysis of those 2.12.1 compositions subjected to 0, 5, or 10 freeze/thaw cycles. The A56S formulation contained sorbitol. The A56AlaP formulation contained L-alanine and PEG 200. The results (taking into account the error bars) indicate that for both A56S and A56AlaP, the "% HMW" remained unchanged when the composition was subjected to freeze/thaw cycles.

We claim:

1. A composition comprising a specific binding agent to HGF, at least one stabilizing agent, and a buffering agent, wherein the at least one stabilizing agent comprises alanine and leucine, and wherein the pH of the composition is above 5.4.

2. The composition of claim 1, wherein the specific binding agent is selected from an antibody, a polyclonal antibody, a monoclonal antibody, an antibody wherein the heavy chain and the light chain are connected by a flexible linker, an Fv molecule, a maxibody, an immunologically functional immunoglobulin fragment, a Fab fragment, a Fab' fragment, a F(ab')$_2$ molecule, a fully human antibody, a humanized antibody, a chimeric antibody, and an antibody that substantially inhibits binding of HGF to a c-Met receptor.

3. The composition of claim 2, wherein the specific binding agent is a fully human antibody, wherein the fully human antibody is 2.12.1.

4. The composition of claim 1, further comprising at least one additional pharmaceutical agent.

5. The composition of claim 1, wherein the at least one stabilizing agent further comprises methionine, and wherein discoloration of the composition is reduced.

6. The composition of claim 1, wherein the at least one stabilizing agent further comprises at least one cryoprotectant.

7. The composition of claim 6, wherein the at least one cryoprotectant is selected from polyvinylpyrrolidone K15, polyethylene glycol 200, polyethylene glycol 400, polyethylene glycol 600, polyethylene glycol 4000, and polyethylene glycol 30,000.

8. The composition of claim 6, wherein the at least one stabilizing agent further comprises methionine, and wherein discoloration of the composition is reduced.

9. The composition of claim 8, wherein the at least one cryoprotectant is selected from polyvinylpyrrolidone K15, polyethylene glycol 200, polyethylene glycol 400, polyethylene glycol 600, polyethylene glycol 4000, and polyethylene glycol 30,000.

* * * * *